(12) United States Patent
Gitman et al.

(10) Patent No.: US 11,234,899 B2
(45) Date of Patent: Feb. 1, 2022

(54) GRASPING FACILITATORS AND USES THEREOF AND KITS INVOLVING THE SAME

(71) Applicant: ScalPal, LLC, Baltimore, MD (US)

(72) Inventors: Eliot Robert Gitman, Jerusalem (IL); Tuvia Gitman, Jerusalem (IL)

(73) Assignee: SCALPAL LLC, Wilmington, DE (US)

( * ) Notice: Subject to any disclaimer, the term of this patent is extended or adjusted under 35 U.S.C. 154(b) by 0 days.

(21) Appl. No.: 15/977,358

(22) Filed: May 11, 2018

(65) Prior Publication Data

US 2018/0325774 A1 Nov. 15, 2018

Related U.S. Application Data

(60) Provisional application No. 62/505,034, filed on May 11, 2017.

(51) Int. Cl.
*A61D 17/00* (2006.01)
*A61J 1/20* (2006.01)
(Continued)

(52) U.S. Cl.
CPC .............. *A61J 1/2055* (2015.05); *A61J 1/16* (2013.01); *A61J 1/2065* (2015.05); *A61J 1/2096* (2013.01);
(Continued)

(58) Field of Classification Search
CPC ....... B65B 21/18; A61J 1/2055; A61J 1/2065; A61J 1/16; A61J 1/2096; A61J 7/0069; A61M 2209/08; A61M 2209/088
(Continued)

(56) References Cited

U.S. PATENT DOCUMENTS

| 135,809 A | 2/1873 | Hubbard |
|---|---|---|
| 181,716 A | 8/1876 | Pickles |

(Continued)

FOREIGN PATENT DOCUMENTS

| CN | 2010/23742 Y | 2/2008 |
|---|---|---|
| DE | 29606408 U1 | 6/1996 |

(Continued)

OTHER PUBLICATIONS

Office Action for U.S. Appl. No. 15/977,431 dated Feb. 19, 2020.
(Continued)

*Primary Examiner* — Don M Anderson
*Assistant Examiner* — Elizabeth J Volz
(74) *Attorney, Agent, or Firm* — Smith, Gambrell & Russell, LLP

(57) ABSTRACT

There is featured a grasping facilitator that has one or more of a) to c) as set forth below: a) a combination having an annular core and a plurality of gripping ribs spaced about the annular core, with the core and gripping ribs being formed of an elastomeric material and the ribs extending about an upper part, outer part and bottom part of the core so as to leave an interior region of the core that is aligned radially with respective ribs exposed; b) a pliable collar having a main body with a plurality of ridges separated by concave recesses and a central aperture; c) a tray holder having an aperture or projection that has a configuration designed to conform with at least one of a) and b). There is further featured kit combinations of a) to c) above as well as methods of using and assembling one or all combinations of a) to c).

22 Claims, 63 Drawing Sheets

(51) Int. Cl.
*A61J 1/16* (2006.01)
*B25B 13/46* (2006.01)
*B25B 21/00* (2006.01)

(52) U.S. Cl.
CPC .............. *B25B 13/46* (2013.01); *B25B 21/00* (2013.01); *A61M 2209/08* (2013.01); *A61M 2209/088* (2013.01)

(58) Field of Classification Search
USPC ........................................................ 220/737
See application file for complete search history.

(56) References Cited

U.S. PATENT DOCUMENTS

| | | | |
|---|---|---|---|
| 225,121 A | 3/1880 | Hackman et al. | |
| 244,379 A | 7/1881 | Coulter et al. | |
| 331,169 A | 11/1885 | Thomas | |
| 332,540 A | 12/1885 | Law | |
| 367,196 A | 7/1887 | Deblieux | |
| 779,751 A | 1/1905 | Waitt | |
| 975,285 A | 11/1910 | Robertson | |
| 1,320,259 A | 10/1919 | Martens | |
| 1,632,227 A * | 6/1927 | Halsey | B25G 1/105 16/421 |
| 1,764,990 A | 6/1930 | Schultz | |
| 1,798,944 A | 3/1931 | Jackman | |
| 1,875,930 A | 9/1932 | Martin | |
| 2,083,045 A | 6/1937 | Vaurs | |
| 2,173,707 A | 9/1939 | Brown | |
| 2,259,425 A | 10/1941 | Murphy | |
| 2,305,472 A | 12/1942 | Hall | |
| 2,335,205 A | 11/1943 | Zepp | |
| 2,538,350 A | 1/1951 | Baule | |
| 2,752,814 A | 7/1956 | Lai | |
| 2,930,424 A | 3/1960 | Van Buren | |
| 3,171,459 A | 3/1965 | Storch | |
| 3,175,454 A | 3/1965 | Morse | |
| 3,208,494 A | 9/1965 | Skidmore | |
| 3,242,775 A | 3/1966 | Hinkle | |
| 3,304,109 A | 2/1967 | Schuster | |
| 3,319,509 A | 5/1967 | Romeo | |
| 3,340,920 A | 9/1967 | Johnson | |
| 3,412,772 A | 11/1968 | Meyfarth et al. | |
| 3,422,721 A | 1/1969 | Yonkers | |
| 3,466,956 A | 9/1969 | Bowers | |
| 3,474,009 A | 10/1969 | Wang | |
| 3,584,531 A | 6/1971 | Greenleaf et al. | |
| 3,584,667 A | 6/1971 | Reiland et al. | |
| 3,628,584 A | 12/1971 | Gutshall | |
| 3,695,324 A | 10/1972 | Gulistan | |
| 3,856,066 A | 12/1974 | Reynolds | |
| 3,931,749 A | 1/1976 | Evans | |
| 4,084,478 A | 4/1978 | Simmons | |
| 4,202,244 A | 5/1980 | Gutshall | |
| 4,291,737 A | 9/1981 | McMurray et al. | |
| 4,292,007 A | 9/1981 | Wagner | |
| 4,293,262 A | 10/1981 | Holmes | |
| 4,355,552 A | 10/1982 | Gutshall | |
| 4,459,074 A | 7/1984 | Capuano | |
| 4,512,220 A | 4/1985 | Barnhill, III et al. | |
| 4,580,322 A | 4/1986 | Wright et al. | |
| 4,581,957 A | 4/1986 | Dossier | |
| 4,598,616 A | 7/1986 | Colvin | |
| 4,646,594 A | 3/1987 | Tien | |
| 4,701,088 A | 10/1987 | Crull | |
| 4,882,957 A | 11/1989 | Wright et al. | |
| 4,895,484 A | 1/1990 | Wilcox | |
| 4,970,922 A | 11/1990 | Krivec | |
| 5,067,750 A | 11/1991 | Minnemann | |
| 5,131,312 A | 7/1992 | Macor | |
| 5,139,380 A | 8/1992 | Reynolds | |
| 5,279,190 A | 1/1994 | Goss et al. | |
| 5,358,368 A | 10/1994 | Conlan et al. | |
| 5,378,101 A | 1/1995 | Olson et al. | |
| 5,386,749 A | 2/1995 | Kim | |
| 5,553,983 A | 9/1996 | Shinjo | |
| 5,577,871 A | 11/1996 | Brugola | |
| 5,578,050 A * | 11/1996 | Webb | A61B 17/3211 16/421 |
| 5,827,027 A | 10/1998 | Wakabayashi | |
| 5,873,290 A | 2/1999 | Chaconas | |
| 5,931,618 A | 8/1999 | Wallace et al. | |
| 6,109,849 A | 8/2000 | Nagayama | |
| 6,129,493 A | 10/2000 | Leistner et al. | |
| 6,227,784 B1 | 5/2001 | Antoine et al. | |
| 6,238,372 B1 | 5/2001 | Zinger | |
| 6,283,689 B1 | 9/2001 | Roythberg et al. | |
| 6,289,772 B1 | 9/2001 | Ying-Wen | |
| 6,293,745 B1 | 9/2001 | Lu | |
| 6,295,900 B1 | 10/2001 | Julicher et al. | |
| 6,321,625 B1 | 11/2001 | Fernandez | |
| 6,575,061 B2 | 6/2003 | Wagner | |
| 6,585,695 B1 | 7/2003 | Adair | |
| 6,626,067 B1 | 9/2003 | Iwinski et al. | |
| 6,715,384 B1 | 4/2004 | Kozak | |
| 6,725,746 B1 | 4/2004 | Wright | |
| 6,755,748 B2 | 6/2004 | Brooks | |
| 6,792,838 B2 | 9/2004 | Brooks et al. | |
| 6,854,943 B2 | 2/2005 | Nagayama | |
| 6,889,580 B1 | 5/2005 | Tseng | |
| 6,904,833 B2 | 6/2005 | Wright | |
| 6,918,725 B2 | 7/2005 | Gauron | |
| 6,988,432 B2 | 1/2006 | Brooks | |
| D514,405 S | 2/2006 | Chaconas | |
| 6,997,085 B2 | 2/2006 | Yamamoto | |
| 7,059,816 B2 | 6/2006 | Toosky | |
| 7,107,879 B1 | 9/2006 | Cheng | |
| 7,228,764 B1 | 6/2007 | Macor | |
| 7,231,851 B2 | 6/2007 | Tuan-Mu | |
| 7,340,983 B2 | 3/2008 | Ling et al. | |
| D568,731 S | 5/2008 | Campbell | |
| 7,373,709 B2 | 5/2008 | Fernando et al. | |
| 7,437,975 B1 | 10/2008 | De Anfrasio | |
| 7,462,007 B2 | 12/2008 | Sullivan et al. | |
| 7,478,986 B2 | 1/2009 | Bushell et al. | |
| 7,568,872 B2 | 8/2009 | Schulz | |
| 7,628,772 B2 * | 12/2009 | McConnell | A61J 1/2096 604/181 |
| 7,674,081 B2 | 3/2010 | Selle | |
| D624,796 S | 10/2010 | Taylor, Jr. | |
| 7,955,036 B2 | 6/2011 | Palm | |
| 7,988,683 B2 | 8/2011 | Adair | |
| 8,065,940 B2 | 11/2011 | Wilson et al. | |
| 8,083,082 B2 | 12/2011 | Sasaki | |
| 8,273,061 B2 | 9/2012 | McConnell | |
| 8,342,061 B2 | 1/2013 | Super | |
| 8,353,230 B2 | 1/2013 | Cole | |
| 8,506,578 B2 | 8/2013 | Smith | |
| 8,545,156 B2 | 10/2013 | Kageyama et al. | |
| 8,562,582 B2 | 10/2013 | Tuckwell | |
| 8,647,035 B2 | 2/2014 | Bakken et al. | |
| 8,696,275 B2 | 4/2014 | Wallace et al. | |
| 8,740,533 B2 | 6/2014 | Gaillard | |
| 8,745,825 B2 | 6/2014 | Gitman | |
| 8,794,113 B2 | 8/2014 | Maury | |
| 8,850,662 B2 | 10/2014 | Gitman et al. | |
| 8,864,725 B2 | 10/2014 | Ranalletta | |
| 8,944,736 B2 | 2/2015 | Figge et al. | |
| 8,955,417 B2 | 2/2015 | Stiebitz et al. | |
| 8,973,471 B2 | 3/2015 | Hsieh | |
| 9,039,673 B2 | 5/2015 | Weitzel et al. | |
| D755,528 S * | 5/2016 | Provenzano | D4/138 |
| 9,422,965 B2 | 8/2016 | Campbell, II | |
| 9,587,688 B2 | 3/2017 | Zdeb et al. | |
| 9,624,962 B2 | 4/2017 | Unseld et al. | |
| 9,638,234 B2 | 5/2017 | Campbell | |
| 9,651,078 B2 | 5/2017 | Santiago-Anadon | |
| 9,664,225 B2 | 5/2017 | Szczukowski et al. | |
| 9,795,536 B2 | 10/2017 | Lev et al. | |
| 9,839,580 B2 | 12/2017 | Lev | |
| 9,907,729 B2 | 3/2018 | Nord | |
| 9,943,463 B2 | 4/2018 | Marks et al. | |
| 10,022,298 B2 | 7/2018 | Marici | |

(56) References Cited

U.S. PATENT DOCUMENTS

| | | |
|---|---|---|
| 10,286,201 B2 | 5/2019 | McKennon |
| 2004/0100097 A1 | 5/2004 | Fukano |
| 2005/0137523 A1 | 6/2005 | Wyatt |
| 2006/0002781 A1 | 1/2006 | Mangapora |
| 2006/0089601 A1 | 4/2006 | Dionigi |
| 2006/0116644 A1 | 6/2006 | Norton |
| 2007/0060904 A1 | 3/2007 | Vedrine |
| 2007/0079894 A1 | 4/2007 | Kraus et al. |
| 2008/0009789 A1 | 1/2008 | Zinger |
| 2008/0172024 A1 | 7/2008 | Yow |
| 2008/0179353 A1 | 7/2008 | Maymon |
| 2008/0249479 A1 | 10/2008 | Zinger |
| 2008/0287914 A1 | 11/2008 | Wyatt |
| 2009/0043282 A1 | 2/2009 | Hughes |
| 2010/0095487 A1 | 4/2010 | Gitman |
| 2010/0140431 A1 | 6/2010 | Van Horne |
| 2011/0264037 A1 | 10/2011 | Foshee et al. |
| 2012/0241332 A1 | 9/2012 | Crossman |
| 2013/0144248 A1 | 6/2013 | Putter et al. |
| 2013/0213193 A1 | 8/2013 | Lukes |
| 2013/0226100 A1 | 8/2013 | Lev |
| 2014/0217099 A1* | 8/2014 | Browne ............... B65D 51/002 220/259.1 |
| 2015/0104269 A1 | 4/2015 | Gillis et al. |
| 2015/0265500 A1 | 9/2015 | Russo et al. |
| 2016/0167838 A1* | 6/2016 | Dong ................. B65D 41/0492 220/255 |
| 2017/0128948 A1* | 5/2017 | Anger ...................... B01L 9/06 |
| 2018/0325776 A1 | 11/2018 | Gitman et al. |

FOREIGN PATENT DOCUMENTS

| | | |
|---|---|---|
| GB | 1032144 | 6/1966 |
| GB | 1205455 | 9/1970 |
| GB | 1360644 | 7/1974 |
| GB | 1398180 | 6/1975 |
| GB | 2141803 | 1/1985 |
| GB | 2153033 | 5/1988 |
| GB | 2271738 A | 4/1994 |
| RU | 2160396 C1 | 12/2000 |
| WO | 2010/037250 A1 | 4/2010 |
| WO | 2015/118521 A1 | 8/2015 |
| WO | 2018/167321 A2 | 9/2018 |
| WO | 2010/037250 A1 | 4/2020 |

OTHER PUBLICATIONS

Polyvinyl chloride, Wikipedia, Website, Accessed May 12, 2017, 19 pages, https://en.wikipedia,org/wiki/Polyvinyl_chloride.

Thermoplastic Elastomer, Wikipedia, Website, Accessed May 12, 2017, 4 pages, https://en.wikipedia.org/wiki/Thermoplastic_elasomer.

TPR: Thermpoplastic Rubber—S&E Specialty Polymers, Website, Accessed May 12, 2017, 2 pages, http://www.sespoly.com/products/tpr-thermoplastic-rubber/.

Office Action for U.S. Appl. No. 15/977,431 dated Sep. 2, 2020 (20 Pages).

Office Action for U.S. Appl. No. 15/977,431 dated Jun. 10, 2020 (25 Pages).

\* cited by examiner

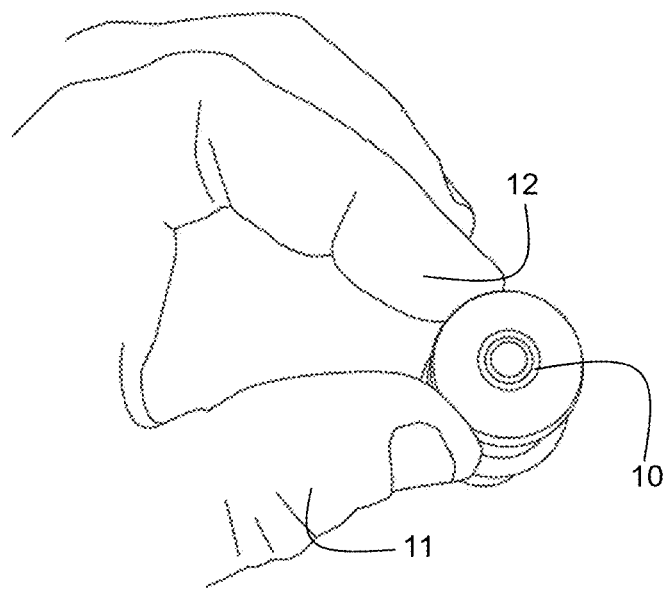
FIG. 1A (Prior Art)
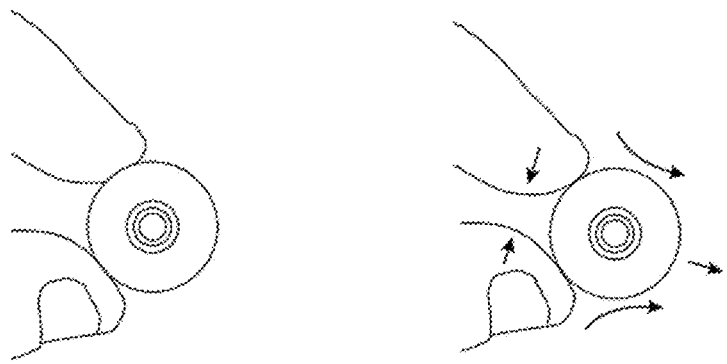
**FIG. 1B
(Prior Art)**
**FIG. 1C
(Prior Art)**
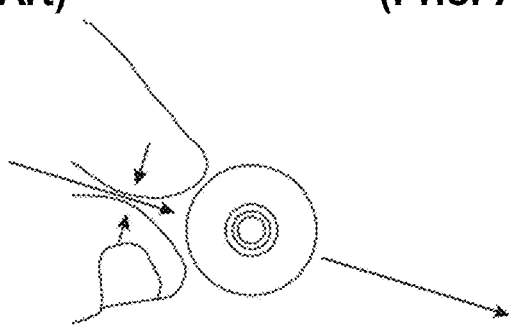
**FIG. 1D
(Prior Art)**

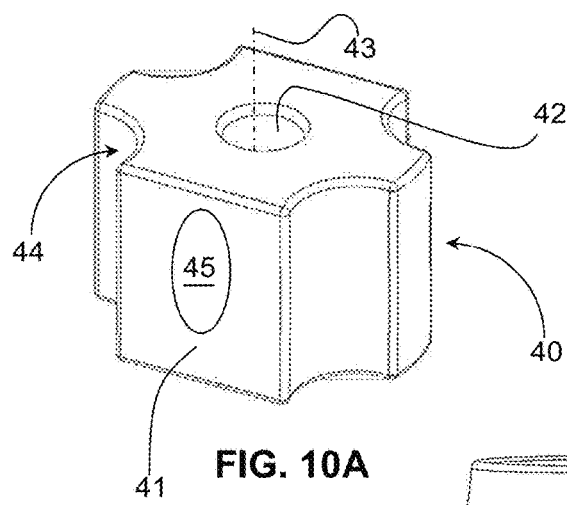
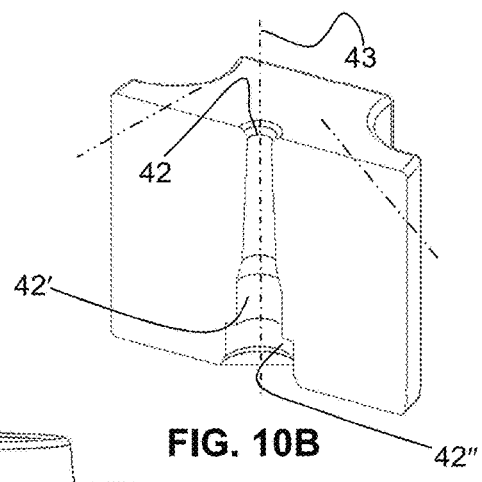
FIG. 10A  FIG. 10B
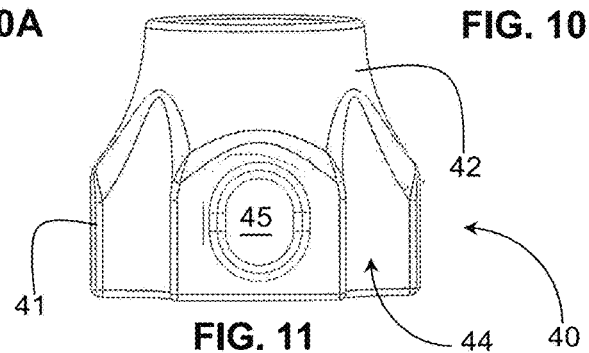
FIG. 11
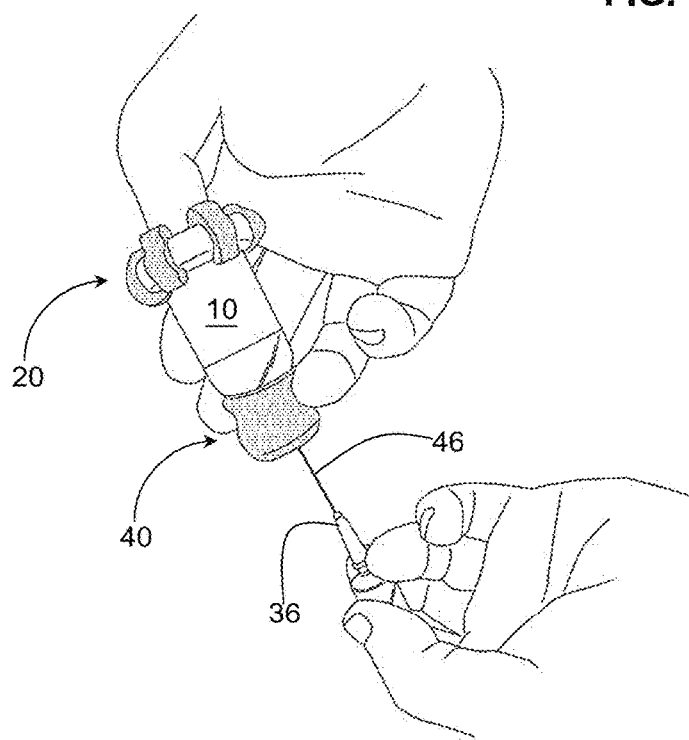
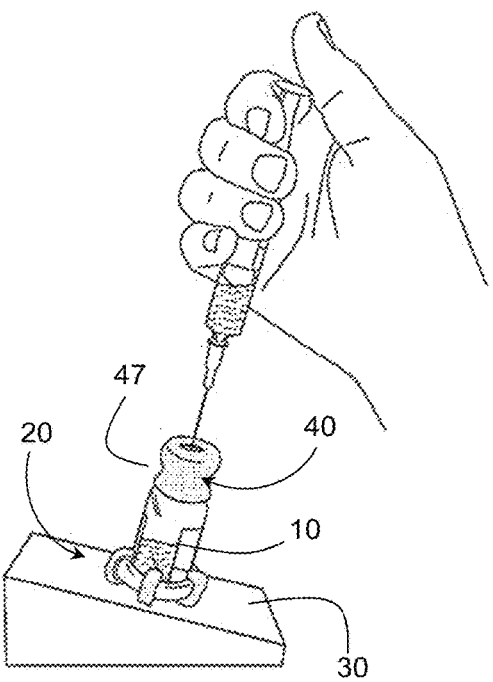
FIG. 12  FIG. 13

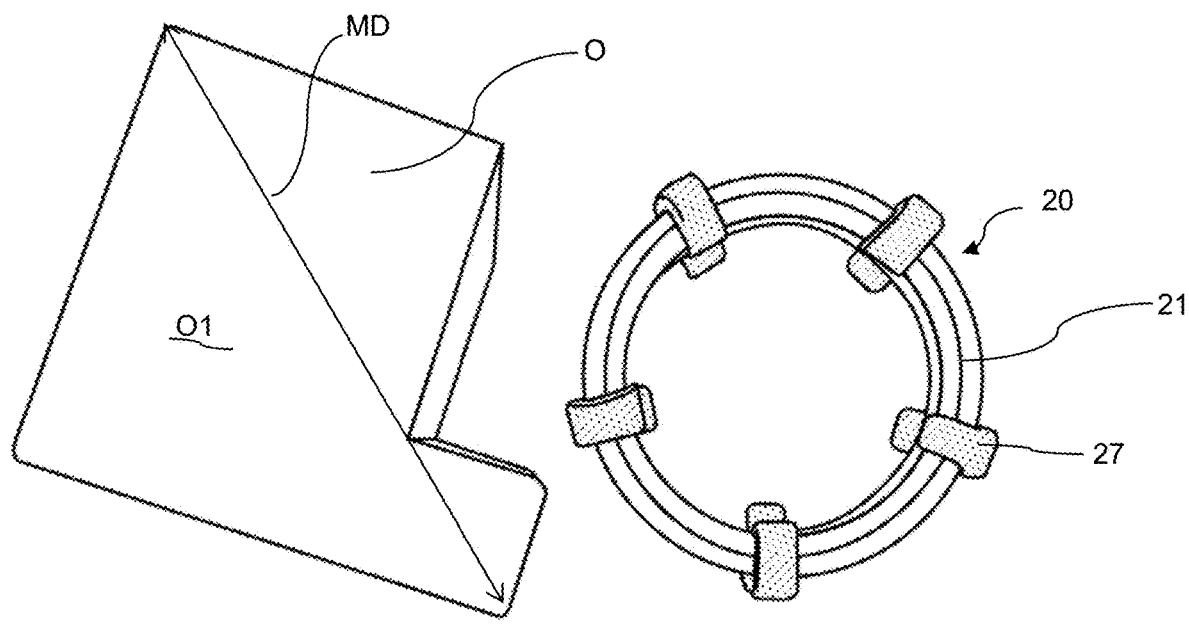
FIG. 32A  FIG. 32B
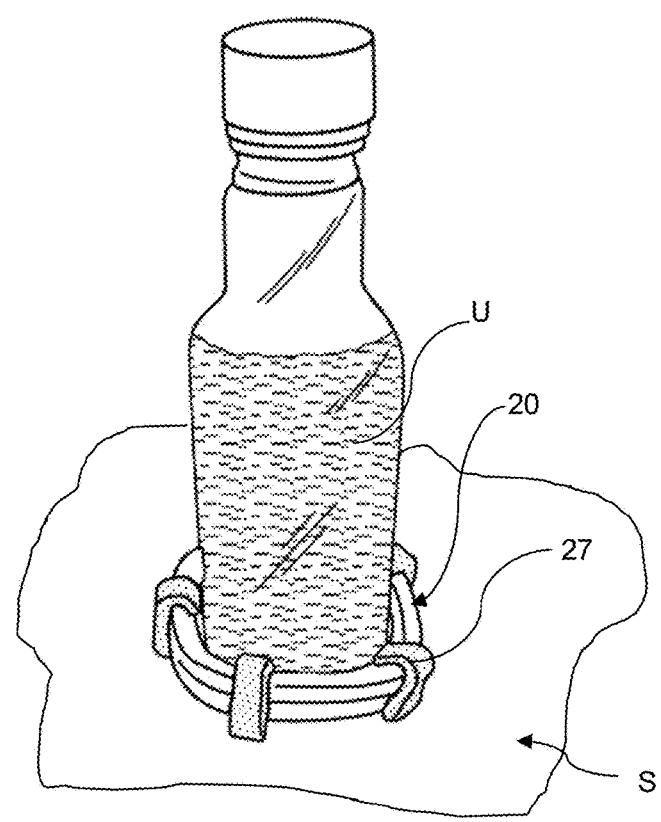
FIG. 33

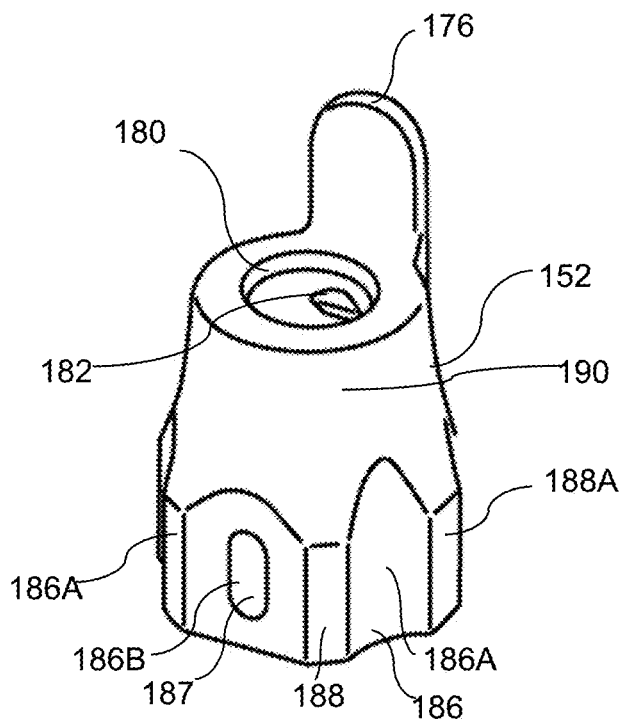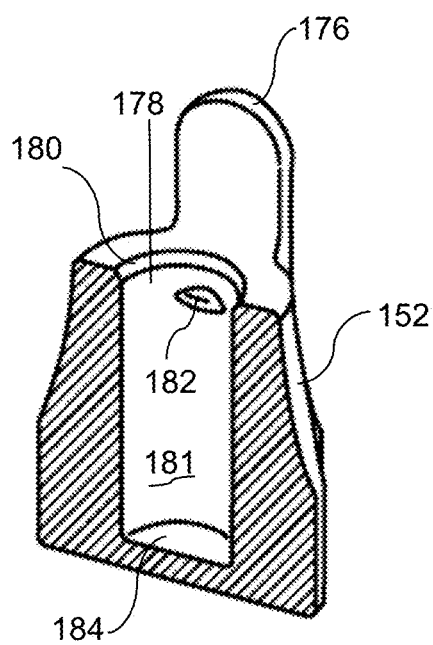
FIG. 52 FIG. 53
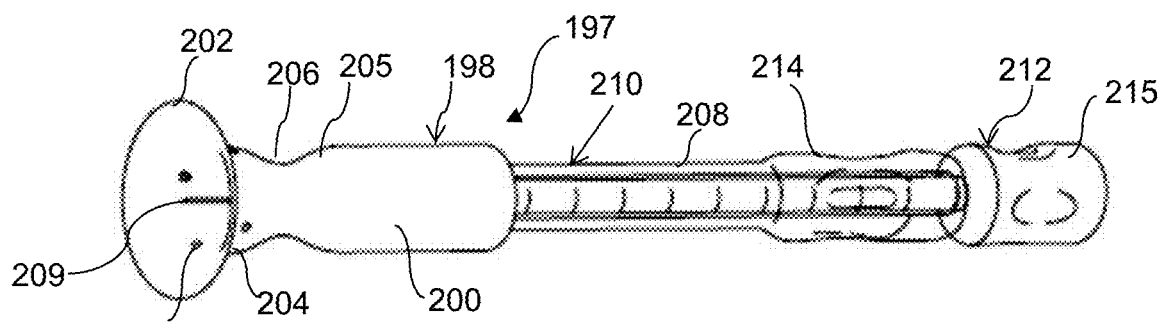
FIG. 54
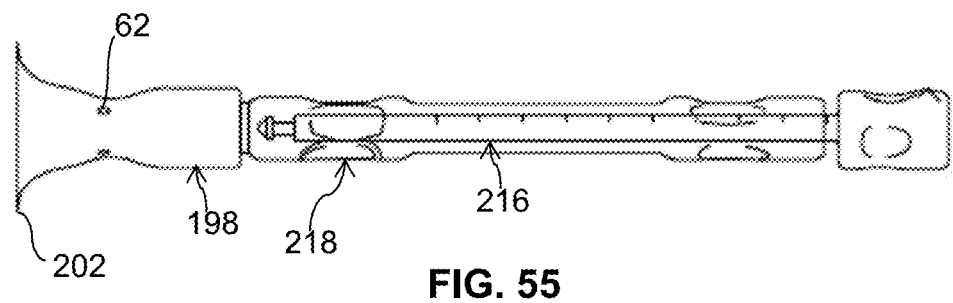
FIG. 55

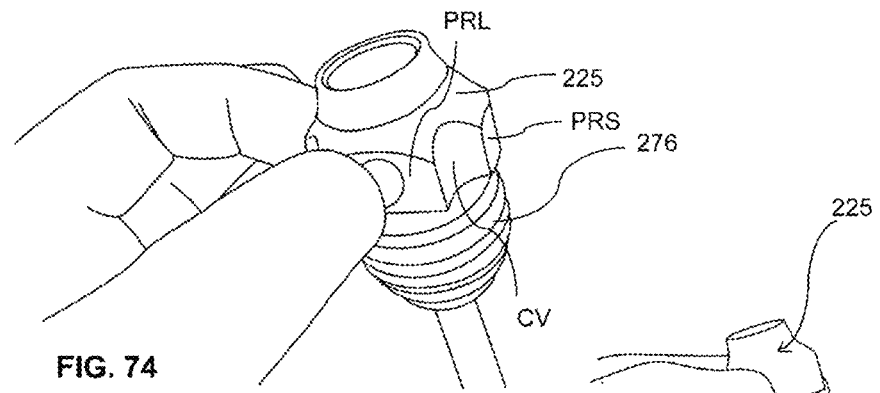
FIG. 74
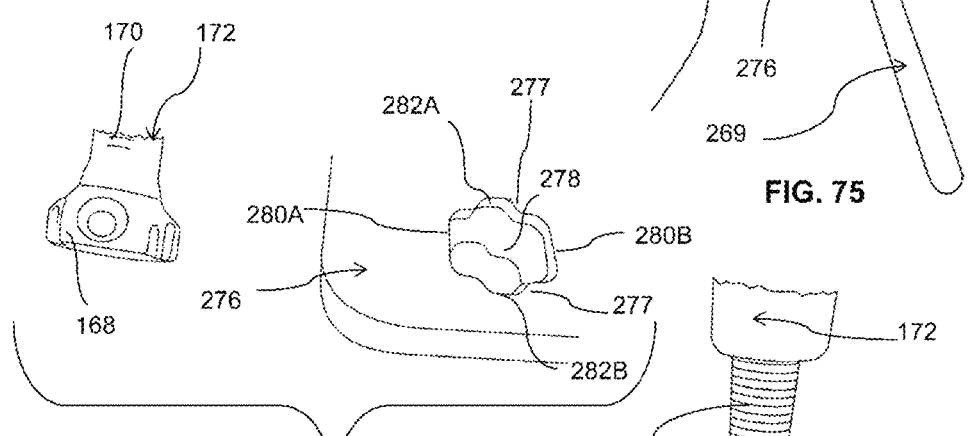
FIG. 75
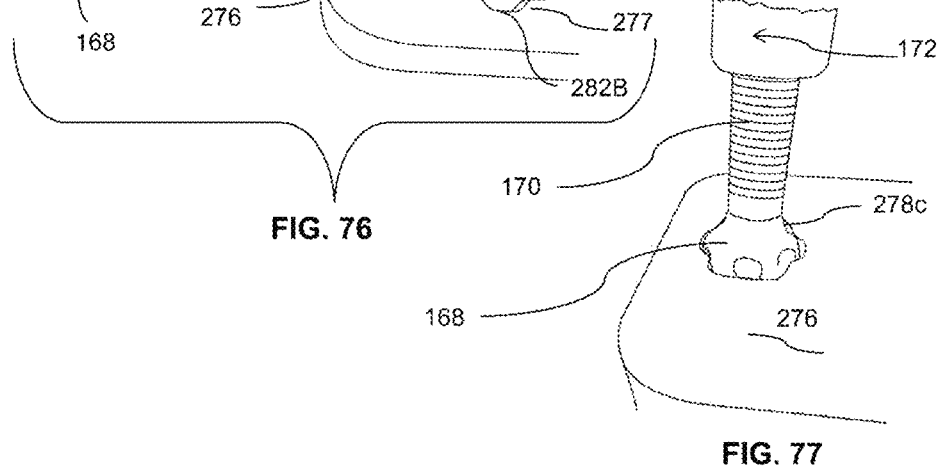
FIG. 76
FIG. 77

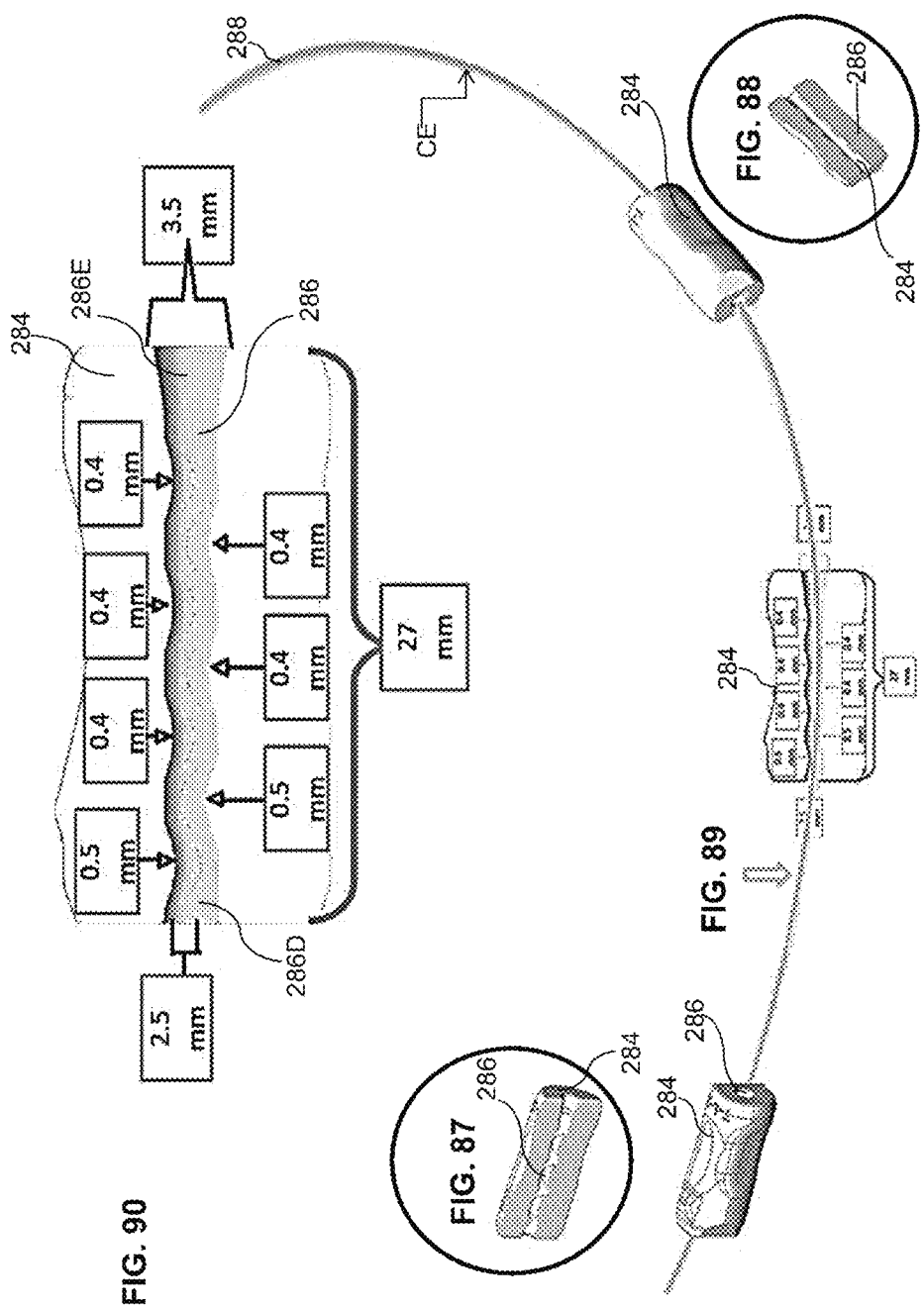

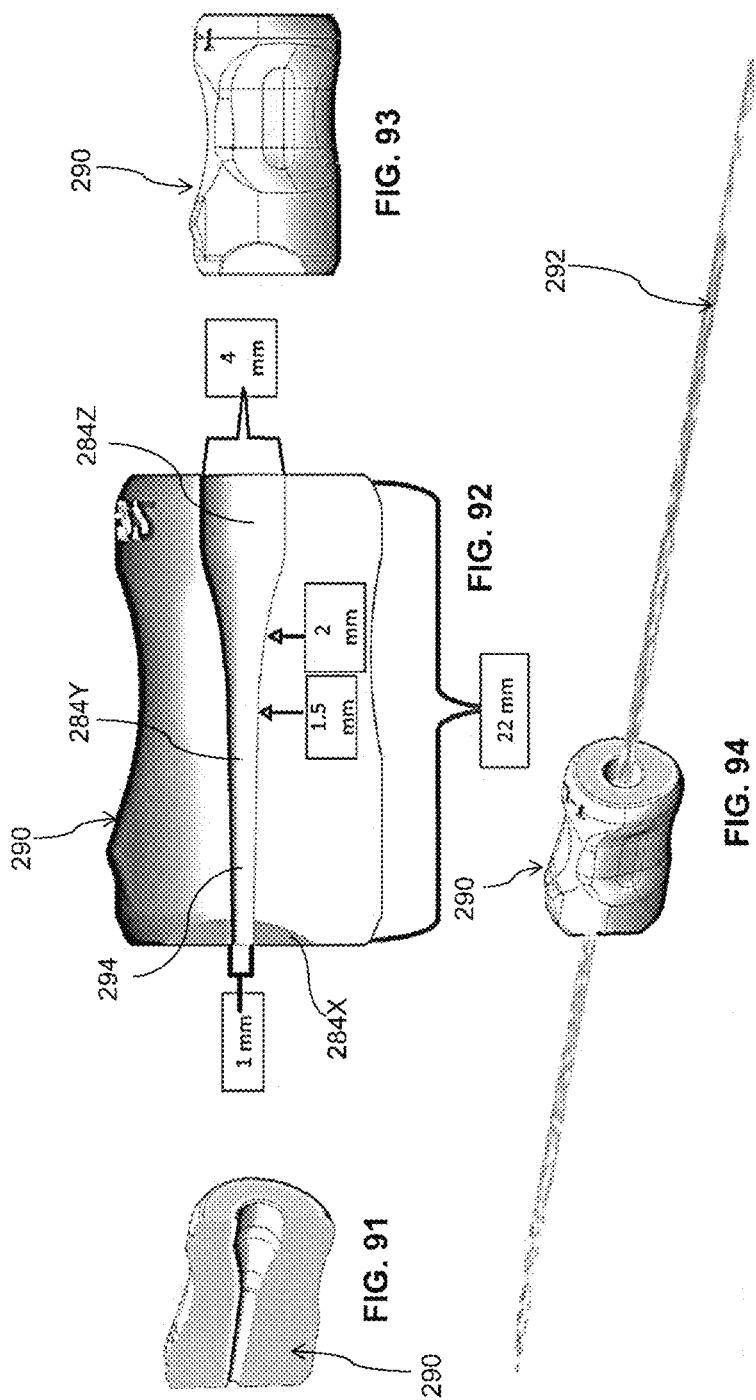

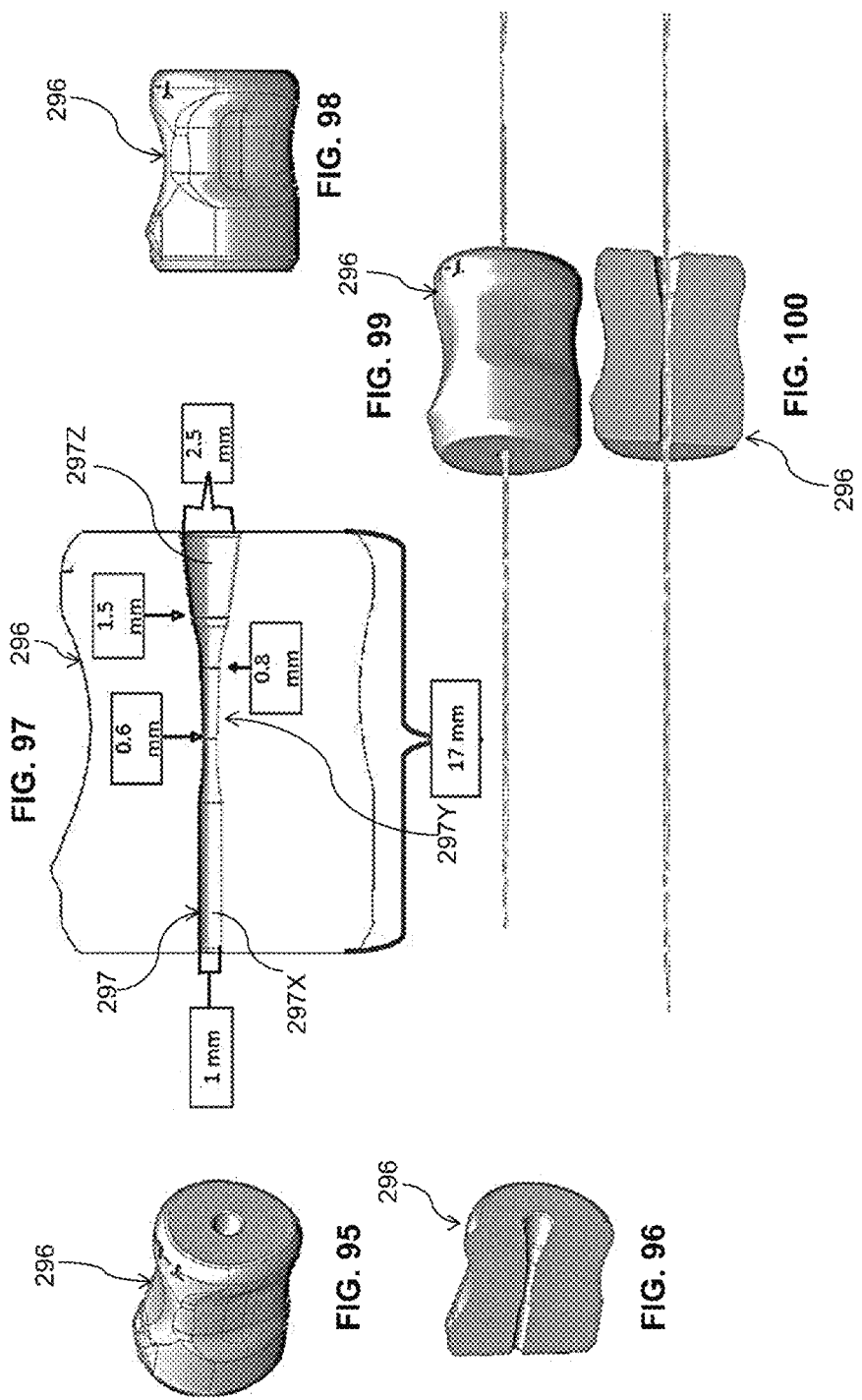

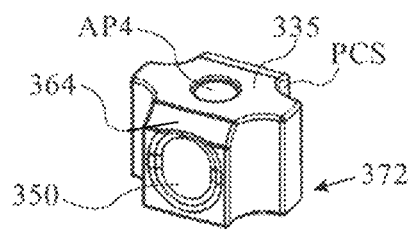
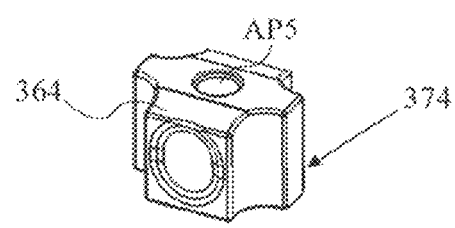
FIG. 113A  FIG. 114A
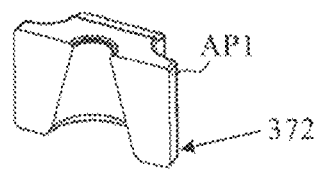
FIG. 113B  FIG. 114B
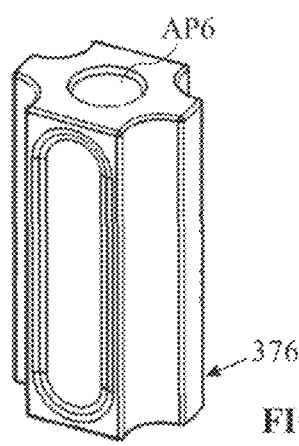
FIG. 115A
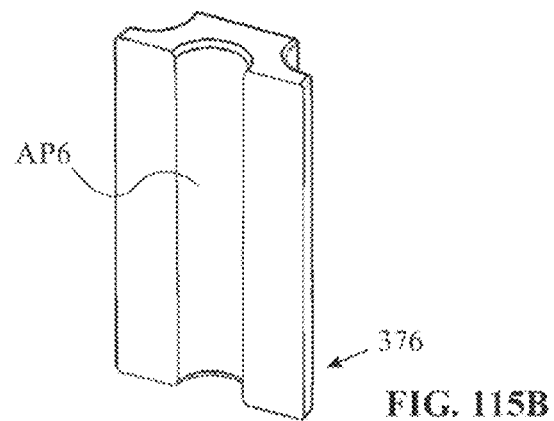
FIG. 115B

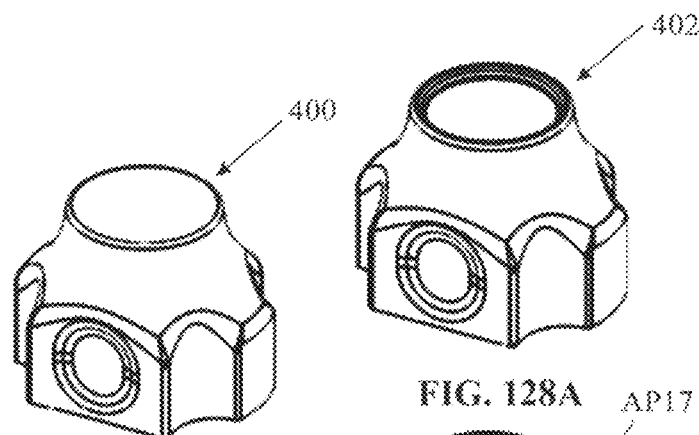
FIG. 127A
FIG. 128A
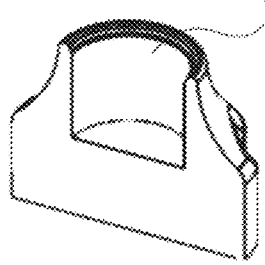
FIG. 128B
FIG. 127B
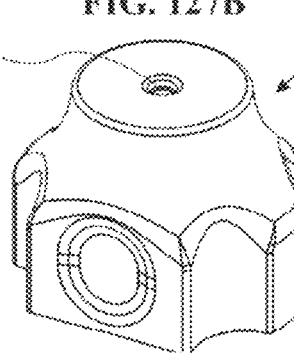
FIG. 129A
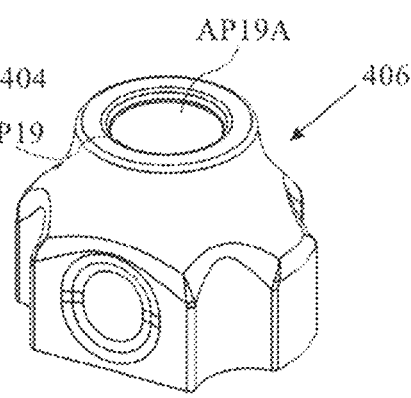
FIG. 129C
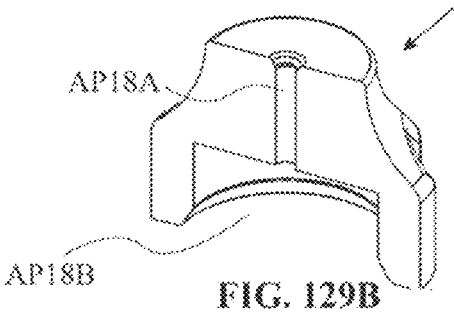
FIG. 129B
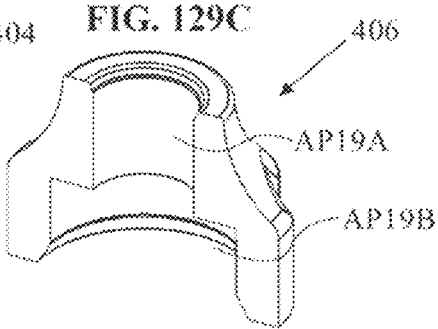
FIG. 129D

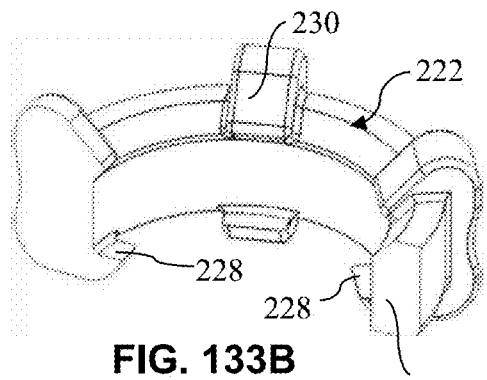
FIG. 133B
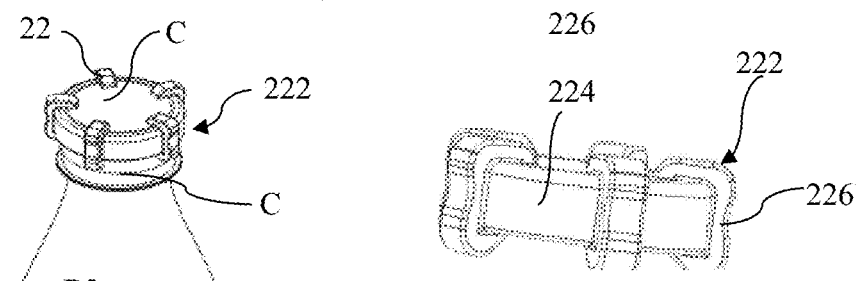
FIG. 133C
FIG. 133D
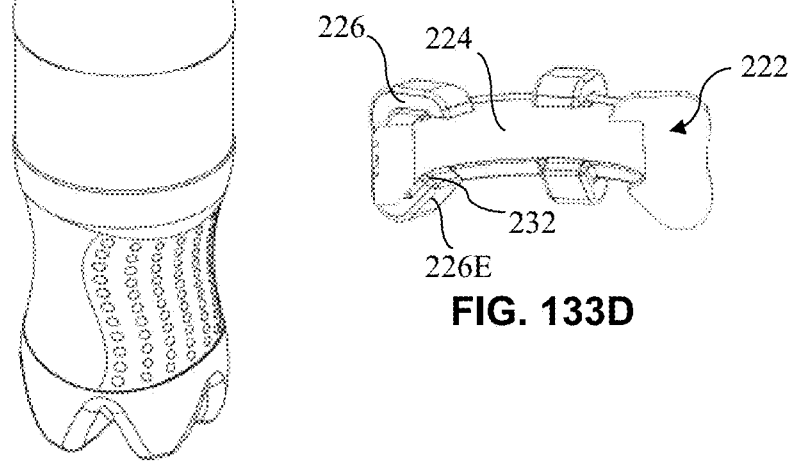
FIG. 133A
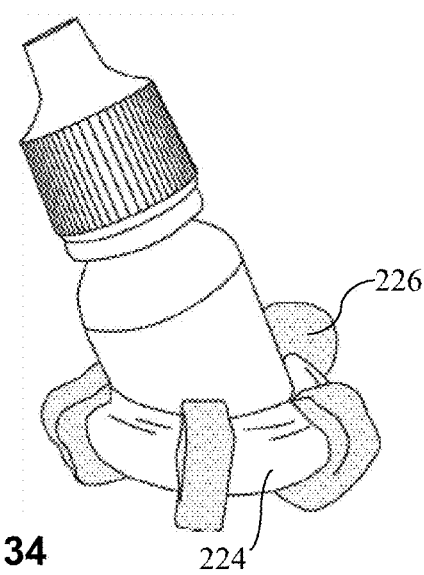
FIG. 134

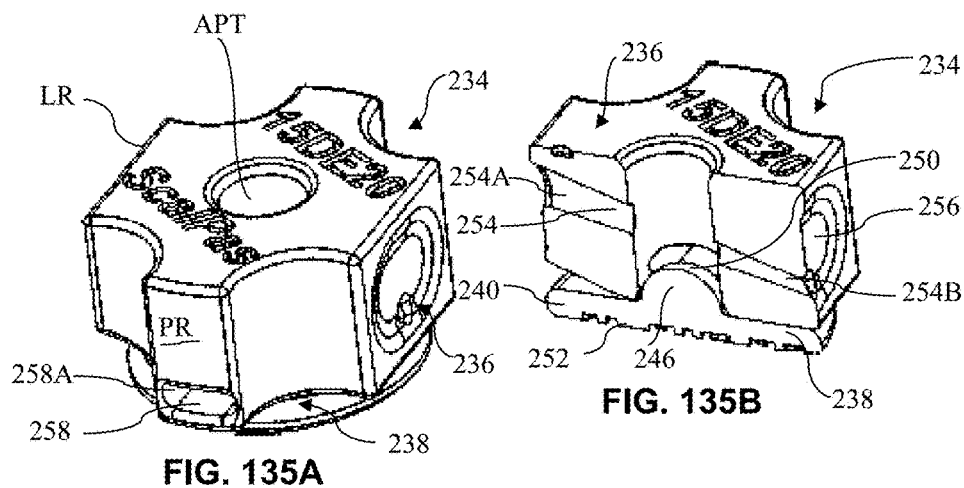
FIG. 135A
FIG. 135B
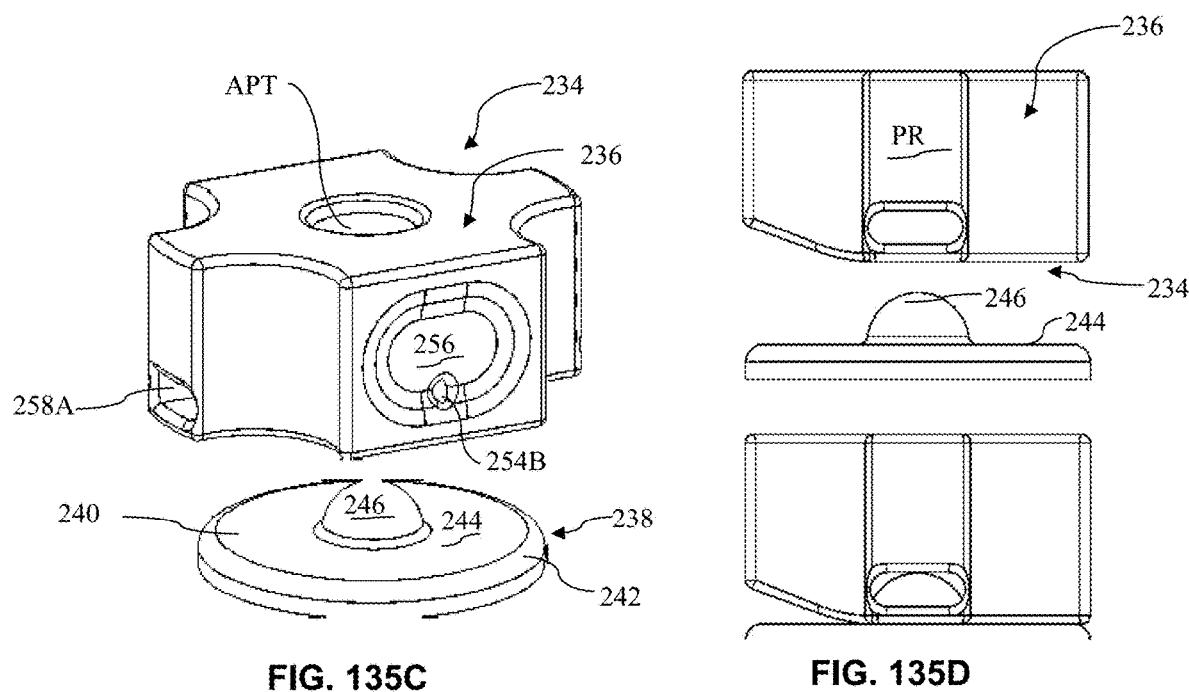
FIG. 135C
FIG. 135D

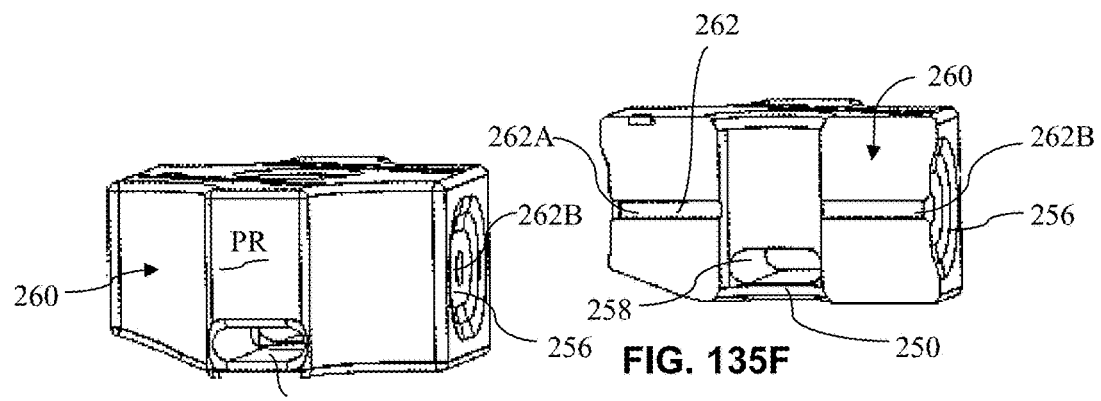
FIG. 135E     FIG. 135F
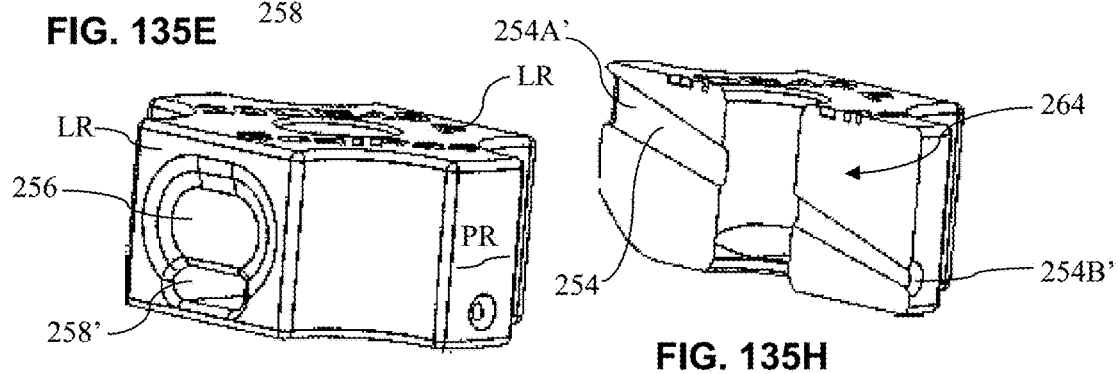
FIG. 135G     FIG. 135H
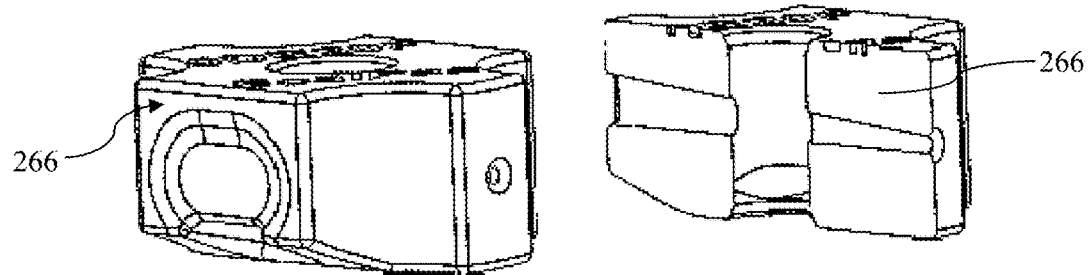
FIG. 135I     FIG. 135J

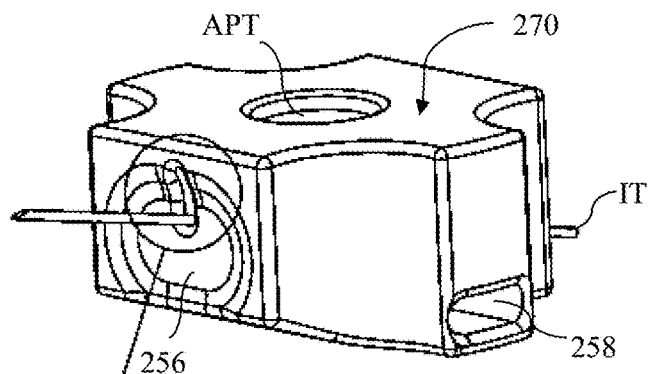
FIG. 137
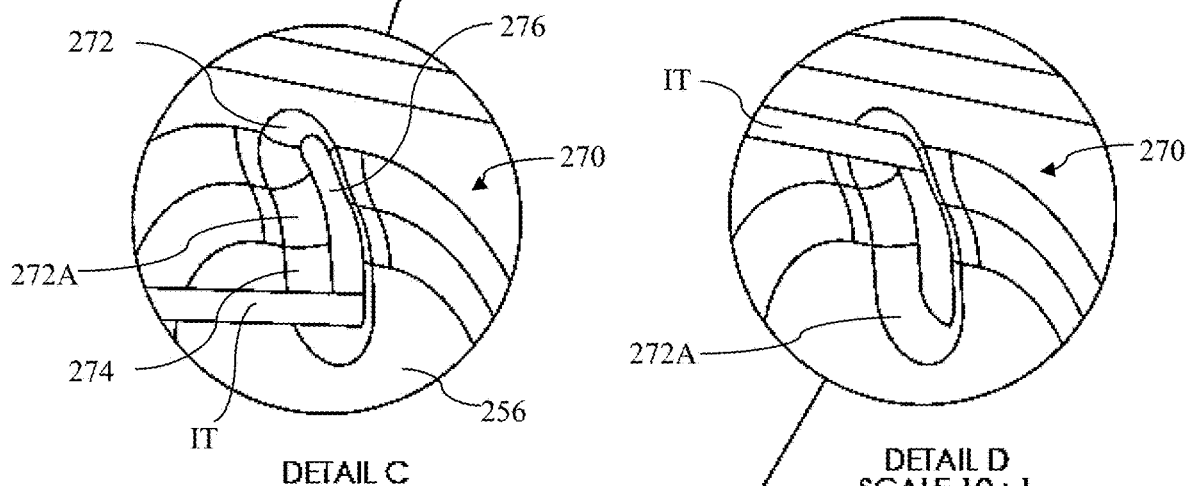
DETAIL C
SCALE 10 : 1
FIG. 137A
DETAIL D
SCALE 10 : 1
FIG. 138A
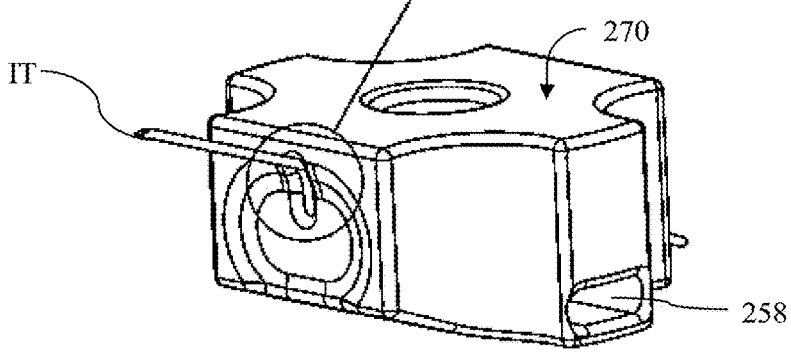
FIG. 138

FIG. 141A FIG. 141B

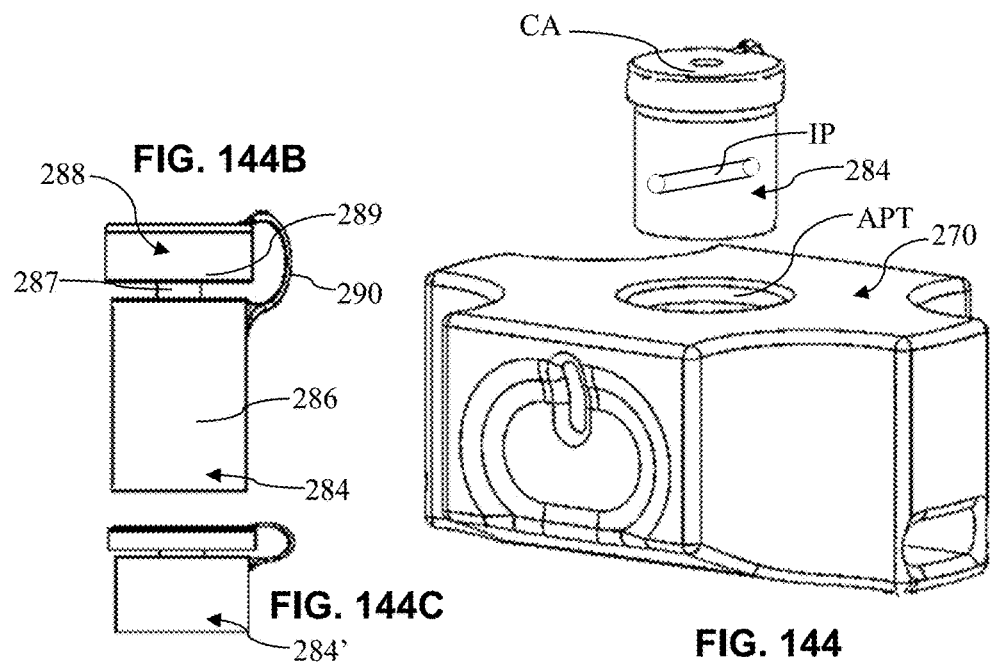
FIG. 144B
FIG. 144C
FIG. 144D
FIG. 144A
FIG. 144
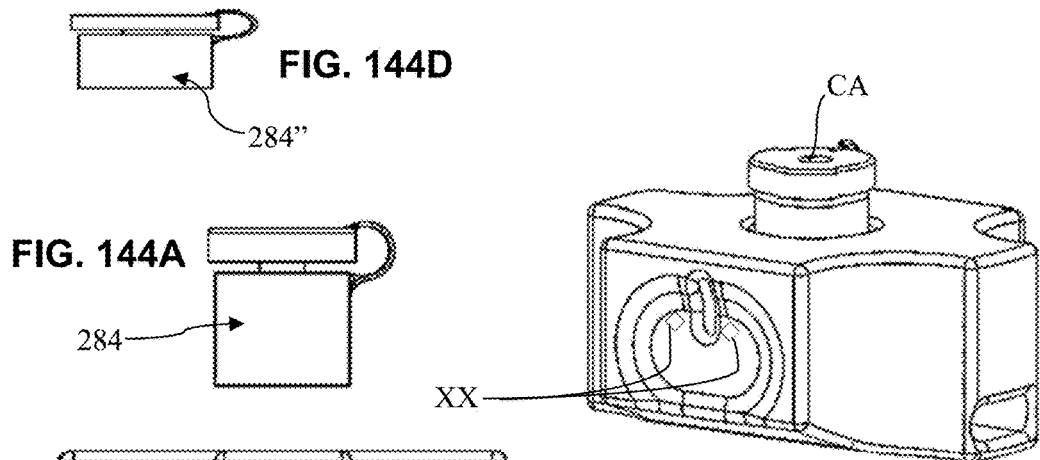
FIG. 145
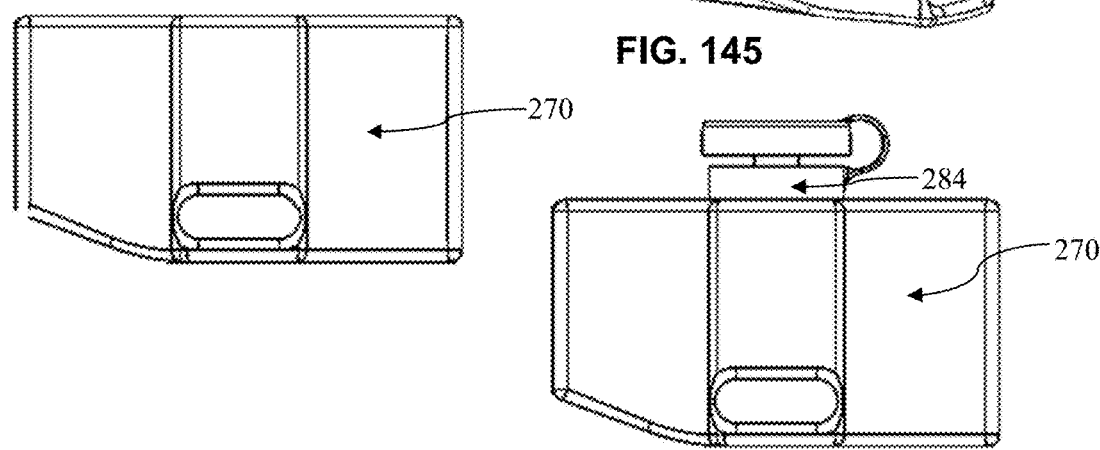
FIG. 145A

GRASPING FACILITATORS AND USES THEREOF AND KITS INVOLVING THE SAME

PRIORITY

The present invention claims priority to U.S. Provisional Patent Application Ser. No. 62/505,034; filed May 11, 2017, which is incorporated herein by reference in its entirety.

FIELD OF THE INVENTION

This invention relates to grasping facilitators, inclusive of utensil support mounts and adaptable collars either alone or in combination, with embodiments of such grasping facilitators being usable in the medical field.

BACKGROUND OF THE INVENTION

Various objects such as bottles (e.g., medical vials) are inherently unstable owing to their cylindrical geometry, which renders them prone to slip and roll. Likewise, if inadvertently tilted, they are apt to tip and spill their contents if open or insufficiently sealed. This is at best a nuisance but can be hazardous if the contents are chemicals or medicines. There are many different types of bottle supports, some of which are intended to address these issues.

US 2012/0241332 discloses a multipack carrier for bottles, cans, or jars having a plurality of plastic braces each comprising a circular cutout for a accommodating the neck of the bottle and a plurality of internal webs in the plane of the cutout that are flexed and resiliently grasped by the bottle neck. The device is used to carry multiple bottles but does not support them from falling or tipping over when disposed on a flat surface.

US 2010/0140431 discloses a bottle support comprising a cylindrical ring and a plurality of internal webs mounted parallel to an axis of the ring and each fixed to an inside surface thereof. The webs are flexed radially and resiliently grasped by the bottle neck for supporting an inverted container on a flat surface. Although this device will support a bottle disposed on a flat surface, it requires that all the webs are flexed equally and this militates against supporting a bottle at an angle.

In addition to the need to support bottles of different sizes on a flat surface, there is also a need to lift and hold bottles securely. FIGS. 1a, 1b, 1c and 1d show pictorially the tendency for round and cylindrical objects 10 to slip when grasped between thumb 11 and forefinger 12. When a gripping force is applied as shown in FIG. 1c between points on the side surfaces of a cylindrical object 10 that are not diametrically opposite each other, a component of the gripping force acts to push the object out of the user's grip. This tendency is increased if friction between the user's fingers and the outer surface of the object is reduced, such as when a bottle is gripped with wet or soapy hands. This tendency to slip from the user's grip is equally true for bottle supports of the type described in above-mentioned US 2010/0140431 owing to the smooth side surface of the cylindrical ring.

FIGS. 2a and 2b show pictorially a bottle 10 gripped non-diametrically between the thumb 11 and forefinger 12 of a user's hand. If the segment that is closer to the center 13 of the oblique arch between thumb and forefinger and bound by the points at which the bottle is gripped has an area less than half that of the bottle's cross-section, the gripping force will have a tangential component that urges the bottle away from the center 13 of the oblique arch. The bottle 10 will then slip out of the user's hand. Conversely, if the area of this segment is greater than half that of the bottle's cross-section, the gripping force will have a tangential component that urges the bottle toward the center 13 of the oblique arch into the user's hand. In either case, the transverse grip on the bottle will be lost and the bottle will slip.

The need to support bottles stably becomes all the more urgent when the bottles contain medicines and other liquid contents that are required to be removed or injected. For example, liquid medicine bottles are often provided with a resealable cap through which a hypodermic needle is inserted in order to withdraw a quantity of liquid. Alternatively, liquid in a hypodermic syringe may need to be injected into a vial or other container. Both of these operations require that the vial or bottle be retained securely on a support surface, possibly inclined to the horizontal, in order to provide direct access to the cap and ensure visual alignment thereof to the tip of the hypodermic needle.

There is therefore a need for a device that allows the bottle to be disposed stably on a support surface while allowing it to be gripped securely and reliably without the associated risk of slippage, particularly when gripped using wet hands.

In addition to the problem of rolling and tilting of bottles and the like, there is another and in some respects associated problem of handling bottles securely when filling them or extracting liquids therefrom. This problem may at first seem quite dissociated from the stability issues that we have raised above, but frequently the very act of injecting liquid into a bottle or extracting liquid therefrom is what induces instability in the first place.

Thus, liquids may be extracted from bottles such as medicine vials or injected therein in one of two ways, which we will describe with reference to a typical medical scenario. In one way, the bottle is placed on a work surface and the needle of a hypodermic syringe is inserted into the neck of the bottle. Provided that the only force applied is vertical, this should avoid any tendency to skid. But in practice, this is difficult to achieve. Medical orderlies work under pressure and work surfaces are often wet, so that any slight displacement of the needle from the vertical induces a horizontal force component that causes the bottle to slip. Alternatively, the bottle is gripped in one hand by or toward the neck and the hypodermic syringe is operated with the other hand. Not infrequently this is done with wet hands or gloves and this causes the bottle or vial to slip from the user's grip in the same manner as explained above with reference to FIGS. 1 and 2 of the drawings. Furthermore, this technique requires axial alignment between the tip of the needle and the neck of the bottle. Under stress it is all too easy to miss the bottle and the exposed fingers of the user's other hand are then at risk of being pricked and possibly injected with the contents of the hypodermic syringe.

The tendency of bottles to slip from a user's grip has been addressed in the art. For example, CN 2010/23742 discloses a bottle sheath disposed between the neck and the middle portion of a bottle and fixed to the bottle body. WO 2010/037250 discloses a non-slip sleeve that is removably fitted around the neck of a bottle. US 2008/0179353 discloses a sleeve that is secured around the neck of a wine bottle for preventing dripping when pouring.

None of these references discloses a non-slip sheath that may be removably attached to the neck of a bottle and is configured to coupling to a hypodermic syringe.

The invention also addresses a number of problems associated with handling of hypodermic syringes and other medical utensils such as specimen vials (e.g., blood specimen vials), catheters, and the like. First, relative to hypodermic syringes, the sharp needle is a common source of injury to both patient and medical staff Initially the needle is protected by a guard, which must be removed prior to use often under conditions that may be stressful for the patient. A patient who wriggles increases the risk that the medical orderly will inject the needle poorly, thus causing hardship to the patient; and will more easily render the medical orderly prone to self-injury. Hypodermic needles are typically injected into a blood vessel at an acute angle to the surface of the skin of, for example, about 15° or vertically at 90°, although they may be injected at other angles. For example, due to the relationship of different sized fingers, the angle of penetration will vary. However, by placing a predetermined angle on a sleeve one can standardize the angle desired despite different operator hand size (e.g., a pre-chosen and fixed needle insertion angles of 15°, 20°, or 40° within the 15° to 90° options noted above).

The manner of use typically requires use of both hands as shown in FIG. 2c. Alternatively, one hand may be used to hold the syringe and manipulate the plunger while a finger of the other hand is placed under the body of the syringe and serves as a fulcrum or pivot point that allows the medical orderly to guide the syringe at the appropriate angle with more control than could be achieved using only one hand. In either case, the close proximity of the other hand to the syringe renders it subject to self-injury, particularly if the patient moves unexpectedly.

Further problems relate to the extent to which the needle projects from the end of the syringe. Generally, the length of the needle determines the maximal depth of penetration, which itself is a function of the medical procedure. In other words, some procedures may require only superficial penetration while others may require that the needle be injected to a depth of over one-inch i.e. more than 2.5 cm. The longer the needle, the higher is the risk of injury and the more frightening it is to the patient. This is why patient management often dictates that the needle guard be removed out of sight of the patient and that the needle not be brandished in the sight of the patient. But regardless of when the needle guard is removed, the needle must be exposed prior to use and it is during this exposure that the medical orderly is most at risk of self-injury.

Another common source of injury occurs when lifting a hypodermic syringe from a supine position. During medical procedures, a nurse typically hands the surgeon a tray on which there are disposed multiple instruments for carrying out the procedure and from which the surgeon selects the appropriate instrument. The hands of the surgeon may be wet and a hypodermic syringe being cylindrical can easily slip from the surgeon's grip. It should be borne in mind that optimal gripping is always achieved by the arch between thumb and forefinger, as explained above with reference to FIG. 2a. This is how screwdrivers, for example, are gripped in a manner that allows adequate torque to be applied. However, hypodermic syringes are not amenable to being grasped in this manner, and in practice a medical orderly is constrained to lift them using only his or her finger tips, thus vastly increasing the likelihood of slippage and self-injury. Also, the cylindrical barrel and plunger of a standard prior art syringe have end flanges that present obstacles relative to controlled holding and passing of syringes. The present invention provides for the removal of either or both of the plunger and barrel flanges with their replacement being a grasping device much more user friendly.

SUMMARY OF THE INVENTION

One object of the present invention is to provide an improved bottle support that allows bottles to be supported by either their base or their neck and to be retained in the bottle support at an angle without detracting from the stability of the support.

Another object is to address and alleviate some of the aforementioned problems relating to safe transfer of liquid from a bottle to another container, particularly albeit not only to hypodermic syringes.

Yet a further object is to address and alleviate some of the aforementioned problems relating to use of hypodermic syringes and other needed utensils.

To this end there is provided in accordance with the invention a bottle support and a collar having the features of the respective independent claims.

In some embodiments the bottle support comprises: an annular core having an inner side surface defining a hollow opening, an outer side surface, a top surface and a base surface, and a plurality of pliable ribs each at least partially encircling the annular core so as to overlap the base surface, the top surface and the outer side surface such that at least an upper end of each rib where it overlaps the top surface extends into the hollow opening.

The ribs are mounted parallel to a longitudinal axis of the core but unlike the arrangement in US 2010/0140431 they cover at least partially the outer surface and project over the top surface. Furthermore, they extend into the hollow opening so as to be resiliently deformed by a bottle inserted therein and thereby grasp the bottle.

In some embodiments, the lower ends of the ribs extend into the hollow opening so as to provide a platform for supporting the base of the bottle and ensuring that it does not make direct contact with a surface on which the bottle support is disposed. This prevents contamination reaching a sterile bottle. Further, the mounts of the present invention can also be used on upper regions of objects either to facilitate grasping of the object in that area or in conjunction with an objects position retention with the mounts vertical orientation being switchable to place ribs in either an underlying support orientation or an overlying clamping type orientation or both orientations through a pair of mounts working together.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1a to 1d show schematically the tendency of a cylindrical bottle to slip when gripped non-diametrically;

FIGS. 4a and 4b show pictorially a cylindrical bottle supported within the bottle support of FIG. 3a;

FIGS. 10a and 10b show a detail of the collar according to a first embodiment;

FIG. 11 shows a detail of the collar according to a second embodiment;

FIG. 12 shows pictorially use of the collar when transferring liquid between the bottle and a hypodermic syringe;

FIGS. 13 and 14 show different uses of the bottle support to reduce the risk of self-injection or damage when transferring liquid between the bottle and a hypodermic syringe;

FIGS. 32a and 32b show a top plan view of the components of FIG. 31 separated.

FIG. 33 shows the pliable annular core mount in supporting fashion at the base of a different utensil in the form of a bottle with a quadrilateral periphery.

FIG. 52 shows a front perspective view of the crush collar shown in FIG. 51.

FIG. 53 shows a cross-sectional view of that which is shown in FIG. 52.

FIG. 54 shows a perspective view of the horn ended collar shown in FIG. 19 with additional grasping collar enlarged portions provided on the syringe's cylinder and the plunger base, respectively.

FIG. 55 shows a side view of an alternate horn collar embodiment to that which is shown in FIG. 54.

FIG. 74 shows the components of FIG. 73 in an engaged state and with the same offset, two finger grasping described above.

FIG. 75 shows the combined components of FIG. 74 and the ability for the pinch support to hold the combination in a suspended state with one hand.

FIG. 76 shows a modified tray embodiment featuring a reception aperture that has a common surrounding configuration for snug receipt of the integrated collar shown in the syringe plunger of FIG. 48.

FIG. 77 shows the integrated collar and plunger shown in FIG. 48 in a snug reception state relative to a supporting/transfer tray.

FIG. 87 shows a cross section of the collar in FIG. 86.

FIG. 88 shows a cross-sectional view from the opposite direction from that which is shown in FIG. 86.

FIG. 89 shows the grasping collar of FIG. 86 in three different positions on a catheter line and with the middle position showing being cut away to illustrate the haptic, generally sinusoidal wave pattern of the through-hole cavity featured for the sleeve which has different clearance widths along the length as well as different outlet opening diameters in this embodiment.

FIG. 90 shows the intermediate positioned grasping collar presented in FIG. 89 in an expanded view such that the haptic promoting cavity configuration can be better seen together with some, non-limiting, illustrative cavity thickness values of the length of the collar for the catheter equipment embodiment featured.

FIG. 91 shows an alternate embodiment of a catheter line grasping collar or sleeve with its central haptic cavity shown in cross-section.

FIG. 92 shows the cross-sectional view of FIG. 91 with some non-limiting, illustrative haptic cavity diameter values relative to the varying diametrical nature of the cavity along its length.

FIG. 93 shows a front elevation of the exterior contoured surface of the collar of FIG. 91.

FIG. 94 shows the collar of FIG. 91 in position on a catheter line.

FIG. 95 shows an additional embodiment of a catheter line grasping collar or sleeve in perspective view.

FIG. 96 shows the grasping collar of FIG. 95 with its central haptic cavity shown in cross-section.

FIG. 97 shows the cross-sectional view of FIG. 96 with some non-limiting, illustrative haptic cavity diameter values relative to the varying diametrical nature of the cavity along its length.

FIG. 98 shows a front elevation of the exterior contoured surface of the collar of FIG. 95.

FIG. 99 shows the collar of FIG. 95 in position on a catheter line with an exterior view.

FIG. 100 shows the collar of FIG. 95 in position on a catheter line with a cut away view showing the haptic cavity contact with the threaded catheter line extending therethough.

FIG. 101c showing a top plan view, and FIG. 101d showing the cavity configuration extending through the collar at an angle.

FIG. 102c showing a top plan view, and FIG. 102d showing the cavity configuration extending through the collar at an angle.

FIG. 106b showing a pinching holding of just the tool body;

FIGS. 107a and 107b show different views of the combination of FIG. 106a, while FIG. 107c shows a one hand holding of all components but with the base collar removed, FIG. 107d shows a single hand support of the combination in ready for non-rotative use position, while FIG. 107e shows the combination of FIG. 106a with an added adapter component received by the removed base collar.

FIGS. 112a and 112b illustrate a longer or thicker version of the collar configuration of FIG. 10a with the former showing a perspective view and the latter showing a central vertical cross-section and the aperture configuration.

FIGS. 113a and 113b illustrate a longer or thicker version of the collar configuration of FIG. 10a with the former showing a perspective view and the latter showing a central vertical cross-section and the aperture configuration.

FIGS. 114a and 114b illustrate a longer or thicker version of the collar configuration of FIG. 10a with the former showing a perspective view and the latter showing a central vertical cross-section and the aperture configuration.

FIGS. 115a and 115b illustrate a much longer or thicker version of the collar configuration of FIG. 10a with the former showing a perspective view and the latter showing a central vertical cross-section and the aperture configuration.

FIGS. 116a and 116b illustrate a longer or thicker version of the collar configuration of FIG. 10a with the former showing a perspective view and the latter showing a central vertical cross-section and the aperture configuration.

FIGS. 117a and 117b illustrate a longer or thicker version of the collar configuration of FIG. 10a with the former showing a perspective view and the latter showing a central vertical cross-section and the aperture configuration.

FIGS. 118a and 118b illustrate a longer or thicker version of the collar configuration of FIG. 10a with the former showing a perspective view and the latter showing a central vertical cross-section and the aperture configuration.

FIGS. 119a and 119b illustrate a longer or thicker version of the collar configuration of FIG. 10a with the former showing a perspective view and the latter showing a central vertical cross-section and the aperture configuration.

FIGS. 120a and 120b illustrate a longer or thicker version of the collar configuration of FIG. 10a with the former showing a perspective view and the latter showing a central vertical cross-section and the aperture configuration.

FIGS. 121 and 121b illustrate a longer or thicker version of the collar configuration of FIG. 10a with the former showing a perspective view and the latter showing a central vertical cross-section and the aperture configuration.

FIGS. 122a and 122b illustrate a longer or thicker version of the collar configuration of FIG. 10a with the former showing a perspective view and the latter showing a central vertical cross-section and the aperture configuration.

FIGS. 123a and 123b illustrate a longer or thicker version of the collar configuration of FIG. 10a with the former showing a perspective view and the latter showing a central vertical cross-section and the aperture configuration.

Figures 124A, 124B:
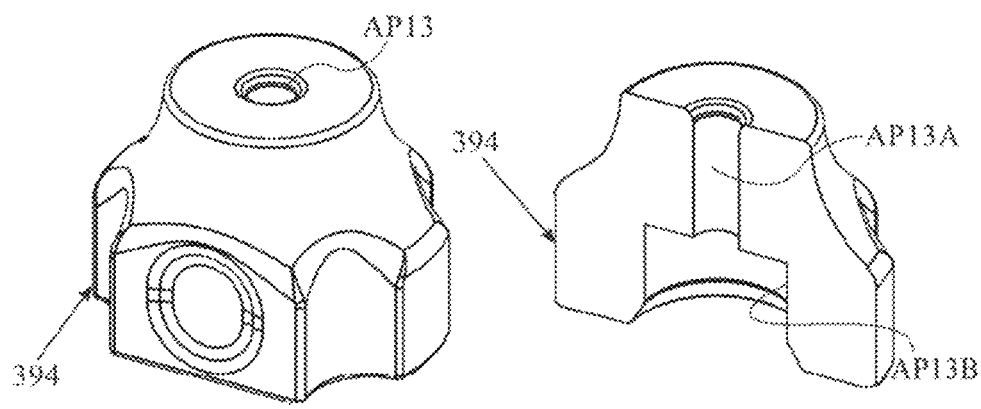

FIGS. 124a and 124b illustrate a version of the collar configuration of FIG. 11 with the former showing a perspective view and the latter showing a central vertical cross-section and the stepped aperture configuration.

Figures 125A, 125B:
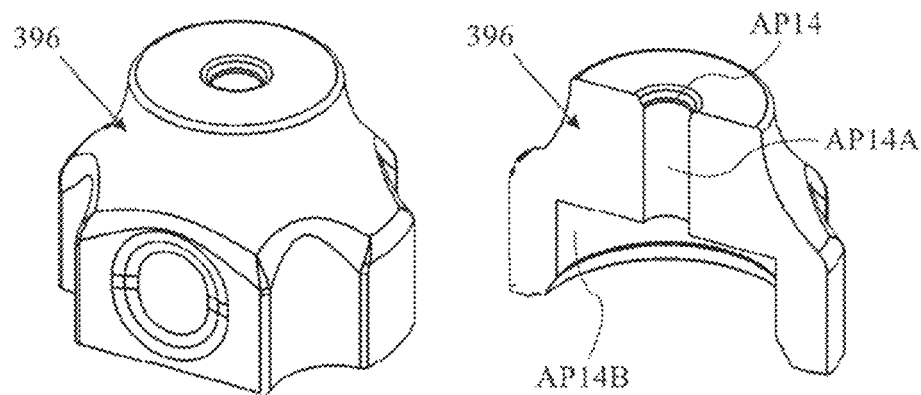

FIGS. 125a and 125b illustrate a version of the collar configuration of FIG. 11 with the former showing a perspective view and the latter showing a central vertical cross-section and the stepped aperture configuration.

Figures 126A, 126B:
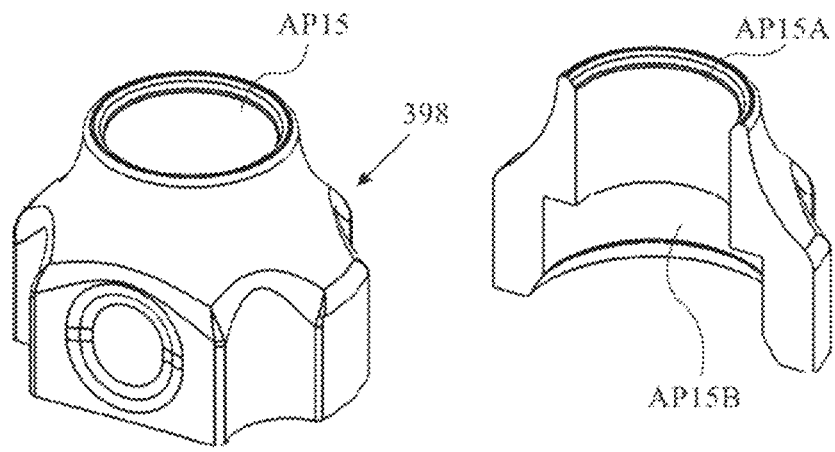

FIGS. 126a and 126b illustrate a version of the collar configuration of FIG. 11 with the former showing a perspective view and the latter showing a central vertical cross-section and the stepped aperture configuration.

FIGS. 127a and 127b illustrate a closed top version of the collar configuration of FIG. 11 with the former showing a perspective view and the latter showing a central vertical cross-section and the aperture configuration.

FIGS. 128a and 128b illustrate a closed bottom version of the collar configuration of FIG. 11 with the former showing a perspective view and the latter showing a central vertical cross-section and the aperture configuration.

FIGS. 129a and 129b illustrate a version of the collar configuration of FIG. 11 with the former showing a perspective view and the latter showing a central vertical cross-section and the stepped aperture configuration.

FIGS. 129c and 129d illustrate a version of the collar configuration of FIG. 11 with the former showing a perspective view and the latter showing a central vertical cross-section and the stepped aperture configuration.

Figure 3A:
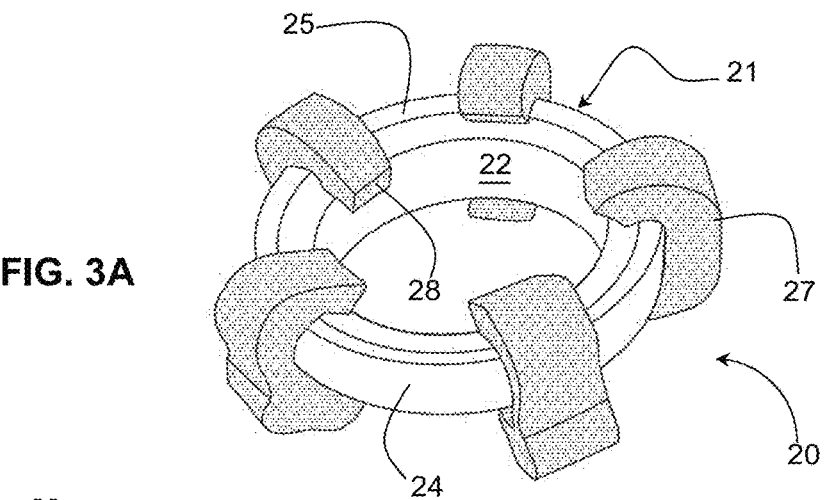
FIGS. 3a, 3b and 3c show pictorially details of a bottle support according to an embodiment of the invention.
Figure 130A:
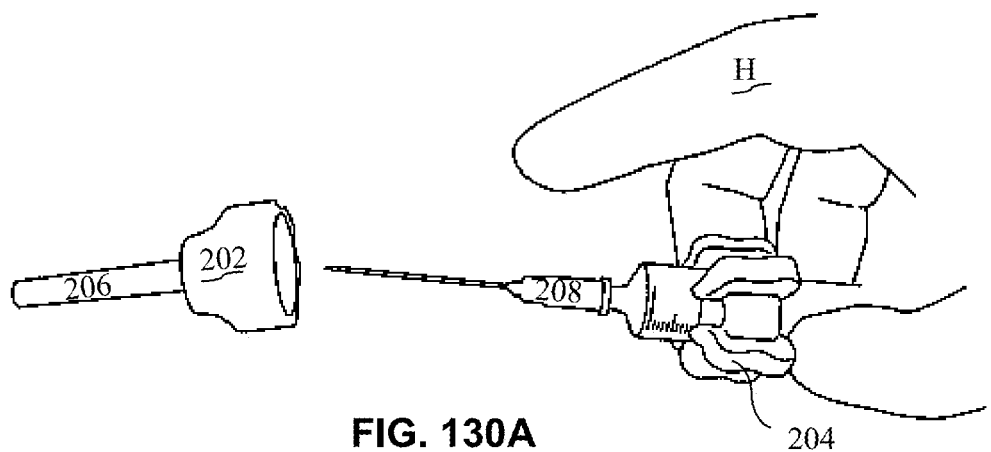
Figure 130B:
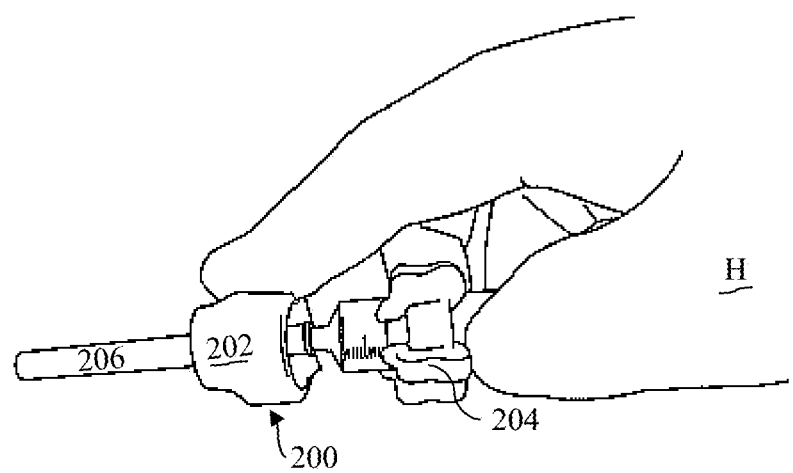
Figure 130C:
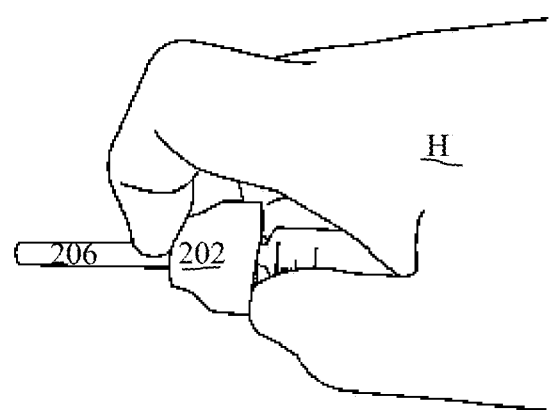

FIGS. 130a to 130c, provide an example of a combination collar of FIG. 11 and mount of FIG. 3a being used to hold a needle cover in position for safe insertion of the needle into the needle cover and to snap on with one hand the needle cover through use of the combination, with FIG. 130b also showing an alternative initial stage of separation of the two with one hand.

Figure 131A:
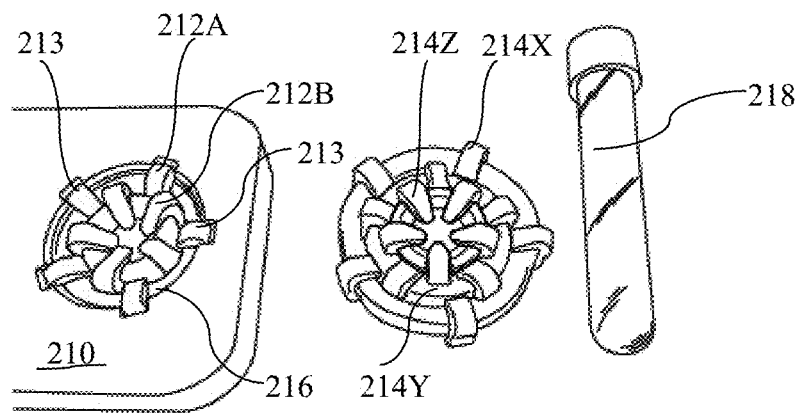
Figure 131B:
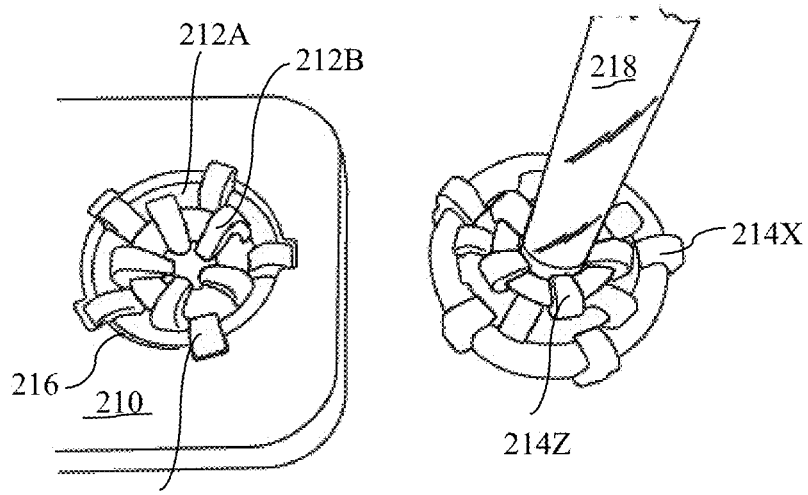
Figure 131C:
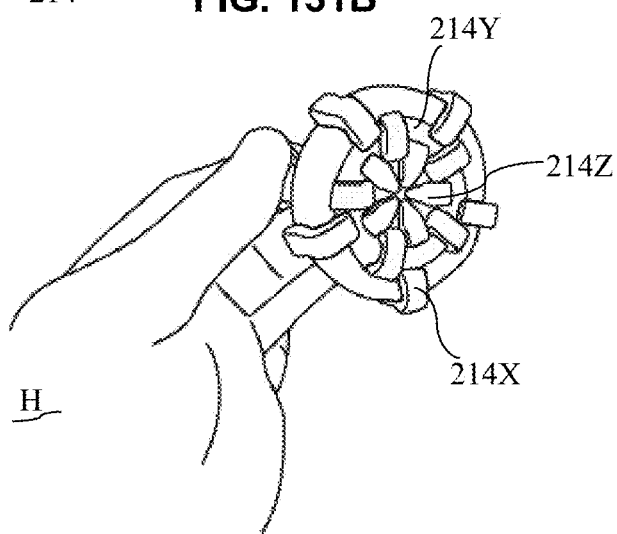

FIGS. 131a to 131c show a circumferential set of different size mounts of FIG. 3a configuration used to adjust the size of a tray aperture (e.g., see FIG. 39 example tray) such that a smaller utensil can fit in a larger aperture, and also to provide a more stable (larger diameter contact with support) as when the combination is put on a vibrating plate or surface to avoid specimen settling or coagulation.

Figure 132A:
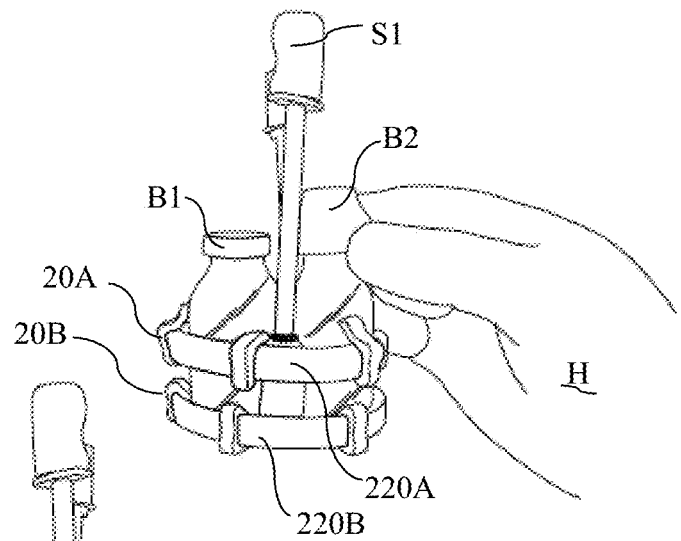
Figure 132B:
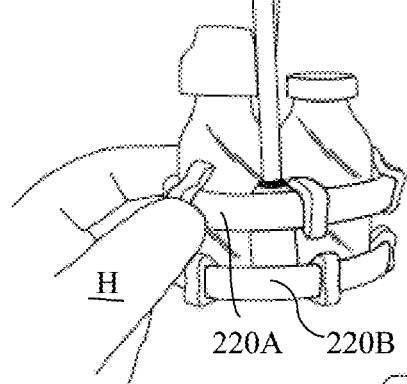
Figure 132C:
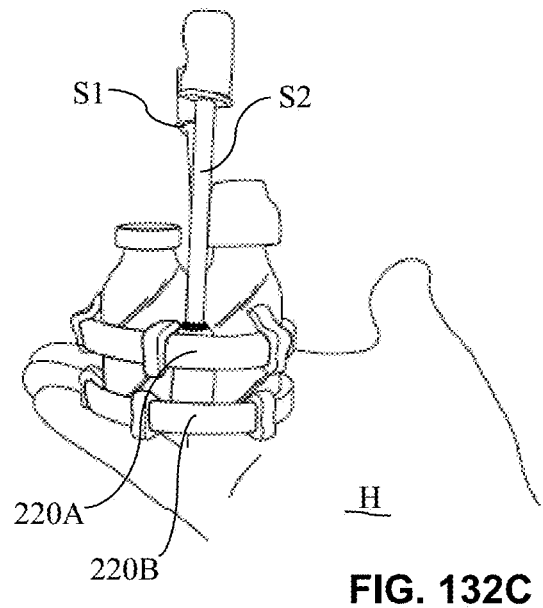

FIGS. 132a to 132c show a double set kit of same size mounts of the configuration of FIG. 3a used to hold together a plurality of different components to provide for transport with one hand, either by holding one of the more upper regions of the trapped components (132a), holding one or more of the mounts (FIG. 132b); or holding the bottom region of the trapped components (FIG. 132c).

FIGS. 133a to 133d show the mount of FIG. 3a configuration mounted on a cap of a bottle such as a soda bottle, with cross-sectional views showing how the mount mounted on the cap of the bottle has an annular core and ribs designed for bottle cap engagement.

FIG. 134 shows a view of a pliable mount of FIG. 3a configuration which is able to accommodate a large tilt due to missed insertion of a medicine dropper bottle or an intentional tilted orientation for presenting the top at a more desired orientation to the user.

FIGS. 135a to 135j illustrate various views of an alternate combination of features of the invention featuring a collar having FIG. 10a configuration with added side porting, with FIGS. 135a to 135d showing the turret combination of collar and underlying spin platform, and 135e to 135j showing the turret collar alone in various perspective and cut-away views.

Figure 136A:
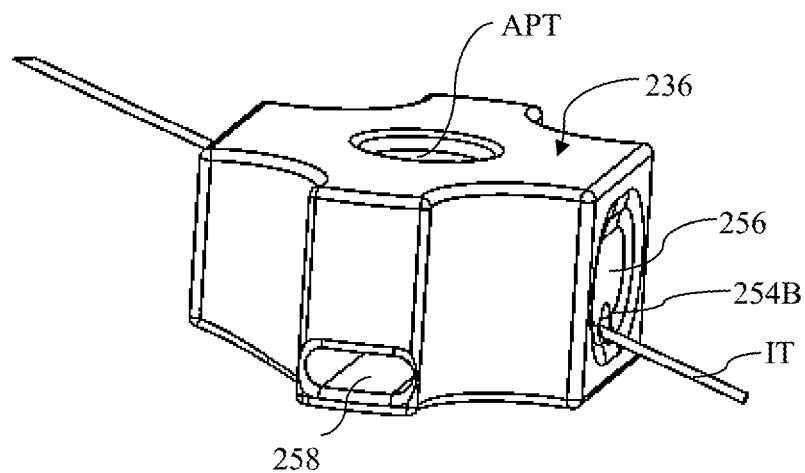
Figure 136B:
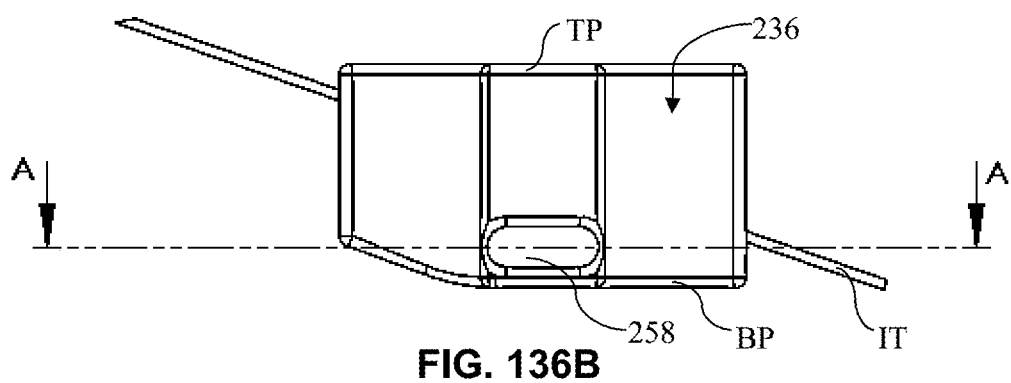
Figure 136C:
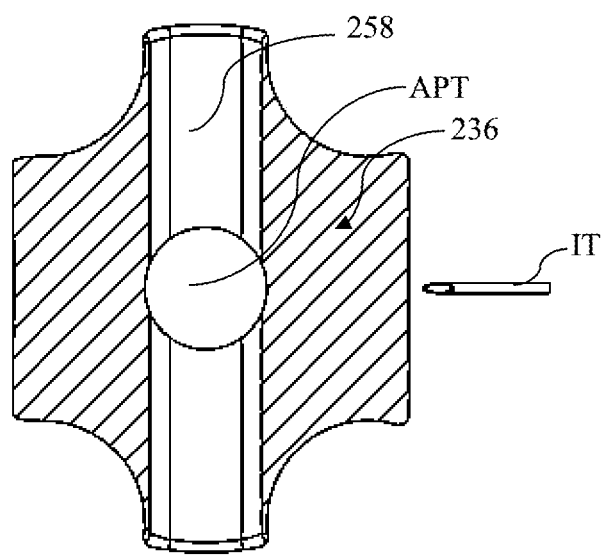

FIGS. 136a to 136c illustrate the collar of FIG. 135a removed from its mount, with FIG. 135a showing a perspective view of the collar with an angled thin tool inserted as in a needle insertion, catheter sheath, wire, fluid tube, etc. insertion, FIG. 135b shows a front elevational view of that which is shown in FIGS. 135a, and 135c shows a cross-sectional view along cross-section A-A in FIG. 135b.

FIG. 137 shows a rotated view of the collar shown in FIG. 135a and with the inserted tool being at a shallower angle relative to the underlying surface of the collar such that it rests in the lower part of the illustrated oblong exit (or entry groove) that is detailed in the enlarged view shown in FIG. 137A which shows an enlarged view of the circled section of FIG. 137.

FIG. 138 shows a rotated view of the collar shown in FIG. 135a and with the inserted tool being at a steeper angle relative to the underlying surface of the collar such that the tool (e.g., sheath) abuts the upper part of the illustrated oblong exit (or entry groove) that is detailed in the enlarged view shown in FIG. 138A which shows an enlarged view of the circled section of FIG. 138.

Figure 139:
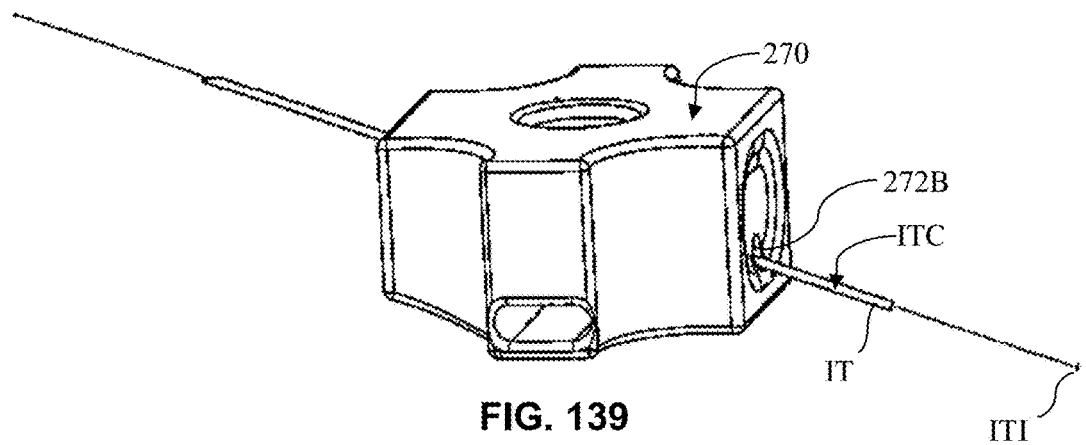

FIG. 139 also shows a rotated view of the collar shown in FIG. 135a and with the inserted tool being a combination sheath and interior wire, with the collar providing the desired angle of orientation.

Figure 140:
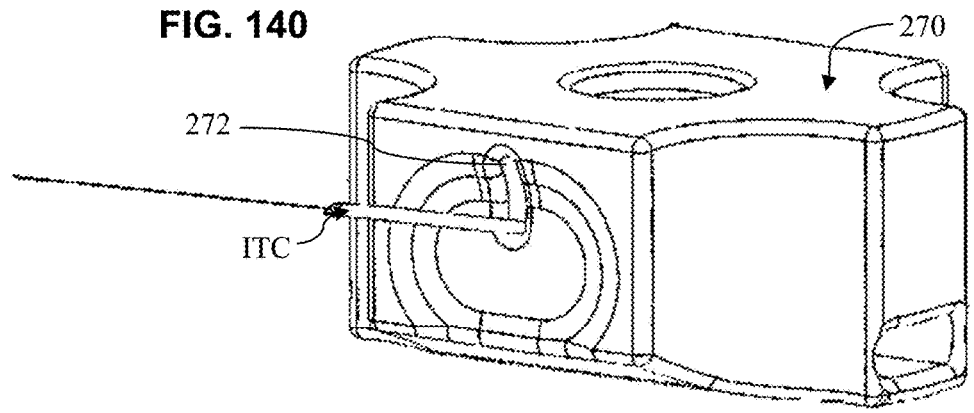

FIG. 140 shows the collar of FIG. 139 with inserted sheath and wire tool received but from a different angle.

Figure 141C:
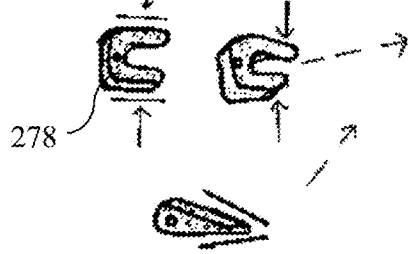
Figure 141:
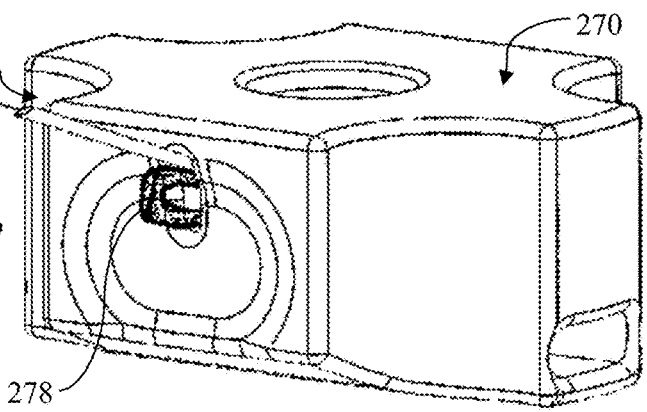

FIG. 141 shows a similar view as that of FIG. 140 but with a position retainer insert added. FIGS. 141a to 141c show different variants of the position retainer insert designed to hold the tool at a desired orientation within the receiving oblong or oval shaped opening provided in the collar for tool positioning flexibility.

Figure 142A:
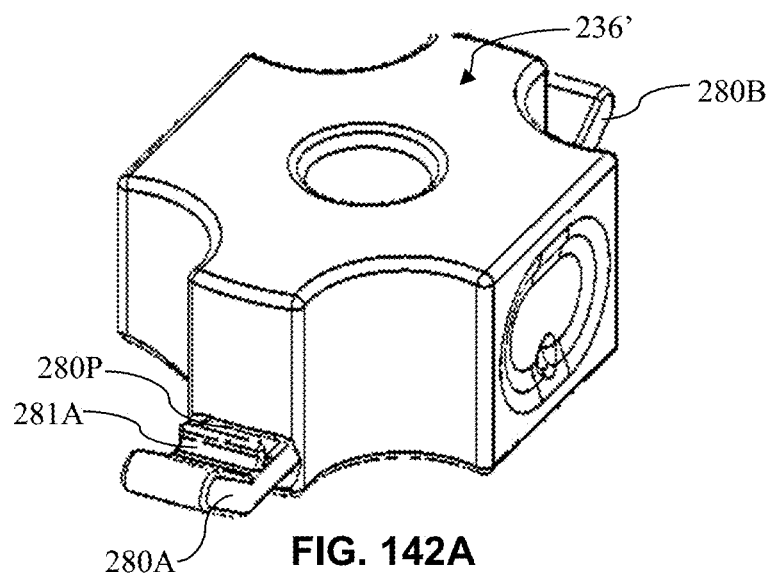
Figure 142B:
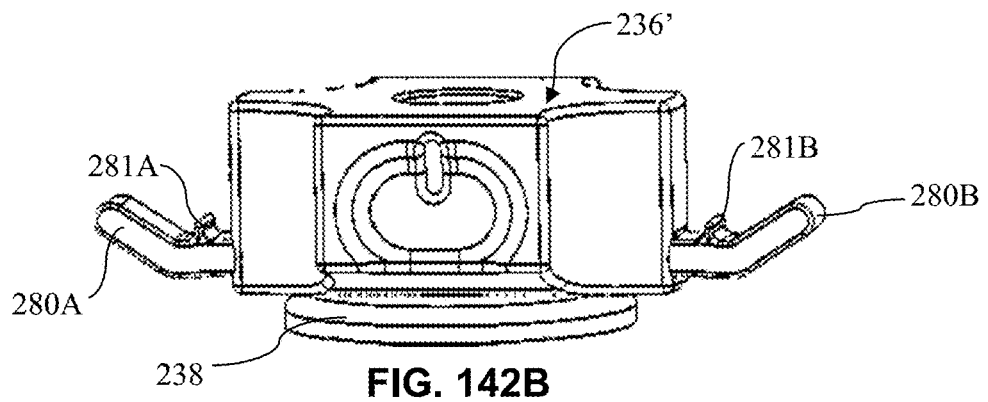

FIGS. 142a and 142b show different views of a swivel mounted collar similar to FIG. 135a, but with a pair of clamp down wings extending out from the collar main body (e.g., after insertion into respective passageway sections of the turret collar).

Figure 143:
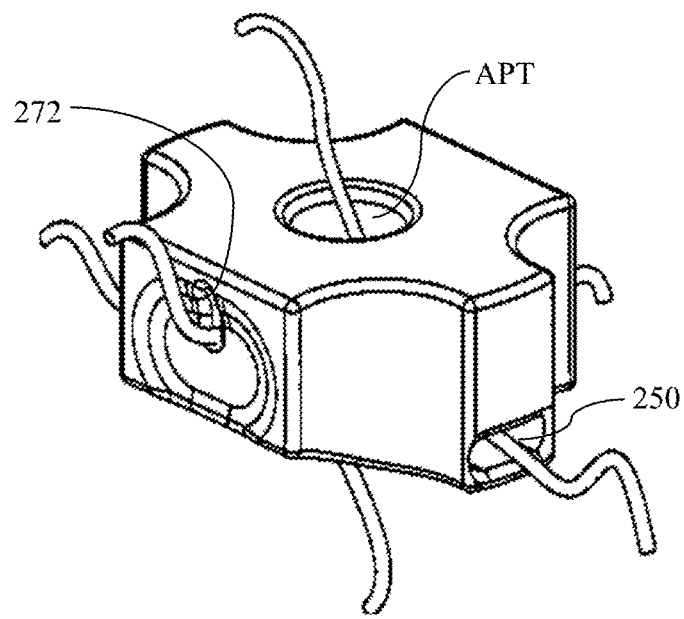

FIG. 143 shows a swivel mounted collar similar to FIG. 135a with a plurality of different utensils or one utensil having a plurality of different offshoots (e.g., instrument wiring or tubing) received therein and coming out of the different porting.

FIG. 144 illustrates the collar of FIG. 135 further comprising a plug member having a central aperture, which plug provides for hold down functioning of items received in the collar and/or alignment for needle insertion etc., relative to a central hole in the plug, and or deflecting a received thin instrument as to brake from further movement or stop flow in valve stop like fashion.

FIG. 144a shows the collar and plug arrangement shown in FIG. 144 but from a side view.

FIGS. 144b to 144d show different length plugs with integrated pin caps that can be inserted to seal off the plug itself received by the collar.

FIG. 145 shows the same collar as FIG. 144 but with the plug inserted into the collar and with the plug cap in place.

FIG. 145a shows that which is shown in FIG. 145 but in side view.

DETAILED DESCRIPTION OF EMBODIMENTS

In the following description of some embodiments, identical components that appear in more than one figure or that share similar functionality are referenced in some instances by identical reference symbols or by new reference symbols with references back in the description.

Figure 3B:
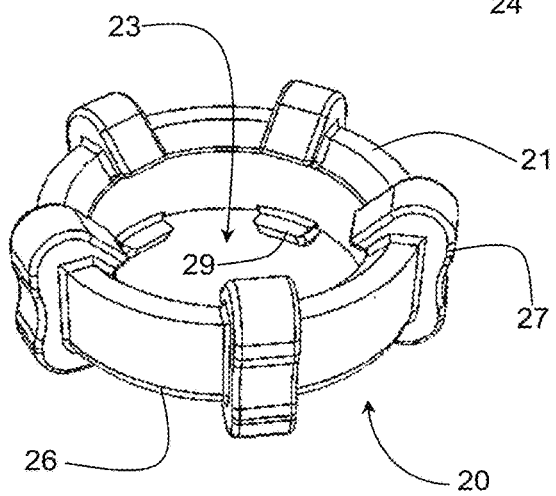
Figure 3C:
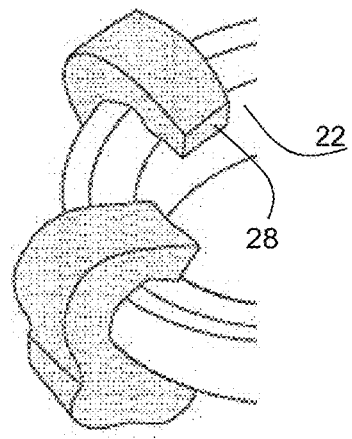

FIGS. 3a, 3b and 3c show pictorially a bottle support or mount 20 for supporting a cylindrical utensil, most typically having axial symmetry such as a cylindrical bottle. It should be noted that the bottle does not need to have a circular cross-section and the term cylindrical is used herein in its strict mathematical sense, namely a surface generated by a straight line intersecting and moving along a closed plane curve, the directrix, while remaining parallel to a fixed straight line that is not on or parallel to the plane of the directrix.

The bottle support 20 includes an annular core 21 having an inner side surface 22 defining a hollow opening 23, an outer side surface 24, a top surface 25 and a base surface 26. A plurality of pliable ribs 27 at least partially encircle the annular core 21 so as to overlap the outer side surface 24, the top surface 25 and the base surface 26 such that at least an upper end 28 of each rib where it overlaps the top surface extends into the hollow opening 23. In some embodiments the lower ends 29 of at least some of the ribs where they overlap the base surface 26 also extend into the hollow opening 23. The annular core 21 may be formed of rigid material or it may be pliable. If it is rigid and circular, then the shape of a bottle than can be conveniently inserted is largely dictated by the extent to which the ribs can deform. Typically, this will restrict use of the device to bottles of regular cross-section, most typically circular. But if the core is also formed of pliable material, then there is virtually no limit to the shape of the bottle, or any other artifact, that can be securely retained therein.

The annular core 21 and the ribs 27 may be formed of a composite molding (e.g., a one shot molding of both the ribs and annular core together) of pliable material. Alternatively, the ribs may be a composite C-shaped molding of pliable material and may be attached to an also molded annular core 21 using adhesive or plastic welding. In this case, there is no requirement for the annular core 21 and the ribs 27 to be formed of the same material.

Figure 2A:
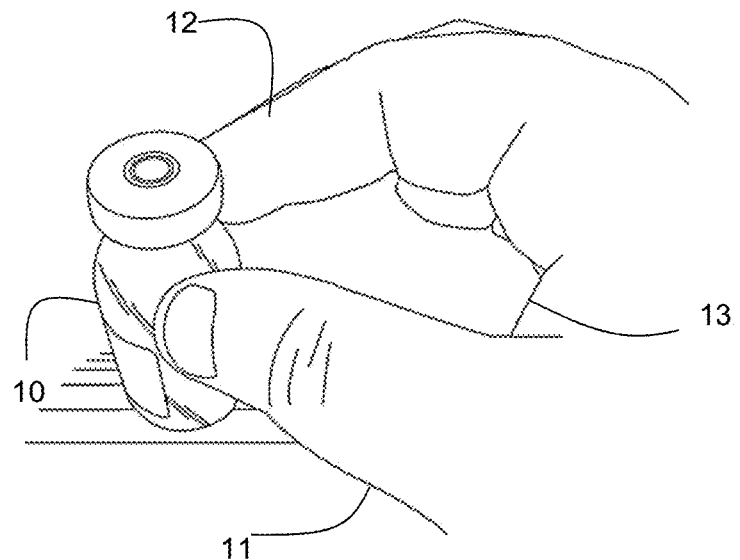
FIGS. 2a and 2b show pictorially the tendency of a cylindrical bottle to slip when gripped non-diametrically.
Figure 2B:
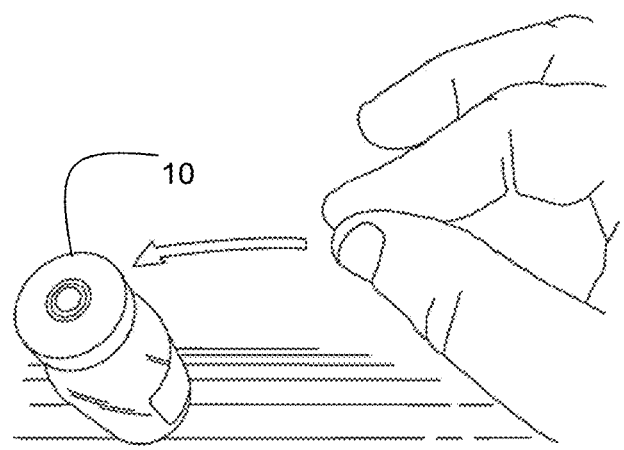
Figure 2C:
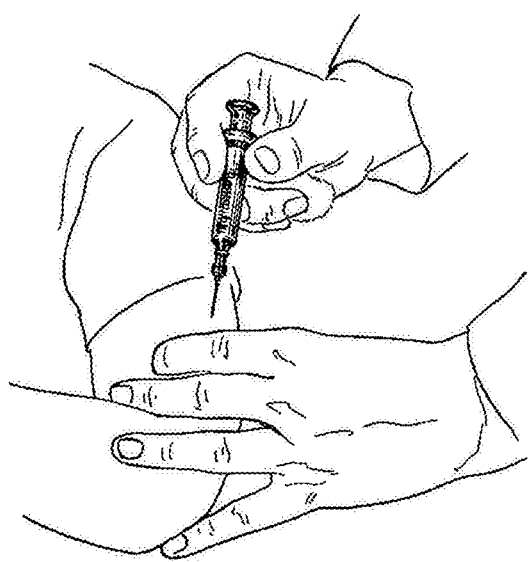
FIG. 2c shows pictorially conventional two-handed use of a hypodermic syringe.

Before describing applications of the mount, we will briefly explain the manner in which its construction is distinguished over known bottle supports. First, the pliability of the ribs 27 where they overhang the top surface 25 and extend into the hollow opening 23 allow the ribs to deform and grip the side surface of an object. Secondly, because the ribs are parallel to the axis of the core they are compressed transversely rather than deflected and no less importantly any two ribs may be deformed at different times and to different extents. This avoids the need to insert an object axially symmetrically and allows it to be inserted at an angle to axis. Thirdly, because the ribs overlap the outer side surface 24 of the core they increase the effective base area of the mount and lend added stability. Fourthly, since the ribs overlap the base surface 26, they serve to raise the base surface and insulate it from an external surface on which it is placed. Furthermore, where the lower ends of the ribs extend into the hollow opening 23, they support the base of an object supported therein and insulate it from the external surface. This helps to prevent the object, which may be a medicine bottle or vial, from becoming contaminated. Finally, because the ribs 27 extend outwardly from the generally smooth surface of the core they provide additional support surfaces that serve as ledges that are more easily grasped or pinched between thumb and forefinger or other fingers. This makes it much easier to grasp the mount securely even with wet or slippery hands and significantly reduces the tendency of the mount to roll away as shown in FIG. 2*b*. This functionality will now be described with reference to the drawings.

Figure 4A:
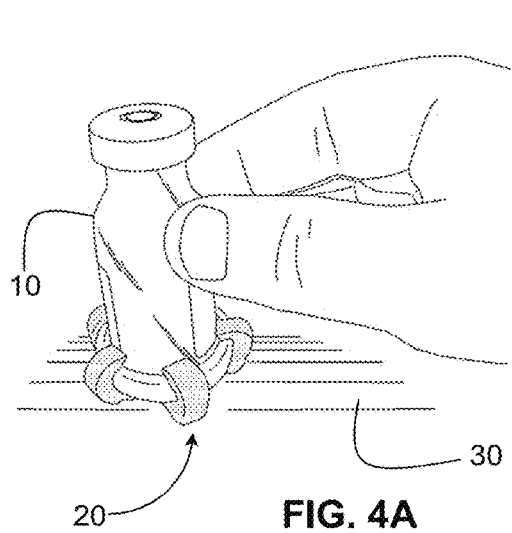
Figure 4B:
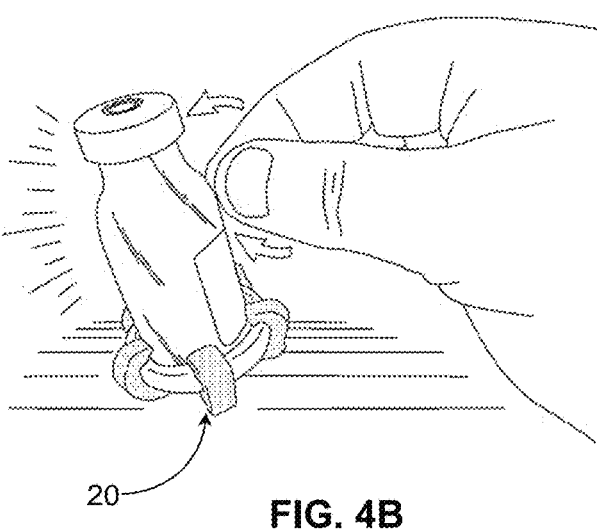

FIGS. 4*a* and 4*b* show a cylindrical bottle 10 supported by the bottle support 20. When the side surfaces of the bottle are grasped between forefinger and thumb particularly with the intention of lifting the bottle 10 from an external support surface 30, there is still a tendency for the bottle to slip away from the user's grasp. But this tendency is reduced owing to the friction between the lower surfaces of the ribs and the support surface 30 and the low center of gravity of support 20.

Figures 5A, 5B, 5C:
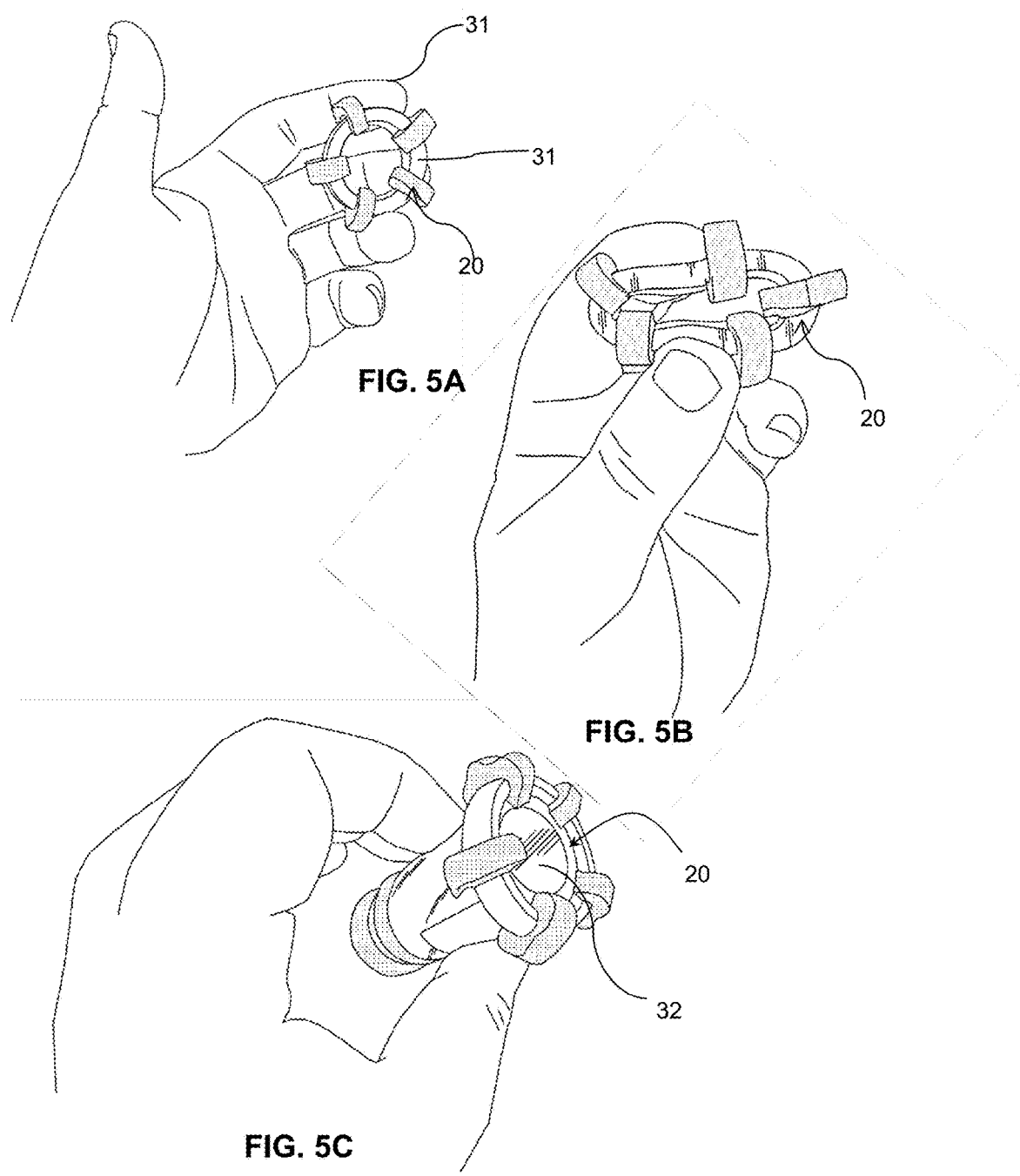
FIGS. 5a, 5b and 5c show pictorially the bottle support securely held between thumb and forefinger.

FIGS. 5*a* and 5*b* show the bottle support securely held between the tips of two fingers or between thumb and forefinger by pinching protruding outer side surfaces 31 of the ribs that serve as ledges that are more easily grasped or pinched between the fingertips. In FIG. 5*c*, rather than lifting the bottle by holding the bottle support 20, the bottle is grasped but with the tips of the forefinger and thumb pressing against the tops of the ribs, which likewise serve as ledges that facilitate grasping or pinching activity between the fingertips. It is also seen that the lower surface of the bottle does not protrude out of the lower surface of the base of the bottle holder, thus forming a recess 32 into which a user may insert his thumb or finger when grasping the bottle support from below. Applications that exploit this functionality are described below FIG. 5*b* shows the flexible quality in the mount 20. Further, its "open" design makes for visibility not being obstructed in use, as in being able to view for liquid content in the bottom when the bottle is clear as well as side labeling.

Figure 6A:
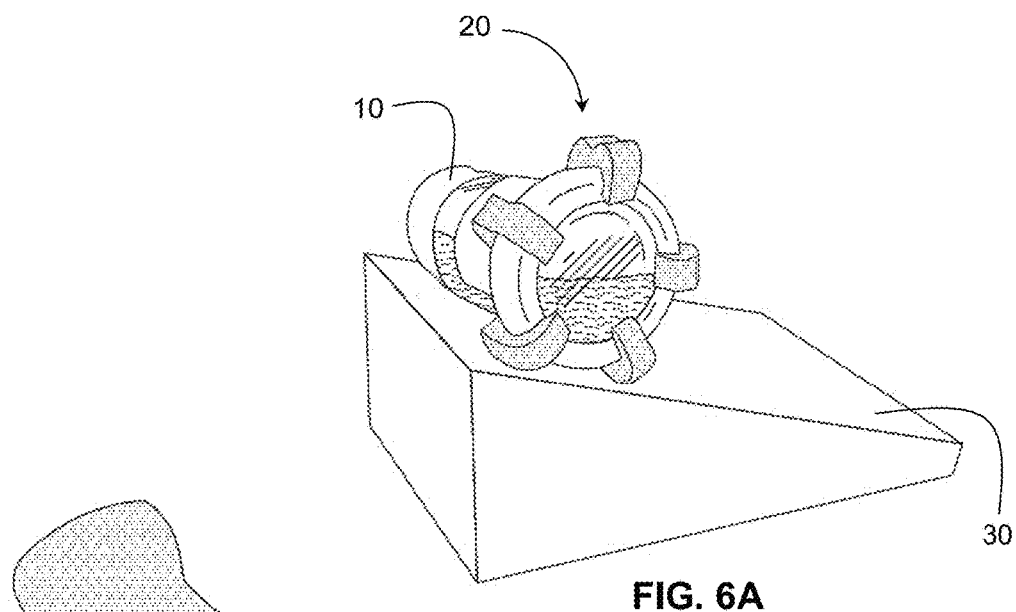
FIGS. 6a, 6b and 6c show pictorially the bottle support preventing rolling or tipping of an inclined bottle.
Figure 6B:
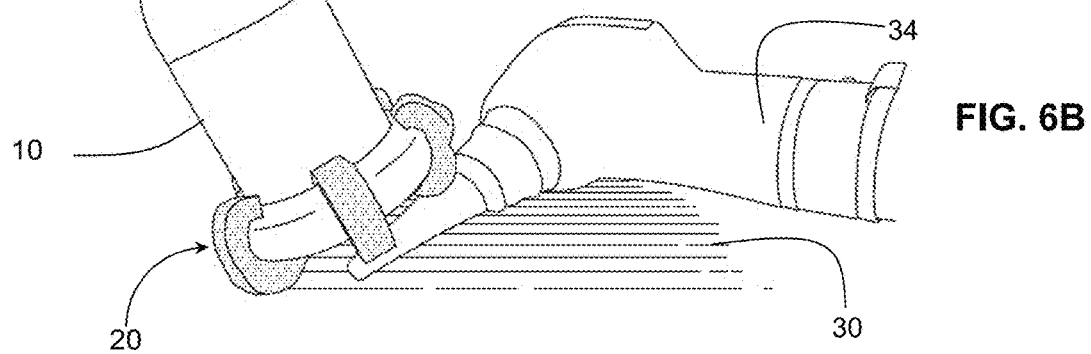
Figure 6C:
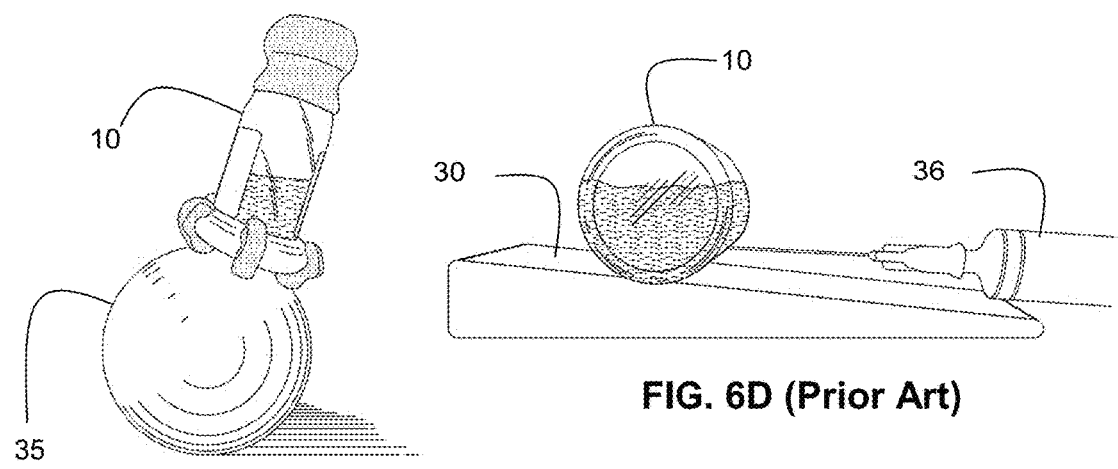
Figure 6D:
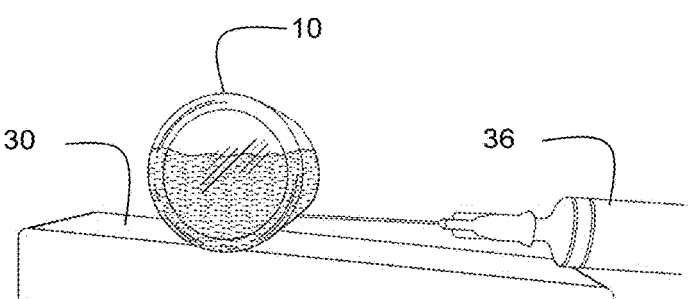
FIG. 6d shows how a cylindrical bottle may be prevented from rolling without use of the bottle support according to the invention.

FIG. 6*a* shows the bottle support 20 preventing rolling of a bottle 10 placed on an inclined support surface 30, with the pertinent parts of the bottle still visible. FIG. 6*b* shows that the bottle support 20 is less prone to tipping even when partially tilted owing to its being placed, possibly inadvertently, on a tool 34 lying on a level surface 30 as is easily done in stressful working conditions such as operating theaters and the like. FIG. 6*c* shows a bottle 10 supported within the bottle support 20 while stably retained at a significant incline on a spherical object 35. FIG. 6*d* shows how medical staff may otherwise try to prevent a bottle 10 on an inclined surface 30 from rolling when no bottle support is available by retaining the bottle with the needle of a hypodermic syringe FIGS. 6*a* to 6*d* also show that in all positions the open nature of the mounts avoids obstructing view points as in vial labels.

Figure 7:
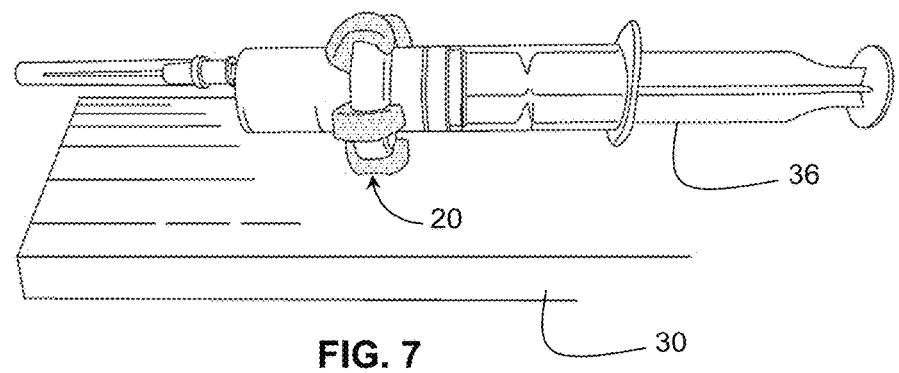
FIG. 7 shows pictorially use of the bottle support to avoid rolling of a hypodermic syringe.
Figure 8:
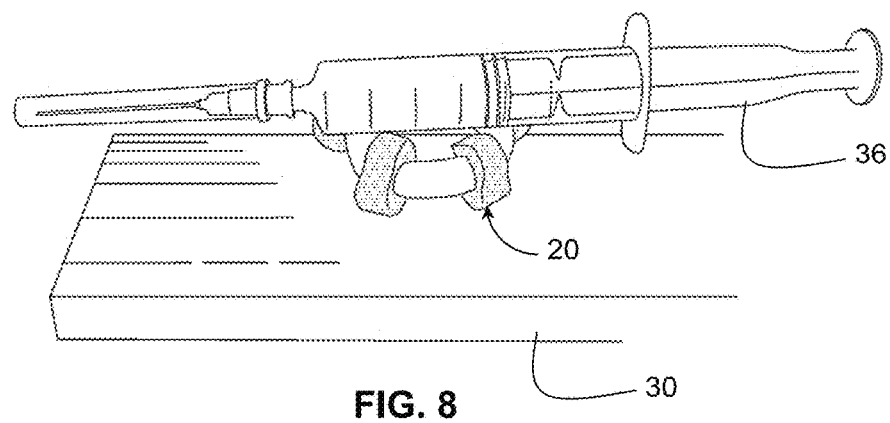
FIG. 8 shows pictorially use of the bottle support to isolate a hypodermic syringe from a working surface.

FIG. 7 shows pictorially use of the bottle support 20 to avoid rolling of a hypodermic syringe 36 by securing the bottle support 20 around the body of the syringe. Such use can include an arrangement where that the lower ends of the ribs of the bottle support 20 do not extend into the hollow or extend to a lesser extent, thus allowing the bottle support to be slid up and down the body of the syringe. FIG. 8 shows use of the bottle support 20 to isolate a hypodermic syringe 36 from a working surface 30 thus prevent cross-contamination and at the same time preventing rolling of the syringe 36 (e.g., it suspended horizontal state relative to a potentially contaminated undersurface). Obviously, the same principles can be applied to other utensils Also, FIG. 7 shows that the syringe is supported in a manner that both avoids contamination and allows ready finger insertion below the syringe for easy pick up.

We now describe another aspect of the invention that relates to grasping a bottle not by its base but rather from its neck.

Figures 9A, 9B:
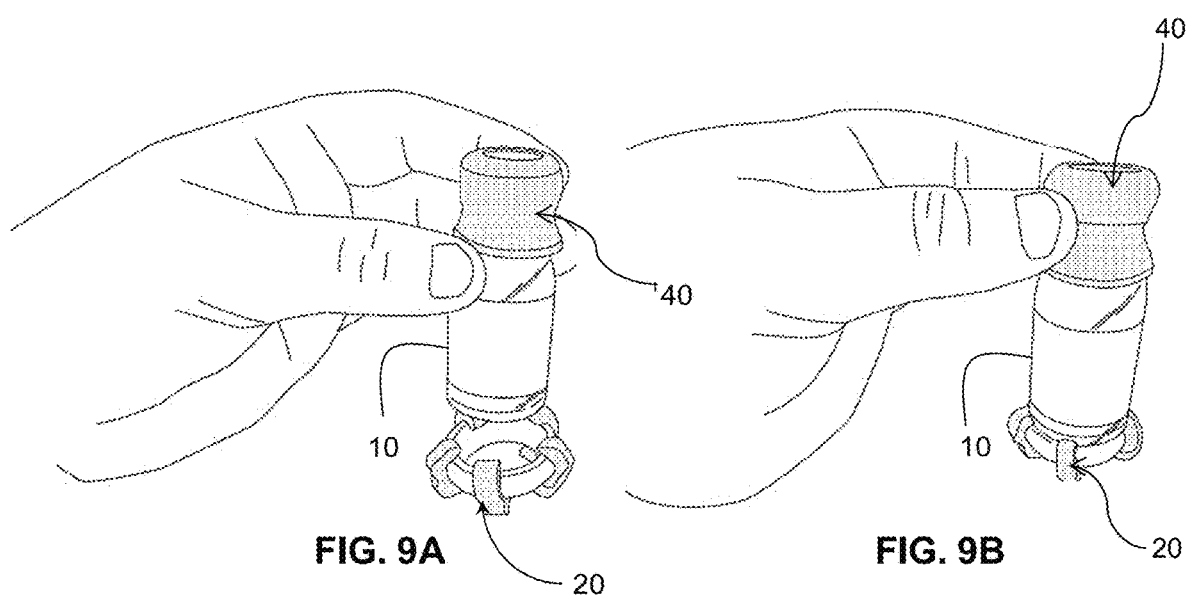
FIGS. 9a and 9b show pictorially an assembly according to a second embodiment of the invention comprising a bottle support and a collar.

Thus, referring to FIGS. 9*a* and 9*b* there is shown a bottle 10 having attached to its neck a collar 40 for facilitating non-slip gripping of the bottle.

FIGS. 10*a* and 10*b* show a first embodiment of the collar 40 comprising a body portion 41 having an axial bore 42 for surrounding the neck of a utensil such as a bottle, and defining along at least a portion of an axis 43 thereof a substantially quadrilateral cross-section having in each corner thereof a respective arcuate recess 44, each for accommodating a user's thumb or finger. The axial bore 42 may be configured to accommodate an end of a hypodermic syringe and, to this end, may include at least two mutually contiguous sections 42' and 42" of different cross-sectional areas so that the internal shape of the bore 42 is complementary to the external surface of the hypodermic syringe 36. The collar 40 may be formed of deformable material and dimensioned for axial compression or displacement of a predetermined distance that is adjusted to define a known protrusion of a hypodermic needle. This allows the collar 40 to be located at the end of the hypodermic needle, while concealing the tip of the needle, such that pushing the body of the syringe into the patient's skin causes the collar to compress and the needle to enter the skin. In an alternate embodiment collar 40 is formed of a non-compressible plastic material that, in use, ensures the exposed end of a needle shaft extending away from the collar reaches the same depth of penetration upon collar-to-skin contact.

In the embodiment of FIG. 10*a* the body portion 41 is of rectangular cross-section and defines opposing pairs of first and second ridge side surfaces of different widths. In other embodiments, the body portion may be of square cross-section all of whose surfaces are of equal width. At least one of the side surfaces may have an indent or depression 45 for accommodating the user's finger. By way of example, the indent may be elongated with a major axis normal to an axis of the body portion. In some embodiments the top corners of the collar may be slanted as shown schematically by chain-dotted lines in FIG. 10*b* so that when the collar 40 is fitted to the operative end of a hypodermic syringe (or some other object) as described in more detail below, the resulting slanted edges may serve to guide the insertion of the needle at an angle determined by the degree of slant.

As a few non-limiting but illustrative dimensions for collar 40 embodiments, such as those in the examples described herein, a width (space between opposing longer length ridge walls representing peripheral, generally straight longer sides of the collar's periphery) of 18 mm is featured, while a length range (between opposing short length opposing ridge walls) of 25 mm is featured. As described in greater detail below, the height can vary greatly as in 2 mm heights up to 60 mm or more. As with all ranges discussed herein (unless otherwise indicated) all end points and points between the end points at the same unit dimension are intended for coverage herein. Additional non-limiting, but illustrative values for collar 40 includes a thickness height of 21 mm, a peripheral length of 6.5 mm in short ridge sides, and 13 mm peripheral length for the long ridge sides. The overall long length of collar 40 (from short ridge surface to short ridge surface of 30 mm is illustrative. Some additional non-limiting, illustrative dimensions are provided below relative to FIG. 110 plus.

FIG. 11 shows a second embodiment of a collar 40, having a body portion 41 an outer surface of which has a tapered portion 42 that projects axially upward opposite a base portion of the collar. The body portion includes a lower portion of substantially quadrilateral cross-section, typically square or rectangular. The tapered portion 42 may be of smaller cross-sectional area than the base portion as shown in the figures so it that it tapers upward. Alternatively, it may be of larger cross-sectional area than the base portion so that it tapers downward. As in the first embodiment shown in FIG. 10a, in each corner of the body portion 41 there is formed a respective arcuate recess 44 for accommodating a user's thumb or finger. In some uses, it may be advantageous for the collar to be closed at one end to form a cap, or at the bottom to form a reception collar.

FIG. 12 shows use of the collar 40 when transferring liquid between the bottle 10 and a hypodermic syringe 36. Thus, the neck of the collar 40 defines a ribbed surface that is gripped between two fingers of one hand while the thumb of the same hand is held within the recess 32 of the base described above and shown in FIG. 5c. To this end, the collar may have a beveled indent 47 for better accommodating the fingers as best shown in FIG. 13. The user's other hand holds the hypodermic syringe 36 and aligns the needle 46 into the opening of the bottle. The ribbed surface of the collar 40 provides some measure of shielding that reduces the risk of self-injection.

FIG. 13 shows one use of the bottle support 20 to reduce the risk of self-injury by supporting the bottle or vial 10 in the bottle support 20 on a support surface 30 so as to obviate the need for the user to touch or hold the via while aligning the hypodermic syringe therewith.

Figure 14:
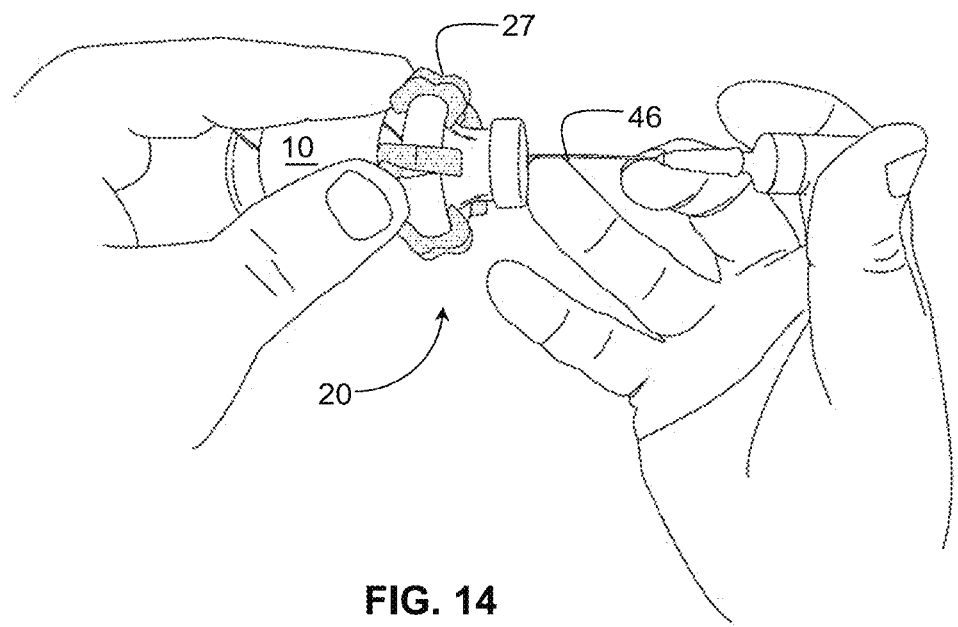

FIG. 14 shows another use of the bottle support 20 to reduce the risk of self-injury by displacing the support 20 from the base of the bottle 10 toward the neck and grasping the bottle behind the ribs 27, which completely shield the fingers from the needle 46. In FIG. 14, the ribs are arranged in reverse orientation as when used as a base bottle support. That is, the ribs 27 have their planar surface extensions 29 oriented in a down direction (the opposite arrangement to that when extensions 29 are oriented to support the underside of the supported vial when the collar is a base support mount) so as to push down and contact the upper neck part of the bottle where the neck extends into the larger circumference main body of the bottle. In this way the mount retains a steady position while the user grasps the collar in a protective pull-down behind mount arrangement.

Figure 15:
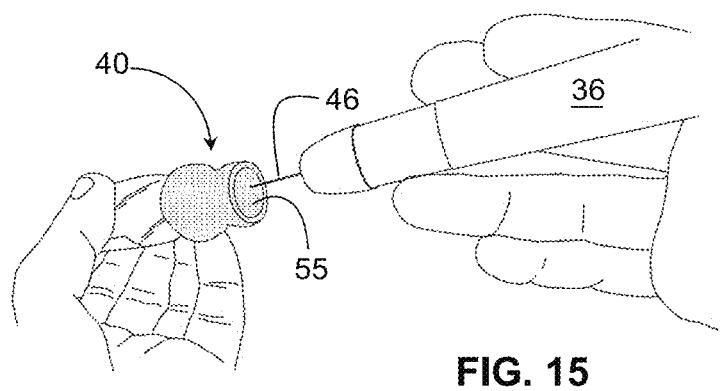
FIGS. 15 and 16 show use of the collar to avoid the risk of self-injection or damage when transferring liquid between the bottle and a hypodermic syringe and also to provide the possibility of a one handed suspended retention after connection.
Figure 16:
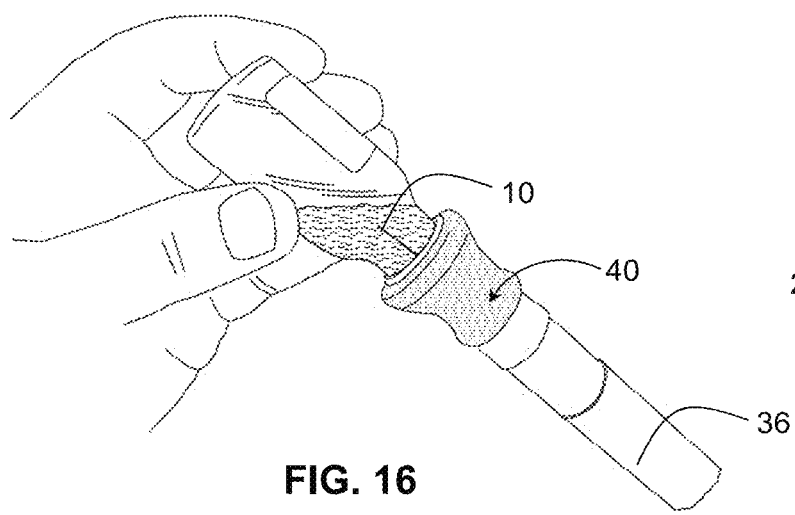

FIG. 15 shows another embodiment where this risk is avoided altogether by elongating the collar 40 and providing at its end an internal axial bore 55 configured to accommodate an end of the hypodermic syringe 36, thus allowing the neck of the bottle 10 to be coupled to the hypodermic syringe 36 as shown in FIG. 16. By such means the collar 40 serves both as a grip and a sleeve or coupler for coupling to the mouth of another utensil as shown in FIG. 16.

Figure 17:
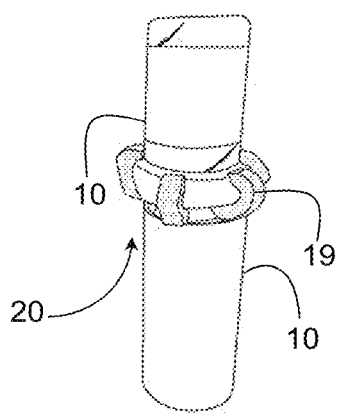
FIG. 17 shows use of the bottle support to effect limited coupling between the bottle and another utensil.

FIG. 17 shows use of the bottle support 20 to effect limited coupling between the bottle 10 and another utensil 10. Thus, when the bottle 10 is inserted into the bottle support 20, the depth of the ribs 19 at their lower ends creates a recess 32 shown in FIG. 5c. It will be appreciated that the depth of the recess depends on the dimensions and geometry of the ribs, specifically how far they extend beneath the base of the bottle support. But it also may be a function of their overall length and thickness and even their resilience since these factors will determine how far the bottle 10 needs to be pushed down into the bottle support to be firmly supported thereby. If the ribs are sufficiently stiff to support the bottle without the need to push the bottle down fully, this allows the effective depth of the recess 32 to be increased.

We have described so far multiple uses of the bottle support and the collar, both independently and in combination. We now describe further optional features of the collar which have particular application to its use with hypodermic syringes and other utensils and are intended to ameliorate one or more of the drawbacks discussed above.

Figure 18:
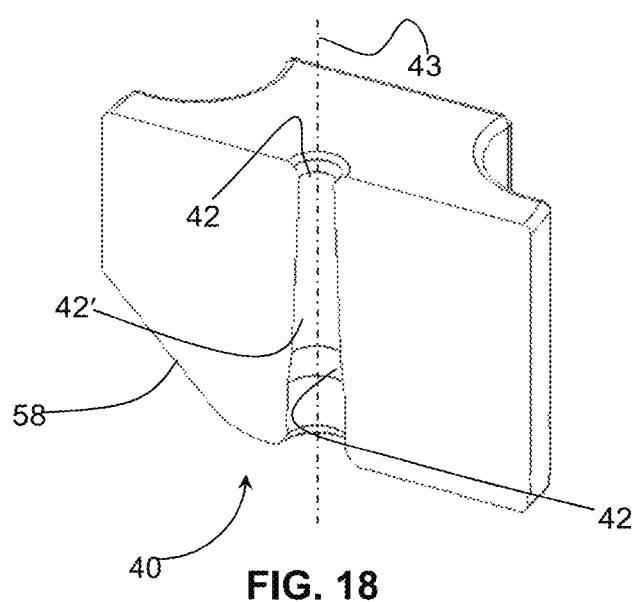
FIG. 18 shows in cross-section a collar having a slanted surface for guiding a hypodermic syringe or fitting over a narrow vial at the bottom while a hypodermic needle syringe enters from the top.

FIG. 18 shows in cross-section a collar 40 having a bore 42 shaped for accommodating the end of a hypodermic syringe (not shown) as described above with reference to FIG. 10b. One side face 58 of the collar is at least partially beveled or slanted at an angle of, for example, 15° (or one of the other angles described above for (e.g., 15°, 20°, 40°, 60°) so that, in use, when this surface is guided along (or retained relative to) the surface of a patient's skin, the needle (not shown) will be maintained at an appropriate angle for venous injection without the need for manual support by the operator's finger. It should be noted that the drawing is schematic and in practice the slanted edge will be toward the front of the collar as shown by the chain-dotted lines in FIG. 10b, or at both ends.

Figure 19:
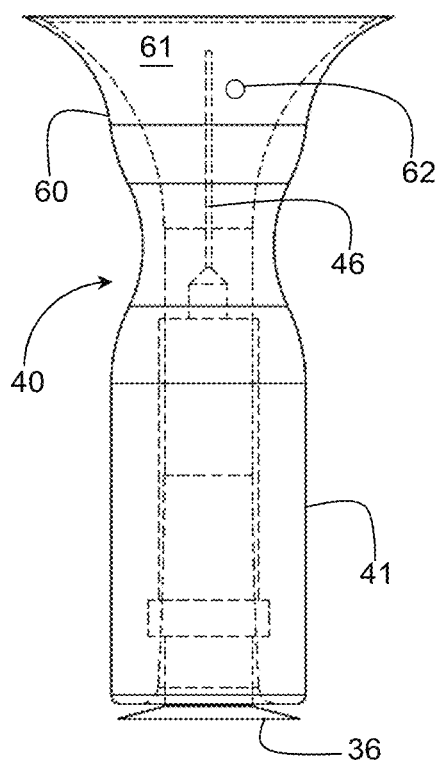
FIG. 19 shows in cross-section a collar fitted over the operative end of a hypodermic syringe for shielding the needle.

FIG. 19 shows in cross-section a collar 40 whose body 41 has an axial bore shaped to accommodate the operative end of a hypodermic syringe 36 and having a horn shaped front end 60 for shielding the needle 46. The horn shaped front end 60 is flared to provide a peripheral flexible skirt 61 that is formed of thin elastic material (e.g., 1.0 mm to 2.0 mm thickness at the skin contact end of the skirt) that is dimensioned such that in the initial state prior to use it completely covers and conceals the needle, but axially deforms when pushed against the surface of a patient's skin so as to retreat as the needle is injected. In order to prevent the flexible skirt 61 sticking to the patient's skin, one or more breathing apertures 62 are provided around the periphery of the skirt that admit air and hinder suction. Alternatively, the flexible skirt 61 may be dimensioned so that that in the initial state prior to use the needle protrudes a predetermined length.

Figure 20:
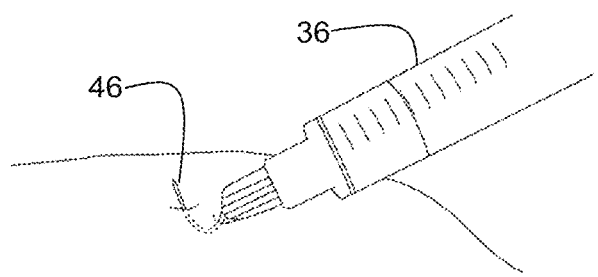
FIG. 20 shows bending of a hypodermic needle that may occur with conventional syringes resulting in extension under the skin in fish hook type fashion.

The extent to which the needle 46 protrudes in the default state directly impacts on its tendency to bend. Some hypodermic needles are very thin and easily deformed. If they are injected at the wrong angle and/or the patient moves, the needle can bend as shown in FIG. 20 and puncture the patient's skin in two locations. This is both painful and ineffective because the contents of the syringe are wasted and thus requires a further injection.

Figure 21:
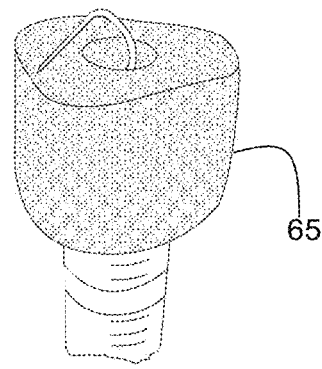
FIG. 21 shows pictorially a resilient collar that reduces the malfunction shown in FIG. 20.
Figure 22:
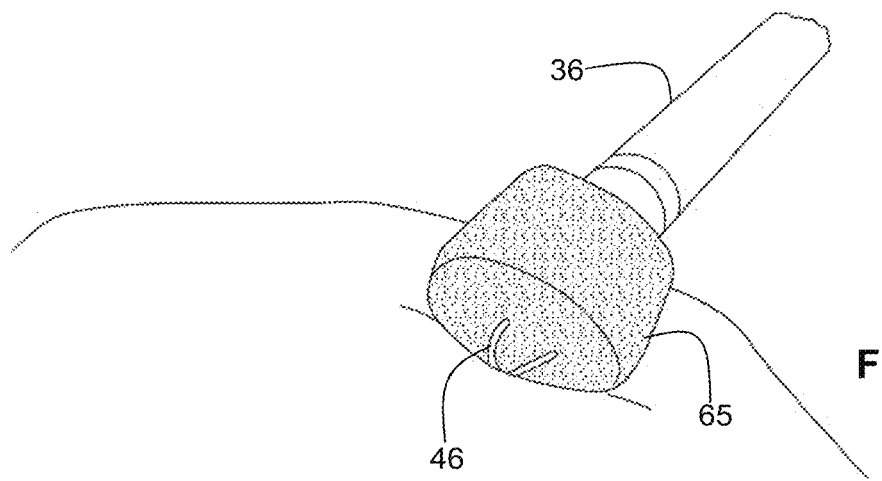
FIG. 22 shows pictorially how the collar of FIG. 21 cushions the needle and prevents it from bending inside the patient's skin.
Figure 23A:
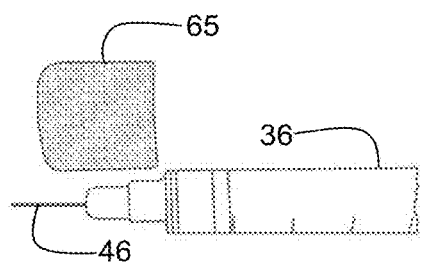
FIGS. 23a and 23b show respectively details of a hypodermic syringe before and after the collar of FIG. 21 is fitted over the needle.
Figure 23B:
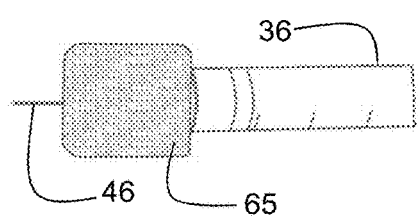
Figure 24A:
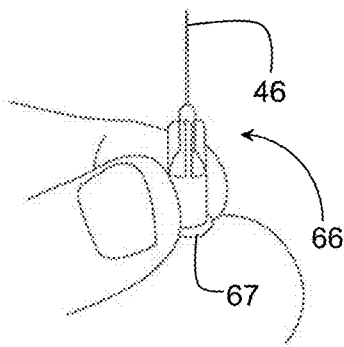
FIG. 24a shows a detail of a prior art needle assembly.
Figure 25:
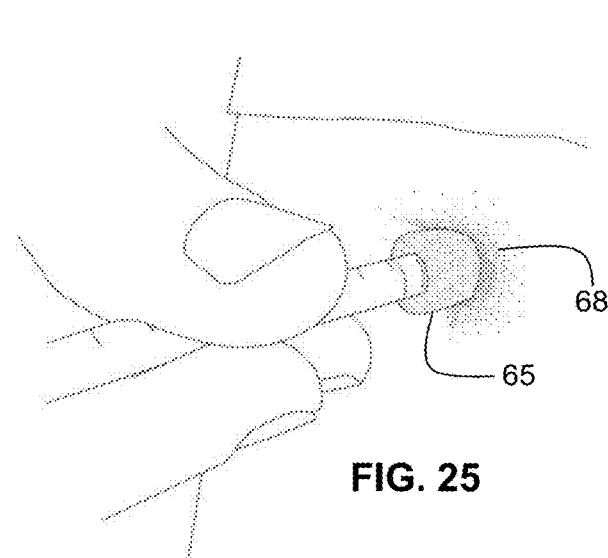
FIG. 25 shows the effect of using the collar to spread the pressure over a wider area.
Figure 24B:
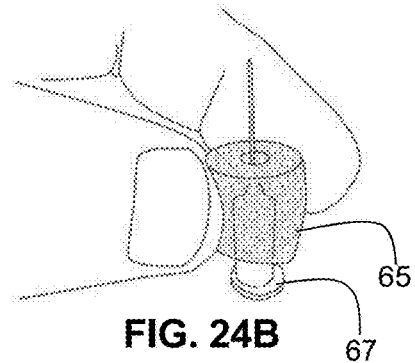
FIG. 24b shows pictorially how the collar of FIG. 21 is fitted on to such a needle assembly.
Figures 26A, 26B, 26C:
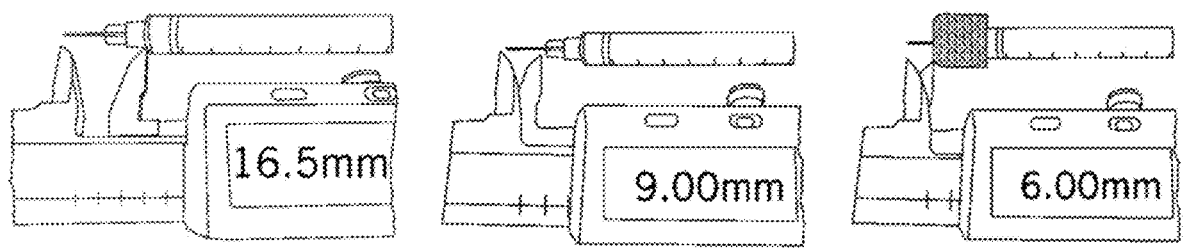
FIGS. 26a, 26b and 26c show typical dimensions associated with the needle assembly with and without the collar in situ.

FIG. 21 shows how this malfunction can at least be mitigated by use of a collar 65 formed of deformable material such as foam and dimensioned for axial compression or displacement of a predetermined distance that is adjusted to define a known protrusion of a hypodermic needle. In this embodiment, the collar has a solid base portion that serves as a cap. FIG. 22 shows use of the collar 65, which abuts the skin as the needle 46 is injected. Should the needle bend owing to slight misalignment, it is cushioned by the collar and will bend back on itself without penetrating the patient's skin. FIGS. 23a and 23b show respectively details of the hypodermic syringe before and after the collar 65 is fitted over the needle. FIG. 24a shows a detail of a needle assembly 66 having a base 67 supporting the needle 46. FIG. 24b shows the collar 65 as it is fitted on to the needle assembly 66 so as to be supported by a peripheral flange of the base with the needle protruding through the opposite end of the collar. FIG. 25 shows the effect of using the collar 65, which pushes against the surface of the patient's skin over an extended area 68 thereof, which spreads the pressure over a wider area thereby reducing pain and assists in distributing the contents of the syringe more quickly through the surrounding tissue. FIGS. 26a, 26b and 26c show respectively typical dimensions of the needle assembly 66 (16.5 mm), and the length of the protruding end of the needle 46 without (9 mm) and with (6 mm) the collar in situ. In an alternate embodiment the collar is designed to not be compressible upon skin contact but to keep a fixed length needle extension below the skin contact.

In all embodiments, the collar may be integral with the object or utensil to which it is coupled. So, for example, it may be integral with the bottle allowing easy coupling to the hypodermic syringe, or vice versa.

Figure 27A:
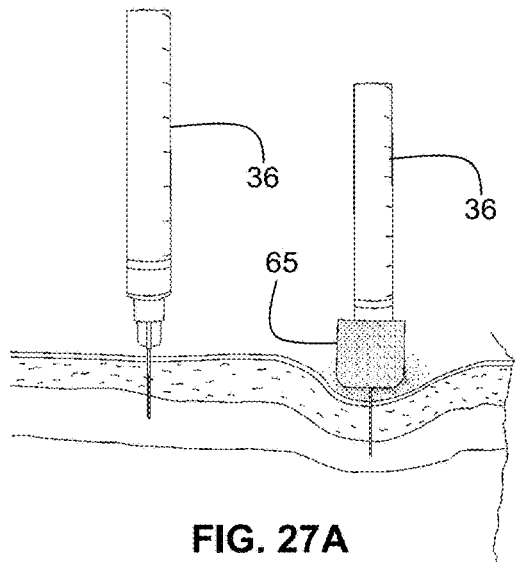
FIGS. 27a, 27b and 27c show pictorially comparisons of prior art syringes with a syringe fitted with the collar of FIG. 21.
Figure 27B:
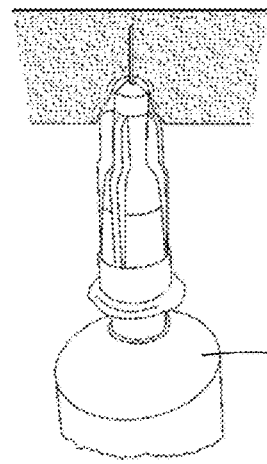
Figure 27C:
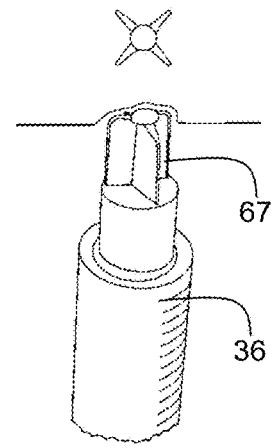

FIGS. 27a, 27b and 27c show pictorially comparisons of prior art syringes with a syringe fitted with the collar of FIG. 21. Thus as best seen in FIGS. 27b and 27c the operative end of the hypodermic syringe has two intersecting ridges that press into the skin if pushed too deeply, causing significant pain to the patient. In contrast thereto, the resilient collar 65 cushions the impact and helps to distribute pressure and thereby reduces pain. Alternatively, the collar can be made rigid enough not to compress in use against skin contact as to control the puncture depth, while still helping to disperse (increase) the area of instrument to skin contact.

Figure 28:
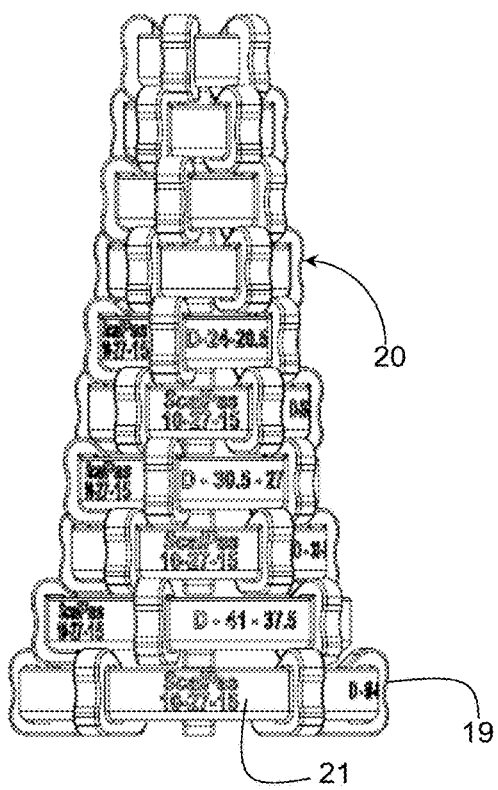
FIG. 28 shows pictorially multiple bottle supports stacked for easy display and packing.

FIG. 28 shows pictorially multiple bottle supports 20 of different diameters stacked for easy display and packing. Preferably, the annular core 21 of each bottle support is dimensioned so that when stacked on top of an immediately adjacent bottle support of larger diameter, the annular core 21 of the upper bottle support is supported by the ribs 19 of the lower bottle support, while the ribs of the upper bottle support are supported by the annular core of the lower bottle support. Even more preferably, the annular cores 21 are dimensioned so that any two alternate bottle supports can be stacked flat. In other words, the outer edges of the ribs 19 of the smaller bottle support fit snugly within the inner edges of the ribs 19 of the lower bottle support. In this case, multiple bottle supports can either be stacked into a tower as shown in FIG. 28 or they be dismantled and reassembled to form two sets of concentric rings.

Figure 29A:
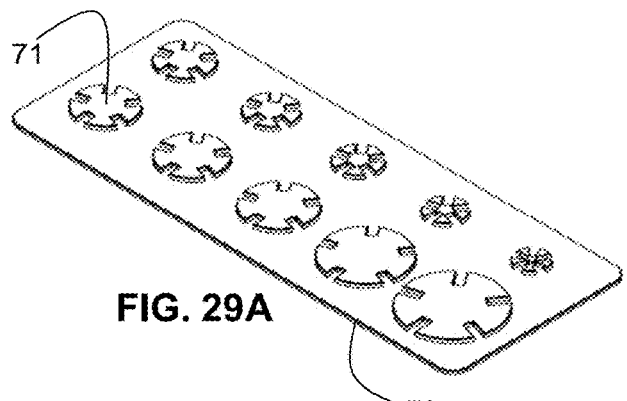
FIG. 29a shows pictorially a tray for mounting multiple bottle supports.
Figure 29B:
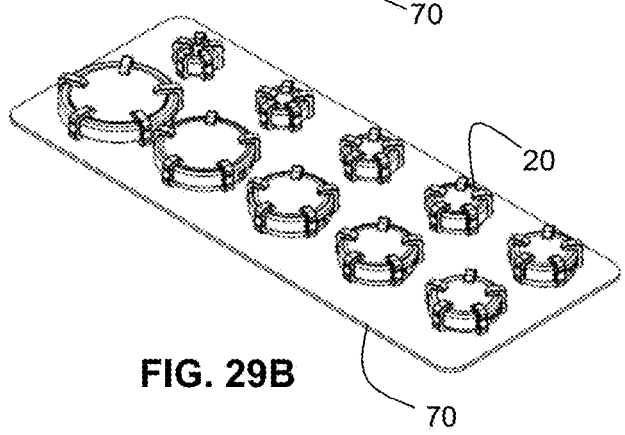
FIG. 29b shows pictorially use of such a tray to mount multiple bottle supports.

FIG. 29a shows pictorially a tray 70 for mounting multiple bottle supports 20. The tray 70 has a plurality of upraised protuberances each dimensioned for accommodating a bottle support of appropriate diameter as shown in FIG. 29b.

Figure 30:
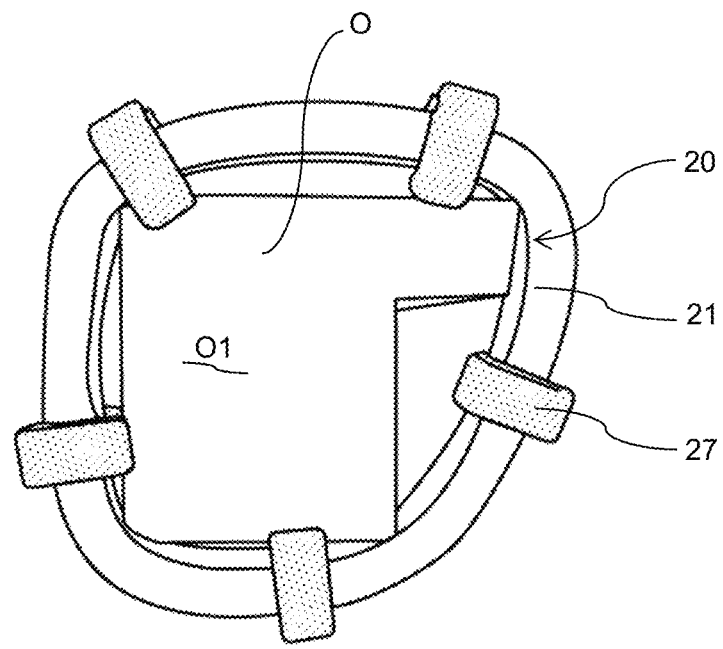
FIG. 30 shows a bottom plan view of a pliable annular core mount providing mounting support to a multi-linear side utensil.

FIG. 30 shows a bottom plan view of pliable annular core mount 20 providing mounting support to a multi-linear side utensil O. FIG. 30 illustrates the versatility of mount 20 with a pliable annular core 21. As seen in the support interrelationship between pliable mount 20 and the multi-sided utensil O, mount 20 is adaptable to a wide variety of objects inclusive of those having non-curved peripheries and inclusive of those having deep notches or concave sections. FIG. 30 further shows pliable ribs 27 conforming as well to the non-curved, convex periphery of object or utensil O.

In the illustrated FIG. 30 embodiment there are five ribs 27 equally spaced about the length of annular core 21 (e.g., an annular core of an internal (hollow defining) diameter of for example, a non-limiting but illustrative range of 3 mm to 7.5 cm), although greater or less than five ribs 27 are featured under the present invention, as in 2 or more and 10 or less ribs 27 for the noted annular core range (although, for larger diameter annular cores, as in those falling in the upper half of the interior diameter range noted or above, more than 10 and less than 20 ribs may be applicable). FIG. 30 further illustrates that, depending on the shape of object O, one or a multiple (e.g., less than half of the total ribs 27 mounted on the annular core 21) may be suspended away from the object O's periphery and not in contact with the utensil or object O's surface.

FIG. 30 also shows that for some object O configurations, annular core 21 may directly contact one or more points of the object O's periphery. In this case, there are three points or more of contact between an edge of the object O and annular core 21, and four ribs in direct contact locations, and one free rib 27. Again, this shows the versatility of the mount 20 in both accommodating a wide variety of peripheral object shapes, while still providing a stable support at the base of the object, which base support can avoid planar slipping along a supporting surface such that a user can free up a hand for other uses rather than holding the object O in place. Providing the ribs 27 of a high friction material such as silicone enhances the non-slip relationship with the support surface. That is, as explained above, ribs 27 can be formed of a variety of material with a preference toward high friction and pliable or flexible materials as in silicon rubber compounds; Thermoplastic elastomers (TPE) (see https://en.wikipedia.org/wiki/Thermoplastic elastomer, as an example for added background); Thermoplastic Rubber (TPR) (see http://www.sespoly.com/products/tpr-thermoplastic-rubber/, as an example for added background); Polyvinyl chloride (PVC) (see https://en.wikipedia.org/wiki/Polyvinyl_chloride, as an example for added background) or any combination of the above either blended before formation or a physical combination as in a laminate arrangement.

As also explained above, the ribs 27 and annular core 21 can be formed of the same or different material, inclusive of different materials, but with each being flexible.

For example, an embodiment features each of ribs 27 and annular core 21 being pliable or flexible as in when formed of one material in a common molding. Other embodiments feature, ribs being more flexible than the annular core, with additional alternate embodiments featuring less pliable ribs mounted on a more pliable annular core, or equally pliable levels in the ribs and core (e.g., each rib and the core formed of medical grade silicone and/or one of the other TPE, TPR, or PVC plastics described above). Medical grade silicone comes in a variety of hardness values and for the purposes of mount 20 the hardness values are preferably about 20 to 80 shore hardness, as in 30 to 50 shore hardness, with 40 shore hardness being well suited for many embodiments (the shore ranges being suitable for each of core 21 and ribs 27). Also, although object O is shown to be of equal height above its base, the present invention is also suited for supporting the base of non-common height bodies. Further, although ribs 27 are shown each of common height and configuration, variations to achieve ribs in a mount of different height and/or configuration are featured.

Figure 31:
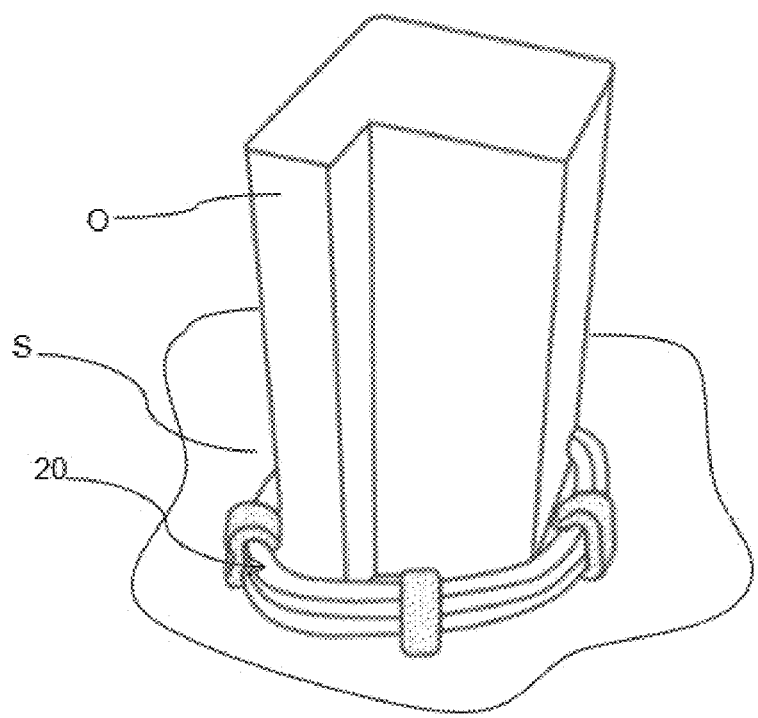
FIG. 31 shows the mount and utensil combination of FIG. 30 in a front elevational view.

FIG. 31 shows the mount 20 and utensil O combination of FIG. 30 in a front elevational view and the manner in which the ribs 27 suspend object O off of support surface S while still providing high friction contact with that surface S. FIG. 31 further shows a perspective view of that which is shown in FIG. 30 with mount 20 being engaged with the base end of object O as to lift the bottom surface O1 off from contact with the underlying surface S. This suspension of object O above surface S is achieved by way of the ribs 27 extension below the lower most surface of annular core and the engagement of the ribs such that they extend to opposite sides of a plane resting on bottom surface O1. For example, some non-limiting, but illustrative numerical values for mount 20 (e.g., see FIG. 3b) are as follows: the top surface of annular core 21 has a 2.5 mm width, the radial thickness of the annular core at its middle is 4 mm, and the height of the core is 8 mm. As some non-limiting examples of suitable rib dimensions for some uses under the present invention there is noted: a rib width of 5 mm (along the circumference of the annular core). Also, the radial extension into the hollow of 1.5 mm at the top free end of the rib, with a longer (e.g., 3.5 mm radial extension into the hollow at the bottom of the rib (this extension having a height thickness of 2 mm, for example)). The ribs minimum thickness at the center of the annular core height and preferably is 2 mm with thicker curved rib sections extending above and below. The overall height of the ribs is about 14 mm. Thus, for this embodiment a suspension height between the bottom of the supported object and the support surface of about 2 mm is present. As further described herein various other dimensions for mount 20 are featured and thus the suspension height can be varied as well.

FIGS. 32a and 32b show a top plan view of the components of FIG. 31 separated apart. In other words, FIGS. 32a and 32b show the removal or separation of mount 20 from object O, with contraction of the previously expanded annular core 21 (e.g., annular core stretch value at the time of utensil support is sufficient to extend the core diameter from its natural contraction state to one that can accommodate the maximum peripheral distance value MD shown in FIG. 32a). Upon separation of mount 20 from object O, core 21 contracts back down from its stretched mount state to its contracted non-stretched/non-use state of, for example, 3 mm to 7.5 cm to reflect the natural hollow diameter of core 21. The initial non-contraction annular core dimension suited for the object will also be dependent upon the stretch % in the material used, as in typically a lower shore hardness value will have a greater stretch percentage potential and vice versa. For example, a stretch % of 5-25% of the original contracted diameter is illustrative, with a lower shore value of say shore 20 will typically be at the higher 25% end of the stretch range, while a shore 80 material will typically be more toward the 5% end of the elasticity range. In other words, a shore 80 elastomeric material typically has the advantage of strength and rigidity, while lower shore value (e.g., 20 shore) have the disadvantages of potential tearing and excess elasticity. The decision will be in the force of the function one is achieving relative to particular embodiments described herein. Also, there is the possibility of combining multiple surrounding mount ring assemblies, with a shore 20 mount ring combined in nested fashion and with a shore of about 40 or 60 surrounding it, either based on physical nesting or based on a secured together laminate arrangement.

FIG. 33 shows the pliable annular core mount in supporting fashion at the base of a different utensil U, in the form of a bottle with a quadrilateral periphery (e.g., a square periphery). That is, FIG. 33 provides an additional perspective view of a suspended bottle U (different than the above described vial bottles with rubber seal tops and crimping metal ring covers). Bottle U in FIG. 33 is also shown as being suspended above support surface S in similar fashion to the suspension of object O described for FIG. 31. Suspended bottle U is shown as having a polygonal (e.g., square) periphery with the five ribs 27 contacting multiple flat side surfaces thereof.

Figure 34:
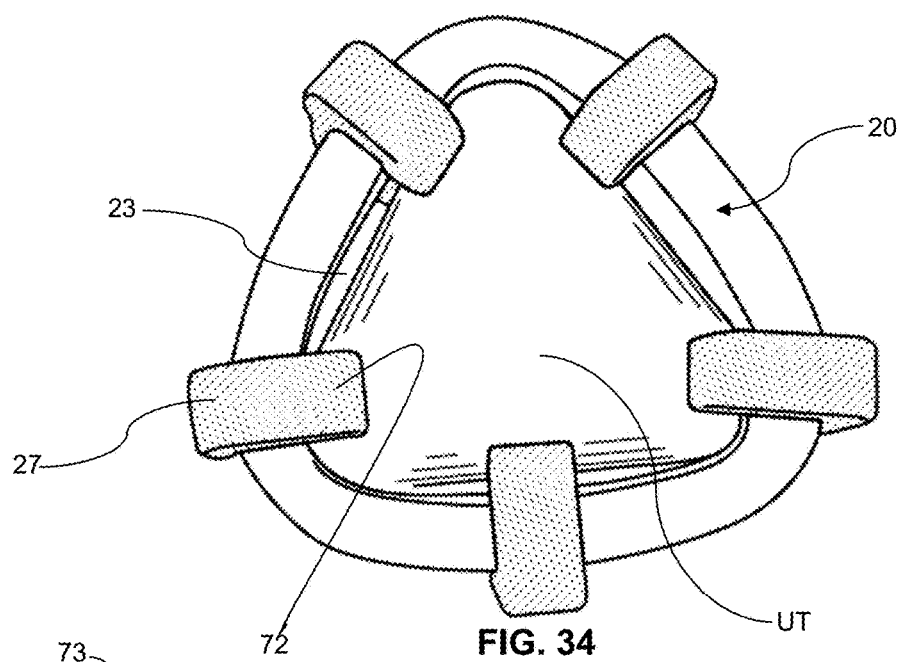
FIG. 34 shows a bottom plan view of the pliable annular core mount providing base support to a triangular cross-sectioned utensil.

FIG. 34 shows a bottom plan view of the pliable annular core mount or ring 20 providing base support to a triangular cross-sectioned utensil UT (e.g., an open top container for temporary fluid retention). That is, FIG. 34 shows an additional depiction of mount 20 provided as a high friction retention base mount to object UT, which in this case is a triangular shaped object with three sides, all of which are in contact with ribs 27. FIG. 34 further illustrates the lower extensions 72 of ribs 27 extending out into hollow 23 (e.g., for a length of 3.5 mm and a thickness of 2 mm, and with a horizontal, planar utensil support surface in that extension) as to contact an outer peripheral undersurface portion of object UT. In this way, there is provided a desired degree of object suspension above any supporting surface (from the upper planar surface of extensions 72 to the bottom (high friction) contact surface portion of ribs 27).

Figure 35:
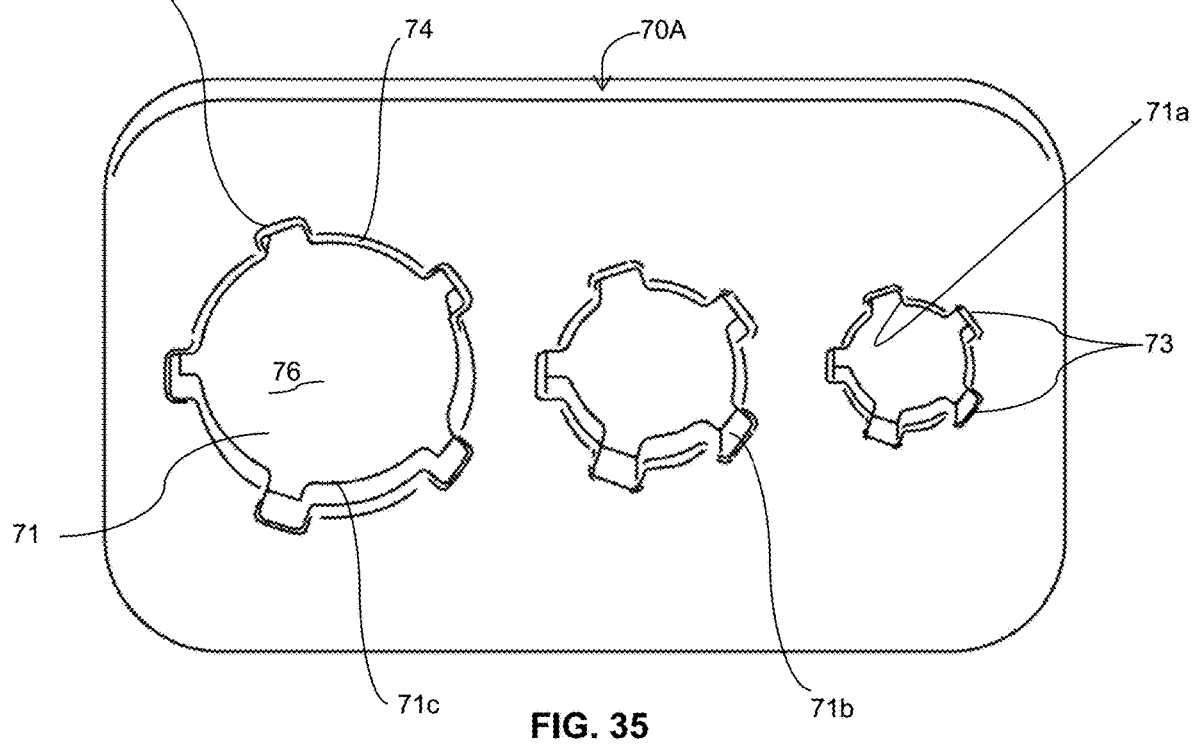
FIG. 35 shows a top perspective view of an alternate embodiment of a mounting tray which in this embodiment features three sequential sized apertures configured to frictionally receive respectively sized mounts and/or respective utensils directly.

FIG. 35 shows a top perspective view of an alternate embodiment of mounting tray 70A which is similar to that featured in FIG. 29a, but in this embodiment features three sequential sized apertures 71, with aperture 71a representing a reception aperture that is the smallest; 71b (medium sized), and 71c (largest sized). The apertures 71 in tray 70a thus extend inward into the tray's body, rather than having mount support projections extending up off the tray as in FIG. 29a. In both situations (tray 70 and tray 70A), however, the tray accommodation regions are designed to retain a corresponding sized mount 20 in position until intended for use either remotely off the tray or in a holding or transfer mode on the tray itself. Moreover, trays of the present invention are also configurable to frictionally receive respectively sized mounts and/or respective utensils directly, with the apertured embodiment tray 70A being particularly well suited for such direct utensil or utensil with collar tray reception as there is a nesting region provided in the body of the tray itself. Further, the tray reception is designed for single hand removal of components as in pulling on tab extension 176 to lift the entire structure (syringe assembly and collar for discarding after needle crush).

As further seen in FIG. 35, tray 70A is designed to support less mounts (three vs. ten mounts as featured in tray 70), which makes it well suited as a transfer tray for use in surgical operations and the like. The apertures in tray 70A, such as aperture 71a, feature peripheral wall extension recesses 73 that are designed with circumferential spacing in common with the circumferential spacing of ribs 27 about the annular core 21, such that upon resting a mount 20 in a corresponding aperture in tray 70A, the mount is held from rotation due to the ribs retention in the corresponding wall extension recesses 73. The wall extension recesses 73 can also be sized to provide the same means for preventing rotation upon receipt of, for example, a corner portion of a peripheral wall surface in a collar (e.g., collar of FIG. 10b) of the present invention, when placed in an aperture such as 71a. Further, between wall extension recesses 73, each aperture has a plurality of circle segments 74 (five segments adjacent the five wall extensions) that represent the inner most region of tray material relative to the formed apertures, and are preferably designed to come into friction contact with the annular core 21 of each mount placed in a corresponding aperture. Also, tray 70A features bottom floor 76 in each of the apertures that is an integral part of the tray body and thus is indicative that apertures 71 are not through-holes relative to the tray body in the embodiment of FIG. 70A, although other embodiments are inclusive of the providing of through-holes with reliance being placed on the frictional retention between the tray and mounts for retention relative to a vertical axis extending perpendicular to the tray and centered in each respective aperture 71.

Trays 70 and 70A are preferably formed of a sufficiently rigid plastic as to enable non-deflecting (non-sagging) transfer from one person to another, and thus are typically formed of a different material than mounts 20 or collars of the present invention, although alternate embodiments of the invention are inclusive of a common material in the tray relative to the noted collar and/or mounts (with an annular core 21 having common material as the tray 70A being one example). In embodiments of the present invention the tray is formed of, for example, PVC plastic material.

Figure 36:
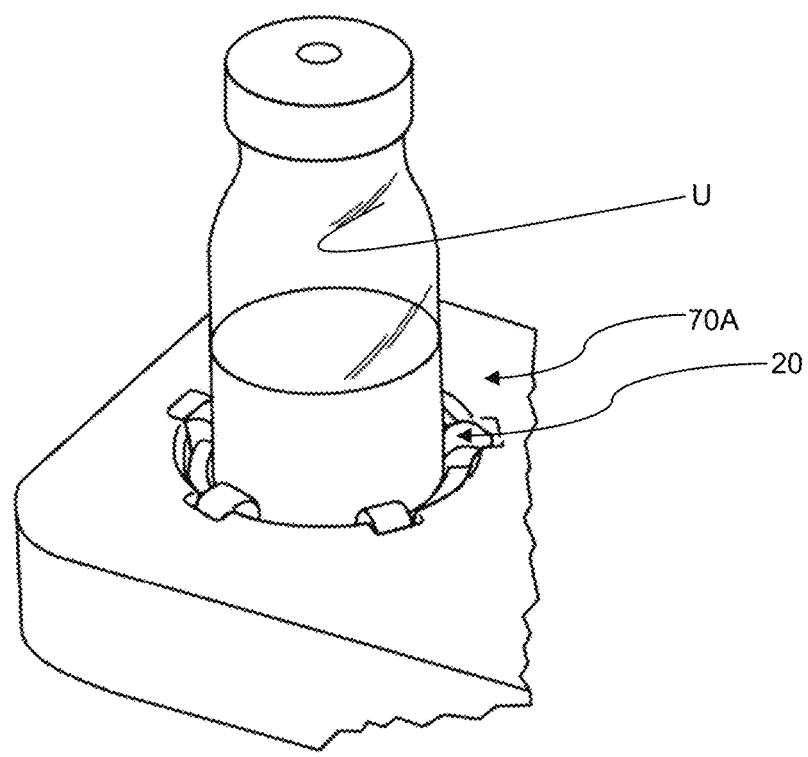
FIG. 36 shows a cut away portion of the tray of FIG. 35 showing the tray holding a combination of a mount and supported vial, with the combination being held in a snug, fixed from moving state (at least until the combination is pulled out, as the combination is removed as a unit due to the higher friction level between the mount and vial as compared to the friction level between the mount and conforming tray aperture).

FIG. 36 shows a cut away portion of tray 70A showing the tray holding a combination of a mount 20 and supported vial (utensil) U, with the combination being held in a snug, fixed from moving state (at least until the combination is pulled out, as the combination of the mount and vial is removed as a unit due to the higher friction level between the mount and vial as compared to the friction level between the mount and conforming tray aperture).

Figure 37:
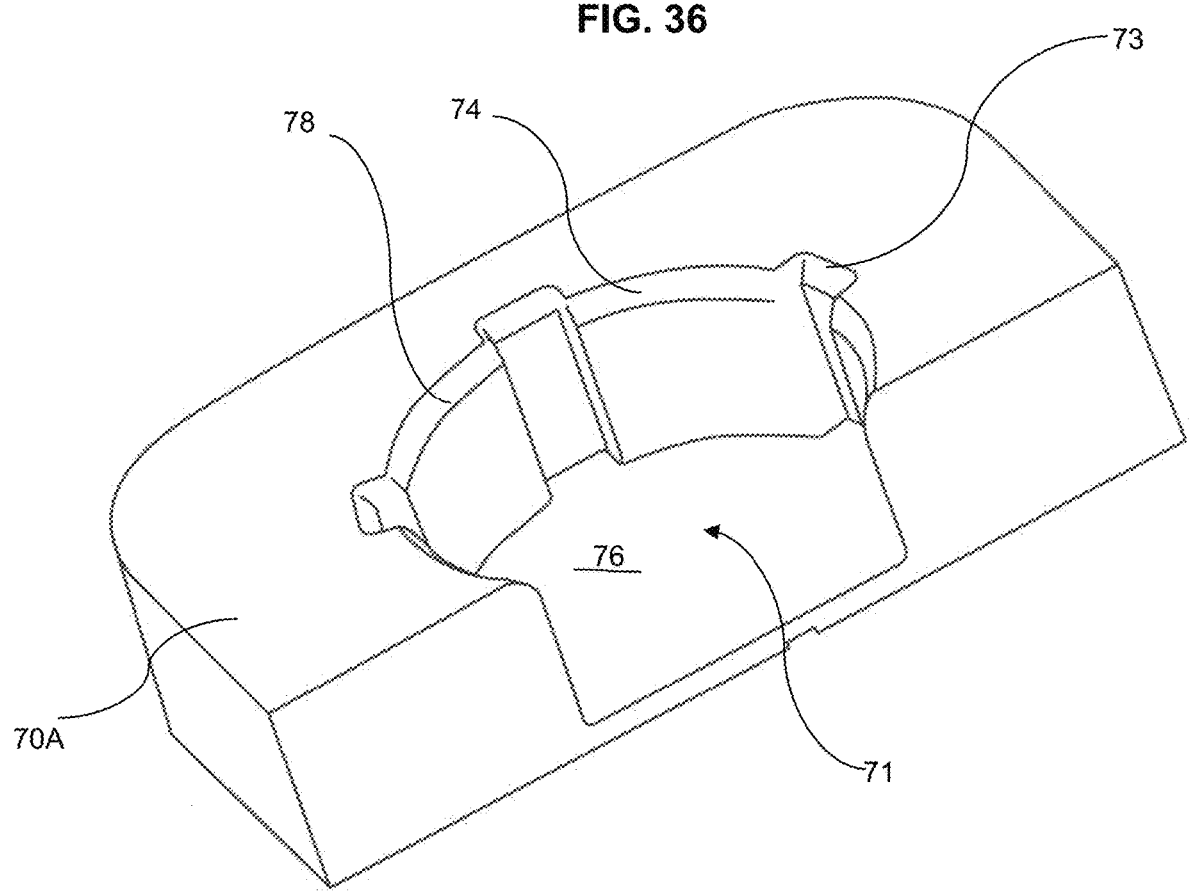
FIG. 37 shows a cut-away view of the tray of FIG. 35 showing the conforming apertures in the tray that are configured to receive internally a corresponding sized mount.

FIG. 37 shows a cut-away view of the tray of 70A showing the conforming apertures 71 with circular segments 74 between which are the radially outward extending ridge reception recesses 73, as well as bottom floor 76. FIG. 37 also illustrates the conical insertion edge or rim 78 which has its greatest diameter at the top of the tray and extends in oblique fashion downward and inward until reaching the interior most circle segment walls 74 of the tray. The upper conical rim 78 facilitates the slide-in insertion and centralization of the mount and associated utensil support (or collar and associated utensil support). As such, it only extends for a minor percentage of the depth of the aperture, as in 10 percent or less.

Figure 38:
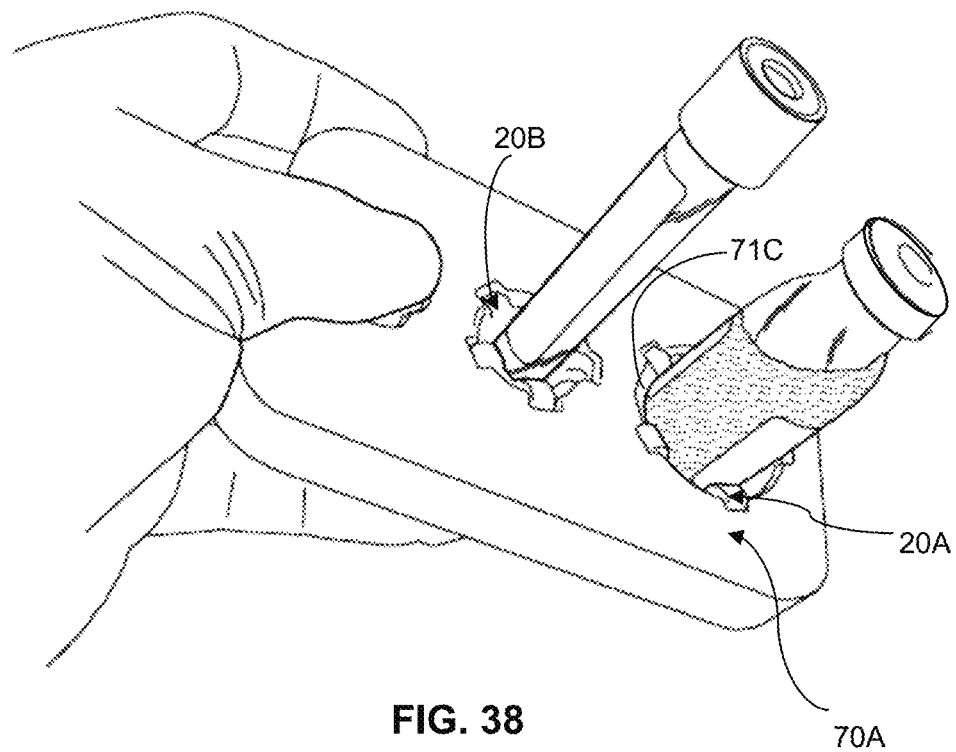
FIG. 38 shows the mounting tray supporting the vial of FIG. 35 plus the smaller (non-capped) end of a specimen tube, with the remaining aperture providing a convenient finger (thumb) grasping location.

FIG. 38 shows the mounting tray 70A supporting the vial and mount 20A combination of FIG. 36 in aperture 71c, plus the smaller (non-capped) end of a specimen tube ST and mount 20B in aperture 71b, with the remaining aperture 71a, providing a convenient finger (thumb) grasping depression location to facilitate single hand tray transfer.

Figure 39:
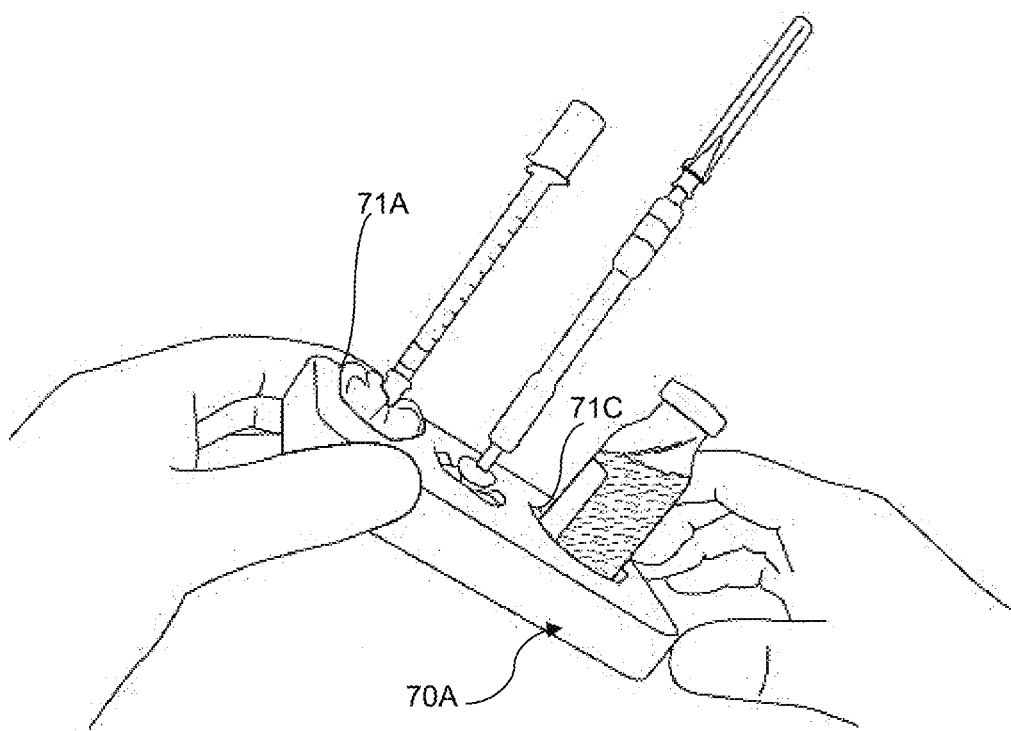
FIG. 39 shows a view similar to FIG. 38, but with each of the three apertures of the tray occupied, and a user having a side periphery of tray passing grip.

FIG. 39 shows a view similar to FIG. 38, but with each of the three apertures of the tray occupied, and a user having a side periphery of tray passing grip. While three apertures 71 are shown in FIG. 39, less or more of such apertures are possible, inclusive of multiples of common sized apertures on a common tray base 70A rather than the earlier described different sized apertures 71a to 71c. In FIG. 39 tray 70A is shown functioning as a mount holder and utensil retentioner as well as a passing tray when so desired. That is, tray 70A has its aperture 71c with a mount hold on a vial in similar fashion as shown in FIG. 36. However, its middle positioned aperture has an aperture configuration designed to receive (and preferably preclude rotation) of a syringe with grasping collar (e.g., collar 11A) attachment, such as that shown in FIG. 23B (with less or no exposed needle length to ensure no needle tip contact with the tray) or in the upper portion of the below described FIG. 60. As such, the size of middle aperture 71b may be smaller or equal to that of aperture 71a (rather than larger than 71a as described above) in an effort to have an aperture well suited to receive the desired collar embodiment, with the type of utensil received by tray 70A being designed, for example, to match with a planned usage sequence of medical utensils, as in use of the syringe shown in the middle position, and then a follow up medical step involving drawing medicament from the bottle in aperture 71c using the utensil provided in aperture 71a and then using that syringe.

In FIG. 39, the above noted different medicament syringe is shown received within the end aperture 71a, and the aperture 71a is shown configured for reception of a collar provided at the end of the syringe as, for example, collar 40 of FIG. 18, which is shown in the below described FIG. 42 as being mounted to the needle assembly end of a syringe. Thus, the aperture 71a can be designed as a universal collar and mount aperture having the five rib reception extensions 73 that are also sized to frictionally receive and retain (both vertically and rotationally) a collar. Alternatively, one or more of the apertures can be dimensioned, not to match the configuration of a mount, but for specific accommodation of a collar configuration, as in an aperture having a side wall with extensions that are designed to match the corner concavities of the collar such as that shown in FIG. 10A, with an otherwise general four sided recess tray recess designed to frictionally retain and conform in length with each generally straight segment wall shown in FIG. 10A, between the corner concave recesses.

Figure 40:
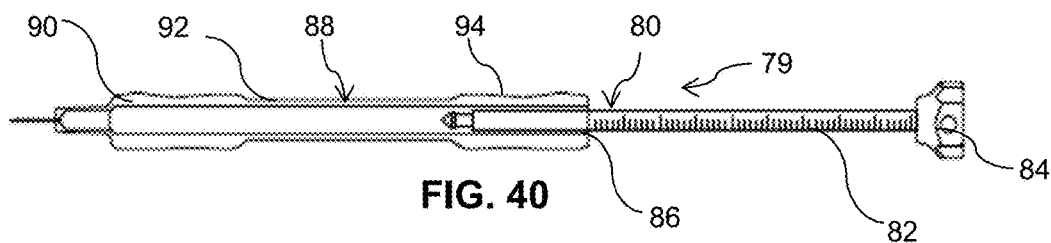
FIG. 40 shows a syringe with a modified plunger base featuring an added or one piece gripping collar of the present invention as well as a dumbbell shaped grasping device for the syringe cylinder.

FIG. 40 shows syringe assembly 79 featuring syringe 80 with a modified plunger 82 featuring, at one end, an added grasping collar 84, which can represent a snap-on collar featuring a collar of, for example, FIG. 11 configuration with open top rimmed end that is flexible enough to receive an inserted plunger flange (such as the circular flange located to the far right of the syringe of the below described FIG. 45). In an alternate embodiment, a one piece gripping collar forming a monolithic unit with the plunger 82 itself can be utilized (in similar fashion to the integrated plunger end shown in FIG. 48 as described below). FIG. 40 also shows, extending over the syringe cylinder 86, a grasping collar 88 in the form of an elongated dumbbell elastomeric shaped sleeve comprised of a needle end enlarged portion 90, an intermediate extension portion 92, and an opposite enlarged portion 94 similar in configuration to that of the needle end enlarged portion 90. Collar 88 is provided with a central through-hole designed to receive in slide-on gripping fashion the cylinder 86 of syringe or collar 88 can be molded over cylinder 86.

Each enlarged portion 90, 94 represents an adaptation of the gripping sleeve device for precision instruments described in U.S. Pat. No. 8,745,825 issued on Jun. 10, 2014 (US '825), and which patent is hereby incorporated by reference in its entirety for background purposes. That is, each enlarged portion has an outer surface with the finger contact regions described in US '825 that provides for enhanced finger manipulation, both with respect to longitudinal advancement or retraction in the direction of needle insertion, but as well as rotation of the syringe. The elongated dumbbell shape also facilitates handing off the utensil from one person to the next or one hand to the other, as the length of extension portion 92 is sufficient for finger grasping without contacting the two, opposite end enlarged portions 90 and 94 and also in a fashion that avoids interfering with extended plunges. In addition, the enlarged dumbbell ends 90 and 94 provides for lifting the needle away from a contaminated surface and ready pinch pick up due to the lifted off surface arrangement provided by enlargements 90 and 94. Further, the inclusion of the dumbbell sleeve with enlarged sleeve portion 94 provides a grasping location that avoids the need for a syringe cylinder end flange. Also the inclusion of grasping collar 84 removes the requirement for a free end plunger flange.

Figure 41:
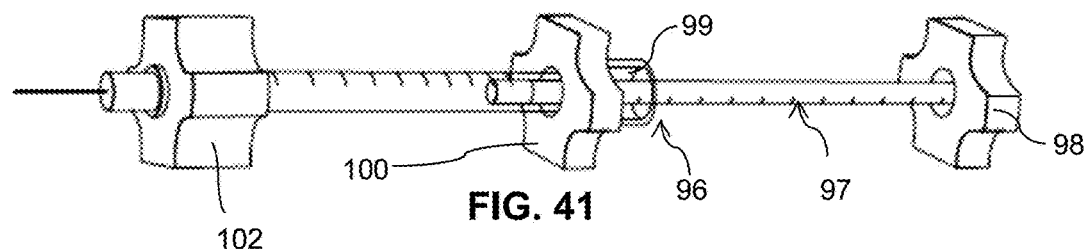
FIG. 41 shows another embodiment of the present invention featuring a set of different collars inclusive of a first smaller thickness grasping collar at the plunger base, a second, similar smaller thickness collar at the syringe's cylinder base, and a third, larger thickness collar at the needle support end of the syringe cylinder.

FIG. 41 shows another syringe assembly 96 embodiment of the present invention featuring a syringe 97 with a set of different collars inclusive of a first, smaller thickness grasping collar 98 at the plunger base, a second, similar smaller thickness collar 100 at the syringe's cylinder base, and a third, larger thickness collar 102 at the needle support end of the syringe cylinder. The smaller collars have interior apertures (through-holes) suited for stretch over (e.g., snap-on or just slide over) retention to their respective syringe sights (as in a sufficiently flexible material collar with an aperture that snaps over and engages the circular flange located to the far right of the syringe of the below described FIG. 45 including expansion over a plunger's flanged end or simply slides over a flange less plunger end). In addition, the same collar (collar 100) with its flexibility and suitably sized aperture can slide over and engage with the base of the cylinder of the syringe 97 of needle assembly 96.

As seen, each of the flexible grasping collars 98, 100 and 102 feature a peripheral configuration similar to that of FIGS. 10a and 10b, inclusive of four concave recesses at corners of the grasping collar, two opposing longer length generally straight or slightly curving (e.g., a radius larger than that of a circumference contacting the outermost points of collar 98, 100 or 102), and two opposing also generally straight or slightly curving (see above) shorter length sides. Collars 98 and 100 can be of the same configuration. Also the thickness of the thinner collars 98 and 100 can be, for example, ½ of that of the thicker collar 102 (e.g., a thickness value of, for instance, 6 to 9 mm for the thinner collars 98 and 100 which is suitable for the small volume (e.g., a cylinder volume of, for example, 0.5 ml (or cc) to 10 ml) syringe 96 shown). Also, the concave recessed corners and adjacent projections resulting in the noted shorter and longer generally straight or slightly curved ridge sides provide for ready finger pinching external to the cylinder of the syringe and multiple finger grasp locations for a transfer (e.g., one person pinching and holding one of collars 98, 100 and 102 and the other person receiving the syringe with the needle in a safe location by grasping one of the remaining two collars not already grasped). The collars also are well suited to maintain the needle of the syringe suspended above an underlying potentially contaminated surface.

Figure 42:
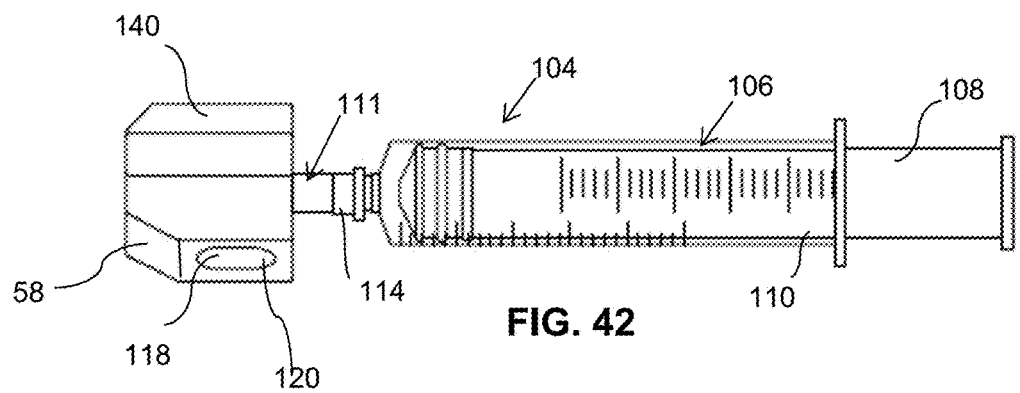
FIG. 42 shows the collar of FIG. 18 in an initial slide on position relative to the needle assembly of a syringe.
Figure 43:
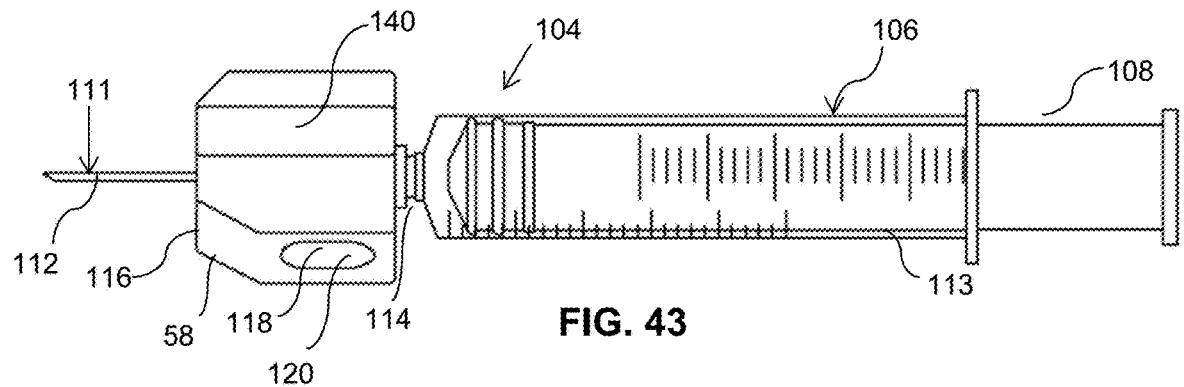
FIG. 43 shows the collar of FIG. 42 in a final resting position over the base of the needle assembly and with a predetermined length of needle extending outward away from the free end of the collar with slanted exterior surface.

FIG. 42 shows an additional syringe assembly 104 under the present invention featuring a syringe 106 comprised of a plunger portion 108, a cylinder portion 110 (e.g., a higher volume cylinder as in, for example, >10 ml to 400 ml), and a needle assembly 111, with the latter having a needle 112 and needle base hub 114. In FIG. 43, syringe assembly 104 is shown further comprising collar 140 (see FIG. 18) having its aperture set (42, 42' and 42") in position for a slide on connection with the above described components of needle assembly 111 as in the needle associated with a 20 ml to 50 ml syringe. As seen, collar 40 in FIG. 42 has a similar external periphery as that of the above described collar 102 with its four corner positioned concave recesses and short and long sides extending between the corner concave recessed and in common opposing fashion (i.e., short-to-short generally straight ridge sides opposing, and long-to-long generally straight sides opposing). Collar 140 in FIG. 42 is also shown with the above described sloped surface 58 which facilitates needle tip and needle orientation relative to the skin surface to receive the needle (this being in addition to the offset finger pinch grasping potential when holding, passing or receiving the needle assembly 104).

FIG. 43 shows the collar 146 of FIG. 42 in a final resting position over the base of the needle assembly 111 and with a predetermined length of needle 112 extending outward away from the free end 116 of the collar 40 with slanted exterior surface 58. FIG. 43 further shows the tapered surface 58 being formed on the longer opposing generally straight side which further includes a finger depression recess 118 (same as the oval recess depression 45 in FIG. 10a) along the non-slanted portion 120 that extends from an end of tapered surface 58. As also seen in FIG. 43, the outer circumference of the collar 40 has a larger diameter than that of the syringe cylinder (even the larger volume syringe cylinder) as to provide for offset grasping away from the needle, etc.

Figure 44:
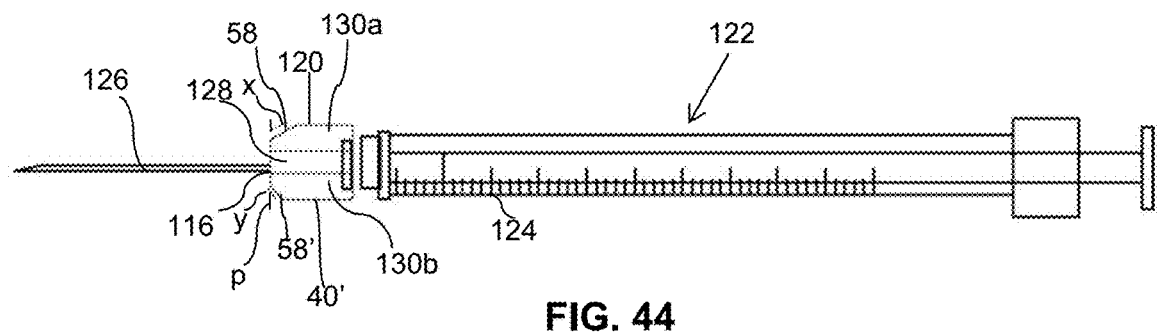
FIG. 44 shows a similar view as FIG. 43 but with a different, smaller volume cylinder syringe and with a longer needle extension out from the collar secured to the syringe's needle assembly.

FIG. 44 shows a similar view as FIG. 43 but with needle assembly 122 featuring a different, smaller volume cylinder 124 and with a longer needle extension 126 out from the collar 40' secured to the syringe's needle assembly. FIG. 44 also provides a different viewpoint wherein there can be seen the short side ridge 128 of the opposing short sides ridges. Also, in this embodiment, collar 40' is similar to that of FIG. 18, but features a second, shorter length oblique surface 58' on the one side opposite the long or wider width ridge side in which oblique surface 58 extends. For example, concave recesses 130a and 130b extend in longitudinal fashion for the full entire length of collar (longitudinal is perpendicular to plane P that extends flush on free end 116 of collar 40'). Suitable angle ranges for angles X and Y defined by plane P and the respective oblique side (58, 58') range from 10° to 80° with X preferably being equal to or greater than angle Y shown in FIG. 44.

Figure 45:
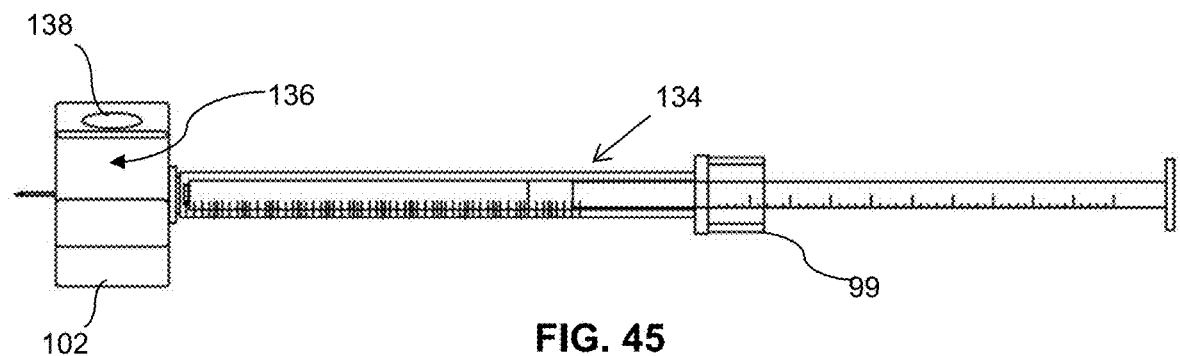
FIG. 45 shows an alternate arrangement featuring a similar volume cylinder syringe as in FIG. 44, but with a collar having the configuration shown in FIG. 10b.

FIG. 45 shows an alternate needle assembly 134 arrangement featuring a similar volume cylinder syringe as in FIG. 44, but with a collar 136 having the configuration shown in FIG. 10b. As further shown in FIG. 45, collar 136 comprises a finger depression recess 138 (in common with depression 45 shown in FIG. 10a and with an illustrative depression level of 0.5 mm). This finger recess can help a user control the desired tilt for insertion of the only partially visible needle shaft extending out from the collar.

Figure 46:
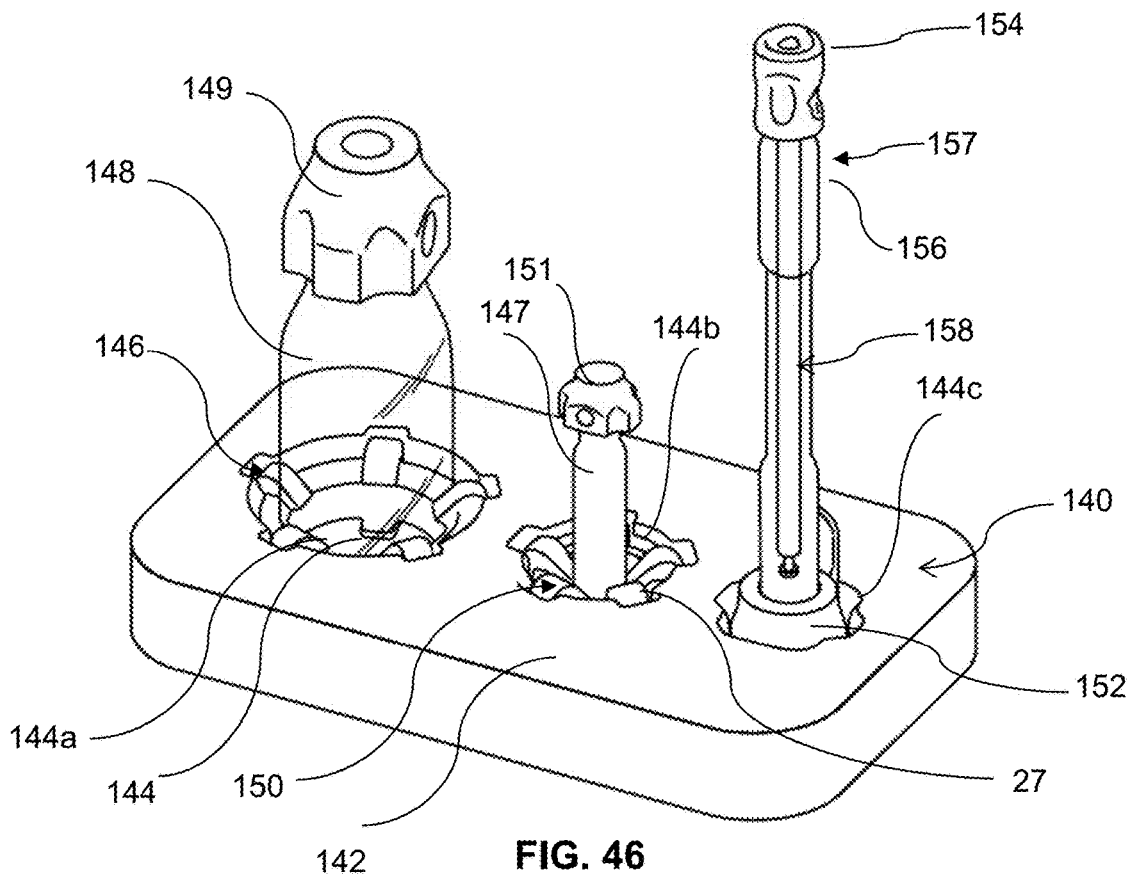
FIG. 46 shows a tray similar to that of FIG. 35 with the base mounts of two of the three utensils secured in the corresponding tray mount reception apertures, as well as an additional needle capping and crushing collar base component received in a corresponding collar tray reception aperture; and a grasping collar provided at the top of each utensil, including an open top collar for the far left utensil, a closed top cap configured collar for the interior utensil, and a grasping collar at the top end of the syringe shown received in the far right tray reception aperture.

FIG. 46 shows tray 140 (similar to that of FIG. 35) comprising base body 142, having apertures 144, with a largest diameter aperture 144a, an intermediate aperture 144b, and a third, smallest aperture 144c. Apertures 144b and 144a are similar to the above described counterpart apertures 71c and 71b, but aperture 144c represents an aperture configured for specific friction retention of the below described capping needle and crush collar (152 in FIGS. 52 and 53 and hereafter referenced just as "crush collar"), which crush collar generally has a FIG. 11 configuration. Aperture 144c thus has a unique shape designed to conform with the exterior periphery of collar 152 with its long and short ridge sides and in between cavities.

FIG. 46 further shows a kit combination embodiment under the present invention involving tray 140 plus one or more additional components. While a kit combination is described for that which is shown in FIG. 46, the present invention described components can be provided in a variety of kit forms including combinations involving some or all of the component categories described herein; such as i) mounts (annular collar and ribs combination), ii) container collars (as in vial or bottle collar, with closed top or open top of various aperture sizes and configurations), iii) syringe collars (collars on a syringe plunger, syringe cylinder, and/or needle assembly) and iv) haptic collar(s) such as for catheter use, as a few examples. In the FIG. 46 embodiment, the additional components include a larger sized base mount 146 (having the above described mount 20 configuration) supporting the base of a larger sized bottle 148, with the mount and bottle nestled within conforming aperture 144a. In addition to base mount 146, the kit includes a FIG. 11 configured collar 149, which is shown as a cap to bottle 148 and as having an open top (suitable for syringe insertion as described below).

The middle positioned aperture 144b also is configured to receive a corresponding sized base mount 150, which is supporting the base of a sample vial 147 having a smaller version FIG. 11 collar 151 which in this case has a closed top. Thus, the two larger apertures 144a and 144b have apertures designed specifically for receiving the mount ribs 27 in extension recesses, while the smallest aperture 144c is configured differently, with an aperture configured to accommodate needle support-and-crush collar 152 received in the friction fit collar tray reception aperture 144c.

Additional components associated with the kit involving tray 140 include syringe assembly 157 comprising syringe 158 as well as plunger end grasping collar 154 and dumbbell sleeve 156 provided along the cylinder of syringe 158 (provided by a slide fit over the cylinder or an overmolding integrated combination). The kit associated with tray 140 can be one that is functionally coordinated, as in a liquid bottle medicament supply 148, for drawing liquid medicament solvent therefrom, with syringe 158 (after pulling the syringe from collar 152 (in a not yet needle crush state) and inserting it into the open top of collar 149) and then passing the drawn liquid medicament to the powder storing vial supported in aperture 144b by puncturing the top seal of collar 151 whereupon the powder and medicament solvent can be mixed and drawn up for patient insertion and then, upon patient treatment completion, the syringe 158 is returned to collar 152 whereupon the enlarged lower end of the dumbbell sleeve (with associated enlarged "saddle horn" projection (described in US '825)) is rotated so as to avoid an interior projection in collar 152, whereupon a downward force is applied to move the syringe so as to crush the needle. The entire syringe collar and crush collar can then be discarded with a covered and crushed needle.

Figure 47:
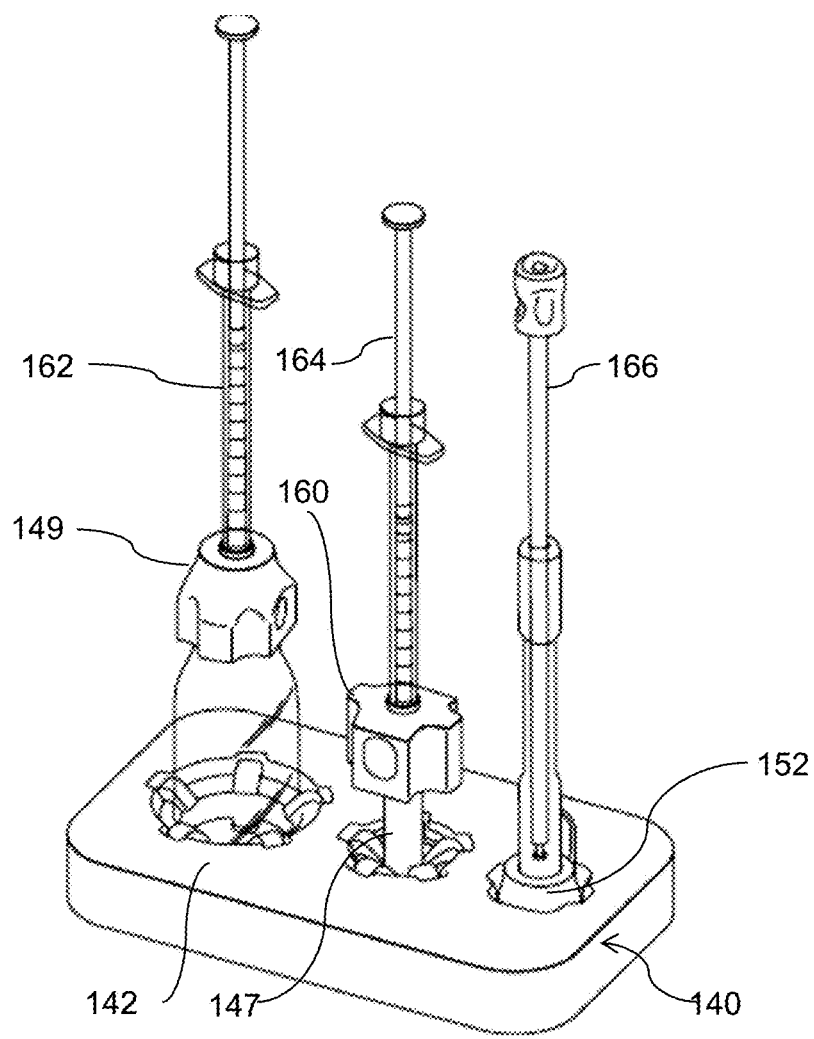
FIG. 47 shows a similar view as FIG. 36, but with a FIG. 10a collar embodiment for the intermediate utensil, and the added feature of the far left and intermediate collars showing syringe needle reception with the needle in each passing through and being supported by the receiving collar mounted on the utensil below.
Figure 48:
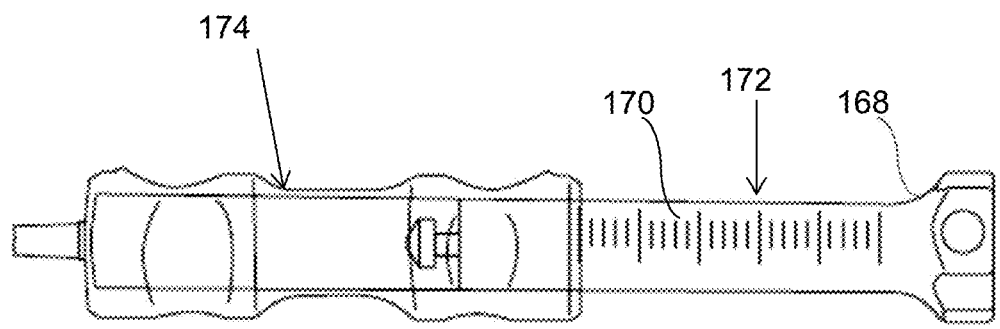
FIG. 48 shows an alternate embodiment of the invention featuring an integrated (unitary or monolithic) grasping body formed integrally with a plunger of a syringe and of a common material as well as a non-monolithic grasping collar in a dumbbell shape provide over the cylinder of the syringe shown, and with volume demarcation provided on the plunger body rather than the dumbbell sleeve covered syringe cylinder.

FIG. 47 shows a similar view as FIG. 46, but in different kit form as it comprises, instead of collar 151, a FIG. 10a collar (160) embodiment is attached to the top of vial 147 as the intermediate utensil. There is also shown in FIG. 47, the added feature of the far left and intermediate syringes 162 and 164 with the needle of each of syringe 162 and 164 shown passing through and being supported by the receiving collar mounted on the utensil below. As above, the kit associated with FIG. 47 can be a functionally coordinated kit, with, for example, a pre-filled syringe 166, and the other two syringes (once liquid medicament is drawn from the associated utensil), being used in a desired sequence of application on a patient. Further, each component supported on the tray is designed for single hand removal or insertion FIG. 48 shows an alternate embodiment of the invention featuring an integrated (unitary or monolithic) grasping body 168 formed integrally with a plunger 170 of the illustrated syringe 172. That is, FIG. 48 shows a grasping collar 168 that is formed as a monolithic component of the base end of a syringe plunger and preferably of a common material (e.g., one polymer plastic molding of collar 168 and plunger body). Additionally, syringe 172 features a cylinder with a dumbbell grasping sleeve 174 which is a non-monolithic grasping collar in a dumbbell shape (and having the characteristics described above for grasping collar 88 in FIG. 40) provided over the cylinder of the syringe shown. Also, rather than demarcations on the covering dumbbell collar, volume demarcations are provided on the plunger itself. This arrangement is particularly suited for high viscosity liquids requiring a high plunger draw force.

With reference to FIGS. 49 to 53 there is described the syringe support/needle crush collar 152 briefly described above. With reference to FIGS. 52 and 53 there is shown collar 152 alone with FIG. 52 showing a perspective view of collar 152 and FIG. 53 showing a cross-sectional view with the collar half removed being positioned away from tab extension or clip 176.

As seen from FIG. 52, collar 152 has the FIG. 11 configuration, but for the added tab extension or clip 176, as well as preferably added revisions with respect to providing a needle blockage base for facilitating needle crushing when so desired and an added interior projection 182. FIG. 52 further shows crush collar 152 with an open top 178 preferably having a slight conical alignment ledge 180 which tapers inward and downward from the top face of collar 152. In the interior cavity 181 shown in FIG. 53, there can be seen inward projection 182 that extends inwardly into cavity 181 away from tab extension 176 as to provide for pre-crush axial resistance during syringe support in collar 152. Floor 184 is preferable formed of a sufficiently hard plastic or is supplemented with a metal disc or the like that is supported by the circular face associated with floor 184. The harder plastic can be representative of the entire collar 152, but since having a flexible collar 152 that can be pliable to facilitate positioning of utensils in a support relationship is desirable, a dual plastic molding relationship can be implemented such that the floor is of a different, harder plastic or the aforementioned metal disc insert can be utilized (i.e., insertion of a thin metal, circular disc to conform to and cover floor 184). The collar 152 configuration and dimensions is suited for receiving collar 192 and thus is preferably similar to those featuring a "large mouth" reception aperture such as featured in FIG. 59 and FIGS. 128a and 128b described below.

FIG. 52 further illustrates in common fashion with FIG. 11 that the exterior side wall periphery of collar 152 is comprised of a series of concave depressions 186 separated by wall projections 188. As seen in FIGS. 11 and 52, the concave depressions can come in different length and width sizes, with a plurality of narrower and higher extending depressions 186A (higher extension up into the conical top region 190 of collar 152), separated by shallower height concave depression 186B, with the latter also having finger depression recess 187 (on the side opposite the tab extension 176). The ridge line projections 188 include a similar shaped series of such ridge lines (188A, 188b . . . ) that provide for offset finger grasping with any two of such projections with finger nesting in the adjacent concave depressions.

Figure 49:
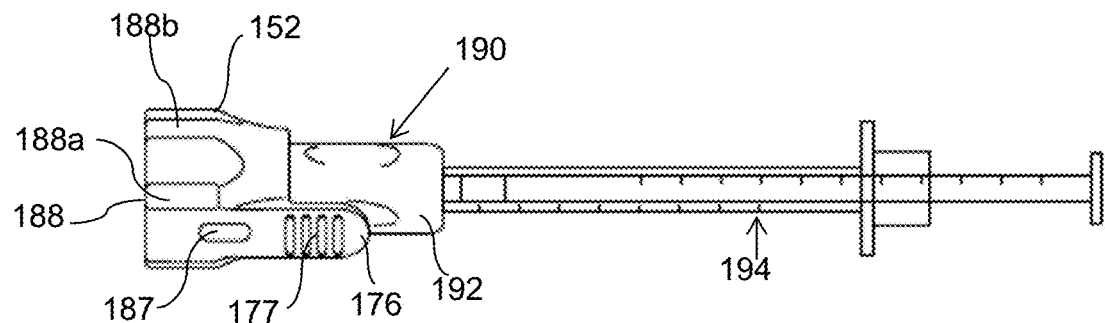
FIG. 49 shows an additional embodiment of the present invention featuring a capping and needle crush collar base component, noted in FIG. 46 above, working in combination with a needle assembly reception collar that is received by the capping and crush collar ("crush collar" for shorthand reference).

FIG. 49 shows an additional embodiment of the present invention featuring needle crush collar 152 providing support to syringe assembly 190. As shown, syringe assembly 190 has grasping collar 192 formed at the needle assembly end of syringe 194 (of syringe assembly 190) working in combination with the receiving crush collar. Grasping collar 192 represents an adaptation of the gripping sleeve device for precision instruments described in the earlier noted U.S. Pat. No. 8,745,825 issued on Jun. 10, 2014. The adaptation in this case includes having the interior through-hole having a diameter or diameters to conform to the diameter(s) associated with the needle assembly of syringe 194. Due to the non-symmetrical configuration of collar 192 (e.g., the saddle horn projection 191 in FIG. 150), the plateau of the sleeve or handle will engage inward projection 182 protrusion(s), which will block further penetration into the cap. When returning after use the syringe with the sleeve may be rotated such that protrusion 182 will meet a smooth surface of syringe assembly 190 and therefore be able to be depressed deeper into the crush collar and, after needle crushing, disposed, safely, as a unit (syringe and cap connected) into a disposal bin. Thus, a single hand needle decapacitating safely system is provided.

Figure 50:
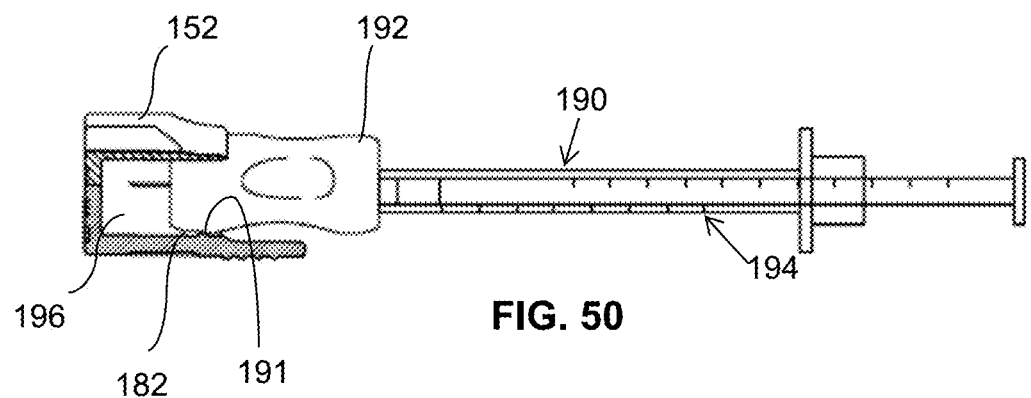
FIG. 50 shows a partially cut away view of that which is shown in FIG. 49 with the crush collar receiving the grasping collar at the distal end of the syringe and in a pre-needle crush state, due abutting projection alignment for projections found on the crush collar interior and syringe grasping sleeve exterior.
Figure 51:
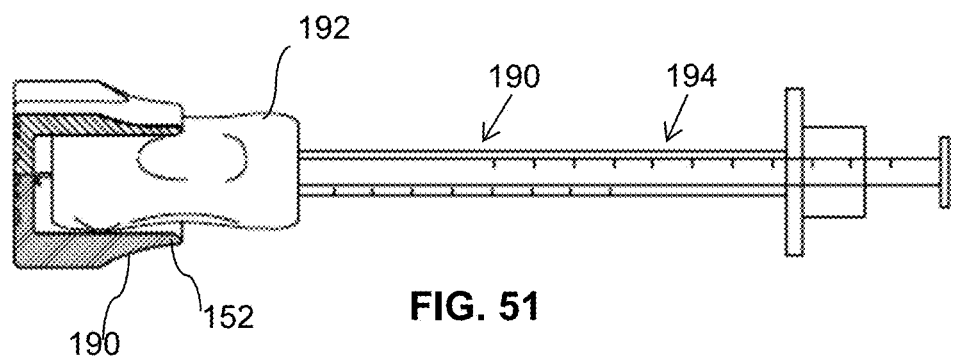
FIG. 51 shows the same view as FIG. 50 but with the syringe assembly and collar having been compressed together fully leading to the bending of the free portion of the needle extending out of the grasping collar on the syringe; in this state the entire assembly is suited for discarding in a needle collapsed, safe state.

With reference to FIGS. 49 and 50 (with FIG. 50 providing a cut-away view of syringe assembly 190 in a support (non-needle-crush) mode), there is shown needle 196 in a suspended state above floor 184 of collar 152. There can further be seen the syringe support function provided by collar 152. As further seen from FIG. 49, tab extension 176 includes finger enhanced friction ridges 177 formed in the body of tab extension on the exterior side and above finger depression recess 187. This finger friction enhancement facilitates the ability to grasp collar 152 and the supported syringe either for movement to or from a support surface or for pulling out (or placement in) of collar 152 in a conforming tray aperture such as 144c in FIG. 46, or the final discard step described above. The needle crush conversion can be seen by a comparison of FIGS. 50 and 51 wherein the latter shows the crush state of the needle, and with floor 84 showing a partially harder material section via different cross-sectioning.

FIG. 54 shows a perspective view of a combination horn collar and syringe assembly 197 comprising syringe 210 and a horn ended collar 198 of the type shown in FIG. 19. Collar 198 is shown as comprising a syringe cylinder engagement portion 200 which has an axial bore of a diameter suited for engagement with the cylinder portion 208 of the supporting syringe 210 (or an enlarged end of a dumbbell shaped collar). As seen from a comparison of FIG. 19 and FIG. 54, collar 198 can extend for the full sleeve length or a portion of it, with the FIG. 54 embodiment showing coverage of only the needle end portion of cylinder portion 208. The collar's cylinder engagement portion 200 is of an outer diameter smaller than the outer periphery of the free edge 202 of horn portion 204, which horn shields the needle 209 both circumferentially and axially (when the horn is in an uncompressed state). Also, collar 198 extends longitudinally (or axially) along the length of the syringe into an intermediate, hour-glass shaped portion 205 (having the minimum diameter portion 206) which covers the interface region between the syringe's cylinder and the base region of the needle assembly supporting needle 209. Horn portion 204 extends distally away from the intermediate region 205, and has a rapid diametrical expansion from its interface with the intermediate region. For example, an outer peripheral edge 202 diameter of 6.0 mm to 2.5 cm is suitable for some intended uses of the present invention. In addition, edge 202 is preferably of a skin contact thickness of 1.0 mm to 2.0 mm, and the diameter can be relied upon as a demarcation means, as in a border region demarcation means for skin removal out from an area of highest concern (e.g., as by a physical marking along the edge of edge 202). Further this demarcation can be used as a boundary region to gauge mole growth or the like over a period of time by photo comparison example. FIG. 54 also shows suction apertures 62, which are optional in some instances in the sense that suction breakage generated when apertures 62 are not present can be achieved by a suitable tilting for some configurations of horn collar 198, but not as easily.

As further shown in FIG. 54, syringe assembly 212 includes the aforementioned syringe 210 plus proximal grasping collar or sleeve 214 representing, again, an adaptation of the sleeve of a U.S. Pat. No. 8,745,825 grasping sleeve. In addition, to the dumbbell shaped sleeve 214, there is provided on syringe 210 plunger end collar 215, also representing an adaptation of the above referenced US '825 patent's sleeve. As with other embodiments of the invention, the dumbbell collar and plunger collar avoid having to have the complexity associated with having flanging on the cylindrical end and plunger end as found on prior art syringes.

FIG. 55 shows a view similar to FIG. 54 but with the syringe 216 having an entirely exposed dumbbell syringe grasping collar 218 (similar to that described for FIG. 40). Thus, both enlarged ends are exposed instead of the less exposed collar 214 in FIG. 54.

Figure 56:
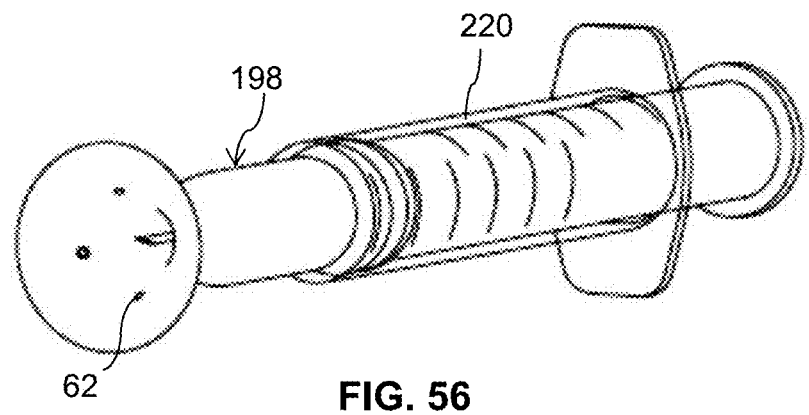
FIG. 56 shows another view of the horn shaped collar of FIG. 19 and FIG. 54 mounted on the needle assembly at the distal end of a large volume cylindrical syringe.

FIG. 56 shows another view of the horn shaped collar 198 of FIG. 54 (and FIG. 19) and mounted on the needle assembly at the distal end of a large volume cylindrical syringe 220.

Figure 57:
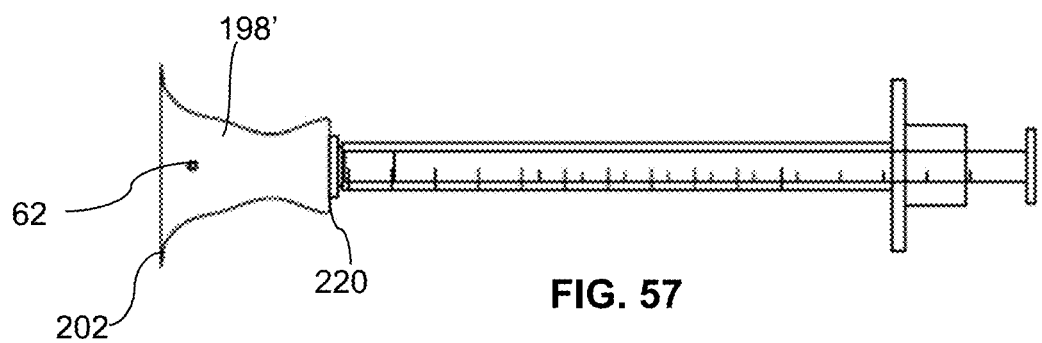
FIG. 57 shows a similar view as that in FIG. 56, but with the horn collar of FIG. 19 mounted on an intermediate volume syringe, and with the horn collar having a lower base strength.

FIG. 57 shows a similar view as that in FIG. 56 but with the horn collar 198' being of a modified design having a shorter length cylinder engagement portion 220 as compared to the longer cylinder engagement portion 200 in FIG. 54.

Figure 58:
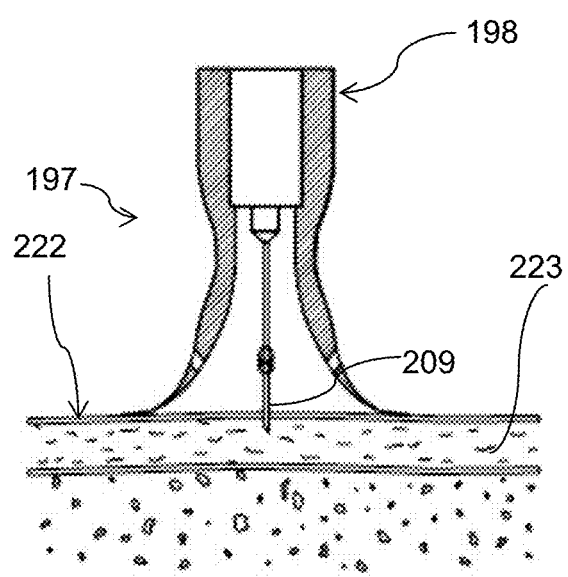
FIG. 58 shows the horn collar with just the needle assembly portion of a syringe and the needle in a perpendicular puncture state below the outer stratum corneum of the recipient's epidermis.

FIG. 58 shows a cut-away view (only the needle portion of the syringe shown) of the combination syringe and horn collar 197, with the needle 209 in a perpendicular initial puncture state below the outer stratum corneum 222 of the recipient's epidermis, with the level of needle puncture below the stratum corneum into the lower layered area 223 being based on needle length, diameter and horn collar configuration. As seen the horn collar 198 provides for both positioning and a spring back tension that helps return the needle after a user compresses the horn collar to a desired extent. Horn collars can be provided with different compression levels by pre-designed based on thickness adjustment in the horn walls. As also shown in FIG. 58 the horn walls have a thicker higher section that leads to a lower thinner, flared section intended for skin contact.

Figure 59:
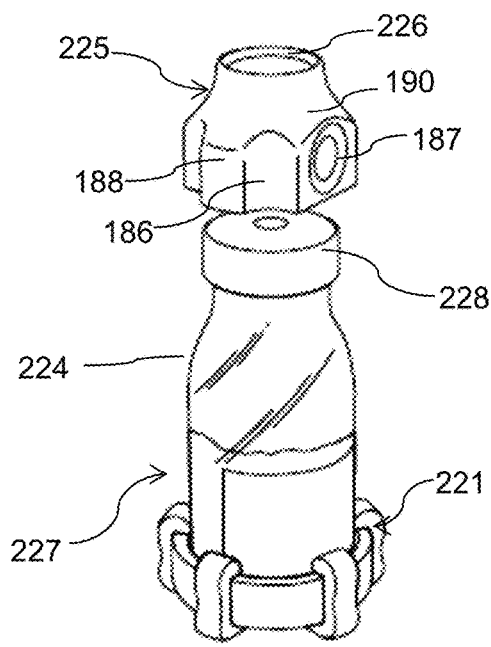
FIG. 59 shows a combination of present invention components, inclusive of a base support mount of FIG. 3a and the collar of FIG. 11 (just prior to vial top attachment), with the FIG. 11 collar in this embodiment having a fully open, rimmed top for receipt of a syringe assembly or other interconnecting component.

FIG. 59 shows a kit combination 227 of the present invention components, inclusive of a base support mount 221 of FIG. 3a configuration, which supports fluid containing sealed vial 224, and collar 225 of FIG. 11 configuration, (just prior to vial top attachment), with the FIG. 11 collar 225 in this embodiment having a rimmed open top 226 for receipt of a syringe assembly or other interconnecting component. As seen from FIG. 59, collar 225 has the attributes earlier described for the FIG. 11 and FIG. 52 embodiments, but is absent the tab extension of FIG. 52. Thus, collar 225 has axially extending peripheral concave recesses 186 extending up to the conical top 190 as well as the circumferentially spaced ridges 188 and the finger depression recess 187.

Figure 60:
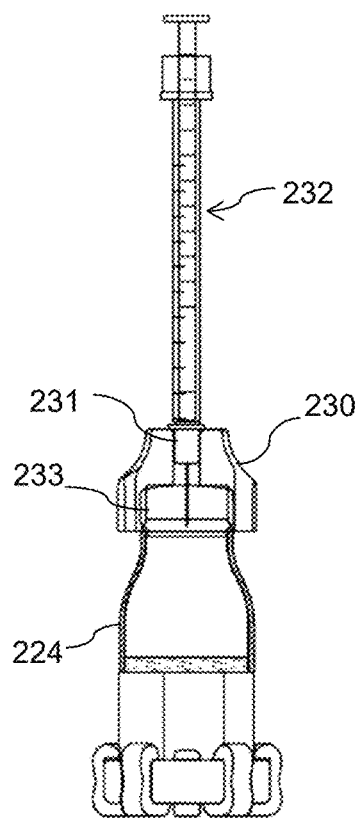
FIG. 60 shows a schematic line drawing showing the combination of the vial and a modified top collar, and the associated positioning of the syringe assembly.
Figure 60A:
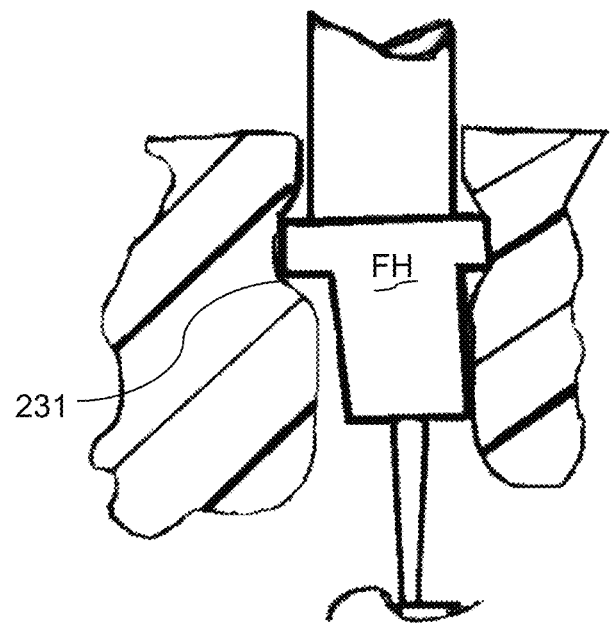
FIGS. 60a and 60b show a first embodiment deeper positioning of a hubbed flange of a needle, and 60b showing added radial groves in the collar cavity providing added snap-in positional needle length capability; this relationship also provides for improved syringe-to-bottle flexing as when trying to get access to the last amount of medicament in the bottle.
Figure 60B:
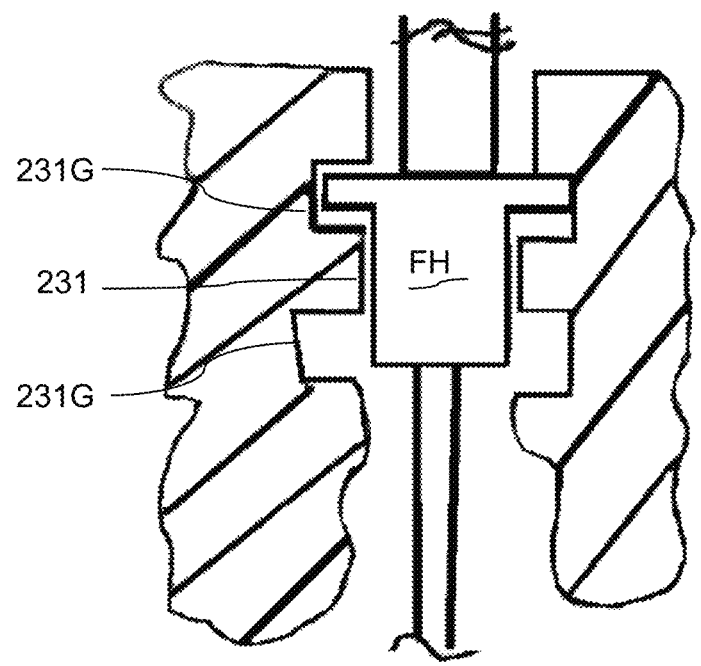

FIG. 60 shows a schematic line drawing showing a similar combination of vial 224 and a top collar such as shown in FIG. 59. As seen from a comparison of FIGS. 59 and 60, collar 230 has the same peripheral exterior as collar 225 in FIG. 59, but has a modified top region and interior cavity set up. That is, collar 230 has an upper smaller top aperture designed to receive directly syringe 232, which small top cavity 231 opens out in stepped fashion with enlarged diameter aperture 233 designed to provide a flex attachment (preferably non-threaded) to the vial top 228 (see FIG. 59). The combination of vial top collar and base mount shown in FIGS. 59 and 60 are representative of kit combinations within the above described potential kits based on the present invention described components (such kits can also include associated syringes, vials etc. in addition to the above described present invention component categories). Also, the combination of vial and syringe assembly in FIG. 60 can represent, for example, an insulin injection situation wherein after syringe 232 is engaged with collar 230, the syringe and vial may be single handedly tilted to receive the medicine. Also, as seen in FIGS. 60a and 60b flanged needle hub FH can have its upper flange sit on the top border of cavity 231 in collar 225. However, if there is desired to have the needle tip deeper in the bottle the flexible cavity wall can be expanded out to receive in a tighter squeeze fashion needle hub FH. This relationship also provides for controlled flexing and tilting of the needle within the bottle as when attempting to get remnants at the bottom of the bottle. Alternatively, as shown in FIG. 60b, cavity 231 can be provided with one or more radial grooves 231G, which provides for staged control of needle hub adjustment and needle tip extension in the bottle. The groove 231G and needle hub FH relationship also provides a good fulcrum location for needle tilting in the vial.

Figures 61, 62:
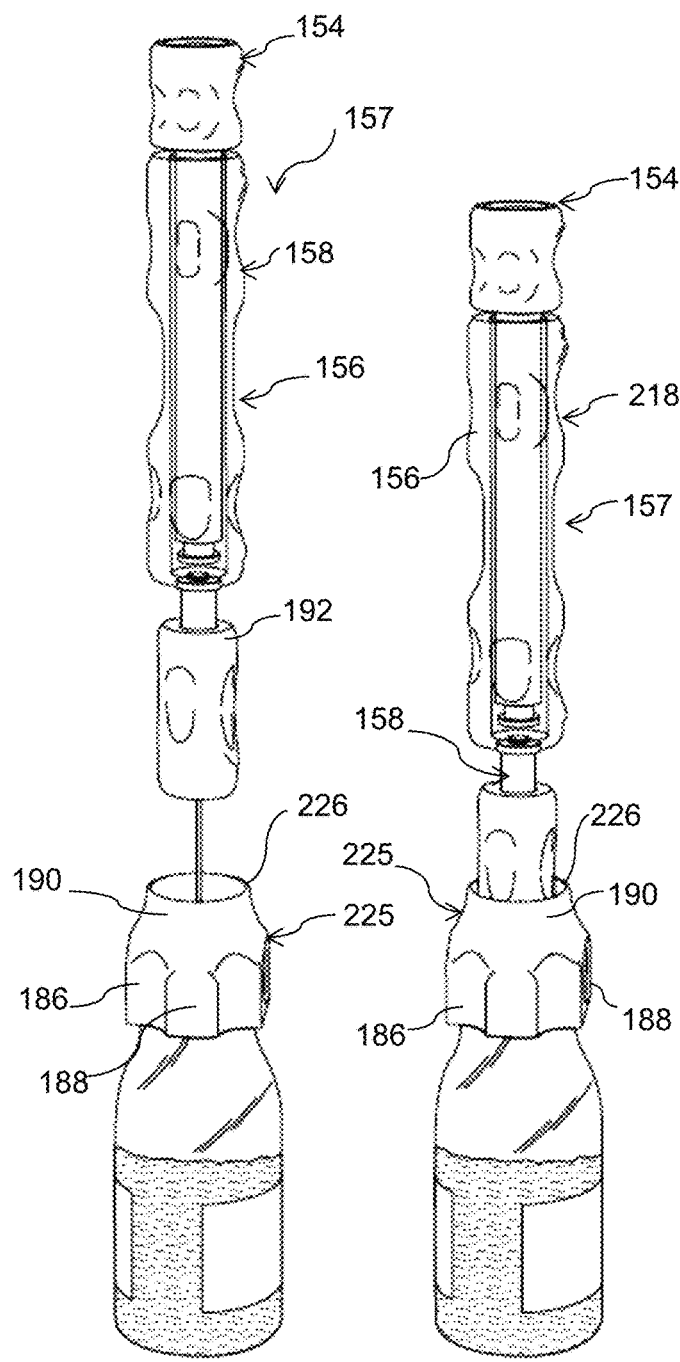
FIG. 61 shows a syringe assembly that includes a first grasping collar at the plunger base, a second grasping collar along the syringe's cylinder, and a third grasping collar at the syringe's needle assembly that is configured for insertion into the FIG. 11 collar with the needle not yet having punctured through the vial's top seal.
FIG. 62 shows a similar view as that of FIG. 60 with the needle having been inserted through the vial's top seal and into the vial.

FIGS. 61 and 62 show the combination of top vial collar 225 of FIG. 59 and the receipt of an associated syringe assembly. In this embodiment, the syringe assembly is similar to that described above in FIG. 46. In other words, the syringe assembly of FIG. 61 that is being inserted into the open end of collar 225 features syringe assembly 157 comprising syringe 158 as well as plunger end grasping collar 154 and dumbbell sleeve 156 provided along the cylinder of syringe 158 (provided by a slide fit over the cylinder or an overmolding integrated combination and because of this volume measurements can be on the plunger). In addition, there is provided needle hub sleeve 192 like that described in FIG. 50. However, rather than needle hub sleeve 192 being inserted into a crush collar like in FIG. 50, in this case it is being inserted into the open topped collar 225 which provides for stable puncturing of vial 224 and removal of medicament therefrom. This stable puncture relationship between syringe assembly 157, collar 225 and vial 224 is illustrated in FIG. 62 wherein the syringe is in puncture mode with vial 224.

Figure 63:
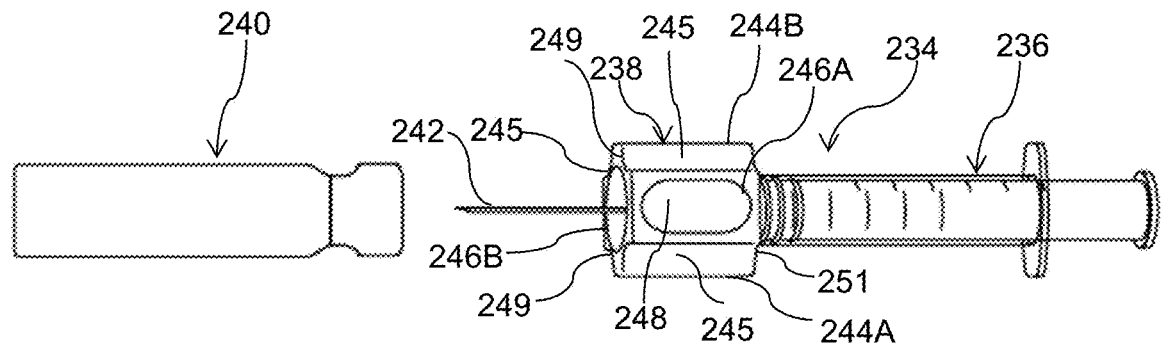
FIG. 63 shows a syringe having attached to it the collar of FIG. 10a just prior to supply vial puncturing with the needle of the syringe.

FIG. 63 shows syringe assembly 234 comprising syringe 236 as well as grasping collar 238 of FIG. 10a configuration. Syringe assembly 234 is shown just prior to supply vial 240 puncturing with the needle 242 of syringe 236. Collar 238 is shown as having elongation in the direction of needle extension and partially covering a portion of that needle. Further, as in the FIG. 10a embodiment, collar 238 is formed from a monolithic block of material that is preferably an elastomeric plastic and flexible as in medical grade silicone rubber. Further, collar 238 has a quadrilateral cross-section periphery that includes two opposing longer ridge walls (246A, 246B) that are circumferentially straight or only slightly curved about their periphery surface, two opposite opposing shorter ridge walls (244A, 244B), and finger depression recess 248. These walls are separated by concave recesses 245 at locations that would otherwise have represented corners of the quadrilateral block. The side walls form gripping projections that are separated by the concave recesses that extend the full elongation length between forward surface 249 and rearward planar surface 251. The general range of height or thickness for collars having the FIG. 10a general configuration includes 2 mm to 60 mm with the embodiment of FIG. 63 being preferably about 20 mm to 50 mm, as in 40 mm long. The length can vary depending on the circumstances as in the length of the needle, the length of needle desired for exposure, the length of the needle hub assembly, the nature of the utensil involved at the collar engagement site at the cavity in the forward end 249 of collar 238.

Figure 64:
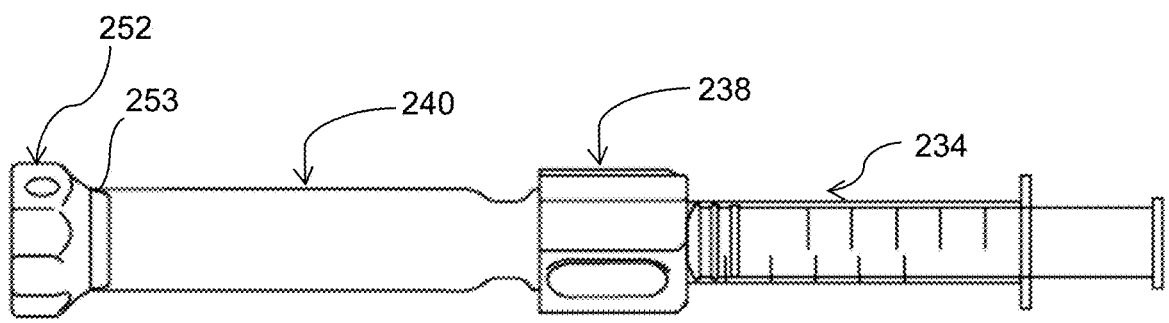
FIG. 64 shows a similar combination as FIG. 63 but with the combination of the FIG. 10a collar and syringe fully attached together, and with the supply (e.g., specimen or medicine source) vial having the collar of FIG. 11 as a means to better grasp the supply or specimen vial's base end; the sequence of collar attachment and utensil-syringe combination can be either collar first attached to syringe or collar first attached to vial before mutual connection.
Figure 65:
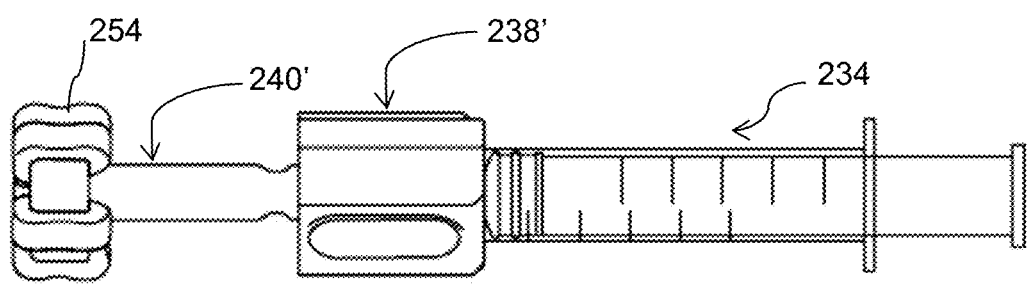
FIG. 65 shows a similar combination as that of FIG. 64, but with the vial having a base mount of FIG. 3a rather than the collar of FIG. 11, and with a diameter size suited for horizontal orientation of the syringe assembly (in similar fashion to FIG. 64).

FIG. 64 shows a similar combination as FIG. 63 but with collar 238 of syringe assembly 234 being fully attached to the sealed end of vial 240 in a puncture relationship, and with the supply (e.g., specimen or medicine source) vial 240 having collar 252 (of FIG. 11 configuration) mounted by flexure (or in an overmolding relationship) on the vial's base 253 as a means to facilitate better grasping of the vial as when separating the vial from the collar 238 following medicament draw from the vial or medicament insertion into the vial. Collar 252 also provides for a more stable base for plunger push down or just for support surface stand up. As noted, collar 252 can be supplied to the vial base by an overmolding plastic injection technique. Further, rather than attaching collar 238 to syringe before vial puncturing, collar 238 can be first mounted on the vial and the syringe then inserted FIG. 65 shows a similar combination as that of FIG. 64, but with a small diameter vial 240' having a base mount 254 of FIG. 3a configuration rather than the collar of FIG. 11 shown in FIG. 64. The smaller vial 240' is received in a corresponding smaller capture recess in the forward end of collar 238' (as compared to the larger capture recess in collar 238). The base mount also provides stable support during plunger down movement and while in stand-up state in general or may be rested horizontally.

Figure 66:
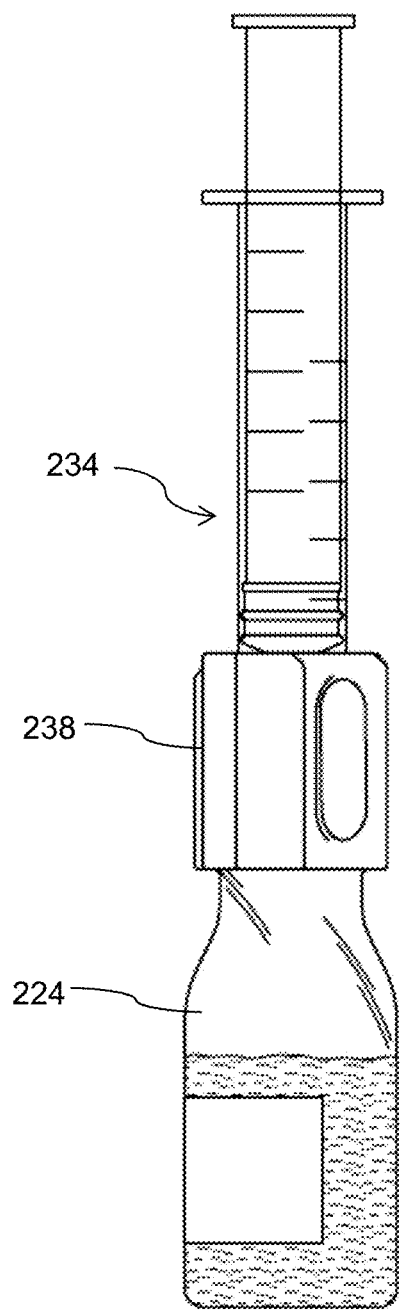
FIG. 66 shows the collar of FIG. 10a (elongated or thicker in height version) attached to the syringe's needle assembly with the needle assembly's needle inserted in a medicine bottle.

FIG. 66 shows the same type collar 238 mounted on syringe assembly 234 in engagement with the upper rim of bottle 256. Again, the flexible nature of collar 238 and suitably dimensioned cavity at that end provides for a sealed engagement during needle puncturing or placement into the bottle. Alternatively, the collar 238 may be placed first over the vial (rather than first on the syringe) and the syringe inserted into the vial, allowing one handed fluid withdrawal procedures.

Figure 67:
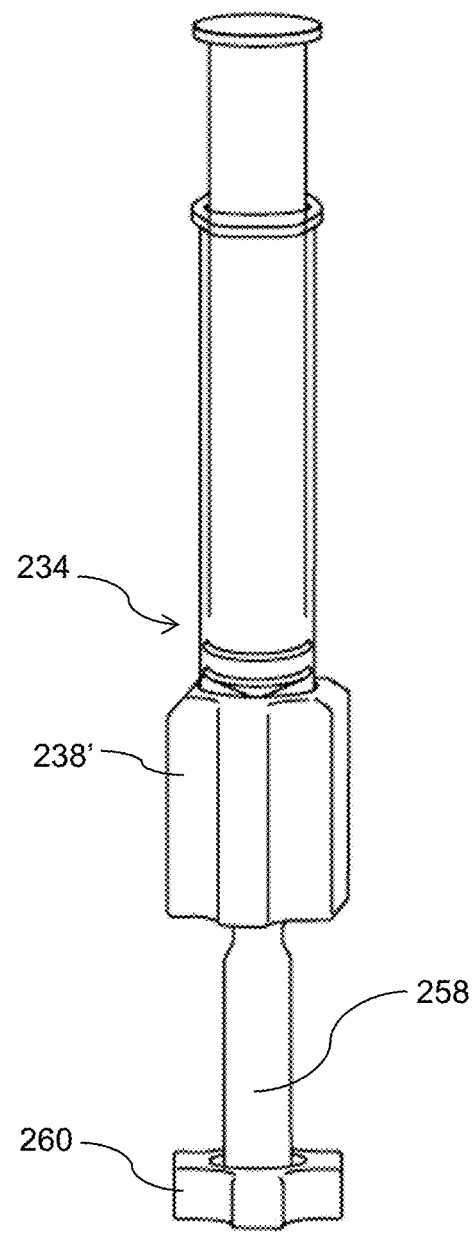
FIG. 67 shows the collar and syringe combination of FIG. 66 in fluid communication with a vial having at its base a FIG. 10a collar (short or thinner in height version).

FIG. 67 shows the same type collar 238' mounted on syringe assembly 234 in sealed off engagement with the upper end of canister 258 having at its base collar 260 of FIG. 10a configuration (short or thinner version depicted). As depicted, the aperture in collar 260 is in friction engagement. The friction level can be increased upon a squeeze compression action on collar 238, such as when removing collar 238' from its engagement with canister 258. Collar 238' would have its vial capture end of a small diameter than collar 238 when the top rim of the bottle has a significantly greater diameter than that of the vial.

Figure 68:
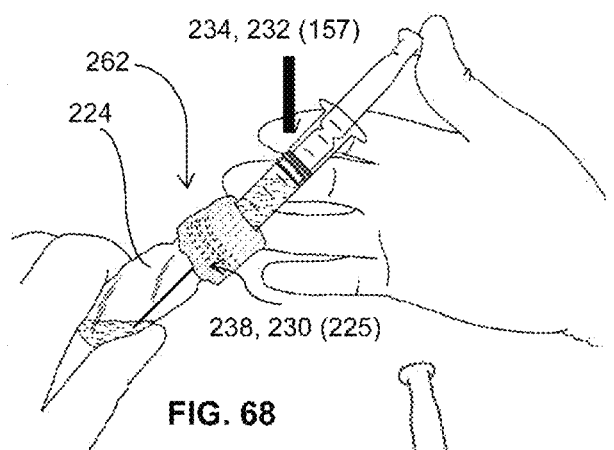
FIG. 68 shows a flexible collar of the present invention with opposite, different sized apertures, with the larger aperture opening out at a first end of the collar and being configured for releasable and flexible attachment (with a flex over such as a snap over relationship, and not a threading requirement relationship) with the threaded top opening of the bottle; and the other collar aperture being smaller and opening out at the opposite end of the collar and being configured for a releasable and flexible engagement with the cylinder portion of a syringe at the needle end; the flexibility of the collar allowing for needle repositioning which is useful in efforts to draw out the last part of liquid in a bottle.

FIG. 68 shows combination 262 comprised of a flexible collar of the present invention supported on a syringe in combination with a bottle with liquid. Thus, FIG. 68 is illustrative of a relationship such as that described having a collar 230, syringe 232, and bottle 224 combination (shown in FIG. 60); or collar 225, bottle 224, and syringe assembly 157 of FIG. 62; or collar 238, bottle 224, and syringe assembly 234 of FIG. 63. As in FIG. 60, the collar design is typically one with opposite, different sized apertures, with the larger aperture opening out at a first end of the collar and being configured for releasable and flexible attachment with the threaded top opening of the bottle (with a flex over relationship and preferably not a threading requirement relationship between the lower end of the collar and the bottle received); and the other collar aperture being smaller and opening out at the opposite end of the collar and being configured for a releasable and flexible engagement with the cylinder portion of a syringe at the needle end (or a sleeved end of the syringe assembly as in sleeve 192 in FIG. 62). As seen in FIG. 68, the flexible nature of the collar of the present invention, provides for a degree of relative adjustment between the needle and the vial such that the needle end can be repositioned in the bottle for drawing up the final amount of liquid.

Figure 69:
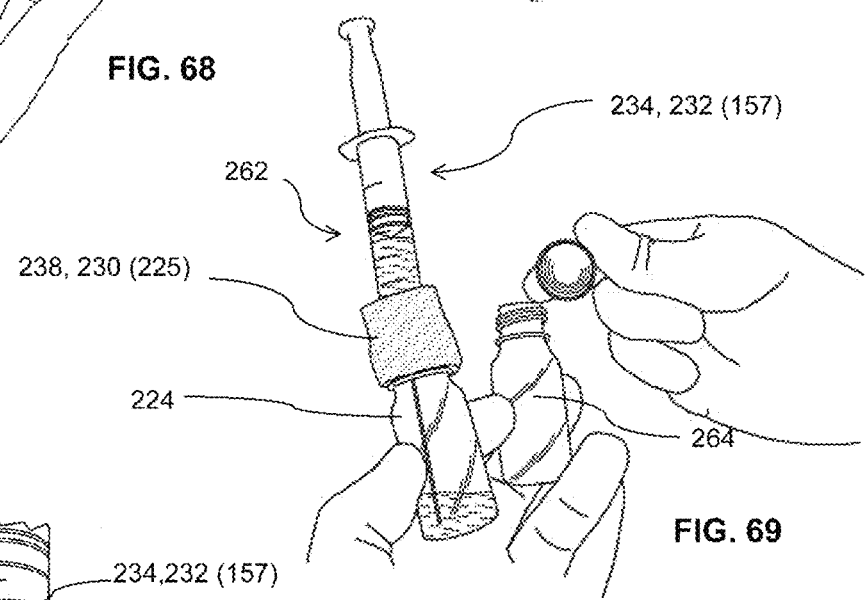
FIG. 69 shows the FIG. 68 combination under the present invention with a view of the ability for a user as, in a surgeon or the like, to multi-task, (thread cap back on a second bottle) due to the ability to hold the entire combination plus the second bottle with one hand.

FIG. 69 shows the FIG. 68 combination 262 under the present invention with a view of the ability for a user, as in a surgeon or the like, to readily multi-task (thread cap back on a second bottle 264) due to the ability to hold the entire combination plus the second bottle with one hand.

Figure 70:
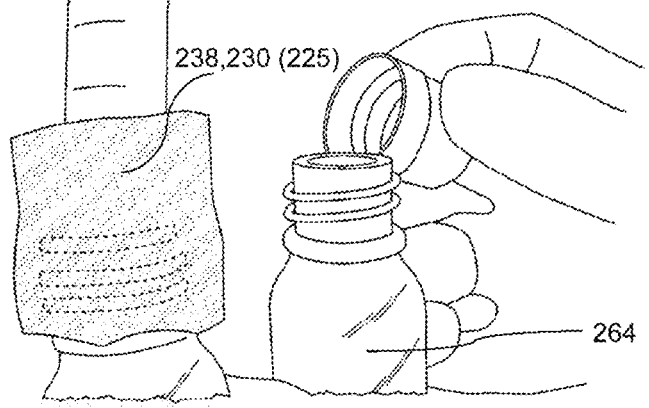
FIG. 70 shows a closer view of the combination and second bottle in one hand, leaving free a second hand for threading a cap on the second bottle.

FIG. 70 shows a closer view of the combination 262 and second bottle 264 in one hand, leaving free a second hand for threading a cap on the second bottle.

Figure 71:
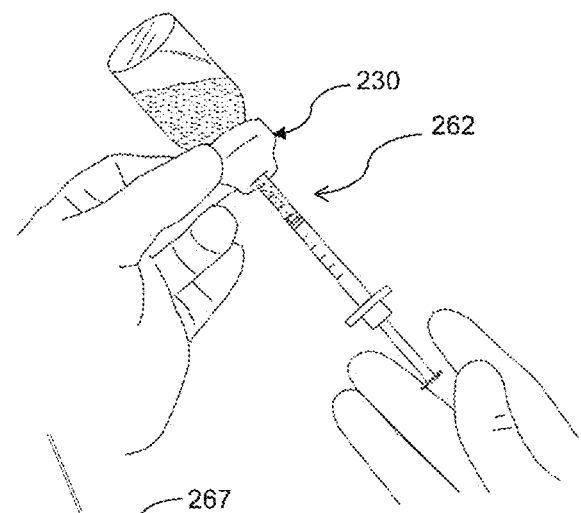
FIG. 71 shows a bottle and FIG. 11 collar combination, but with the collar having a smaller aperture opening out at the smaller diameter collar end that is opposite to the larger diameter collar end in engagement with the threaded opening of the bottle (or a rimmed end); as in the prior embodiment, needle placement relative to the bottle is adjustable and there is also provided the ability to securely grasp and hold the bottle with a two finger off-center pinching operation, which is fixed enough for plunger activation.

FIG. 71 shows combination 262 as represented by the FIG. 60 configuration. As further seen in FIG. 71, the projections of the FIG. 11 type collar 230 (only schematically shown in FIG. 71, but understood to have the periphery as shown in FIG. 11) has a plurality of projections that provides the ability in a user to securely grasp and hold the bottle with a two finger off-center pinching operation, which is fixed enough for plunger activation with the opposite hand.

Figure 72:
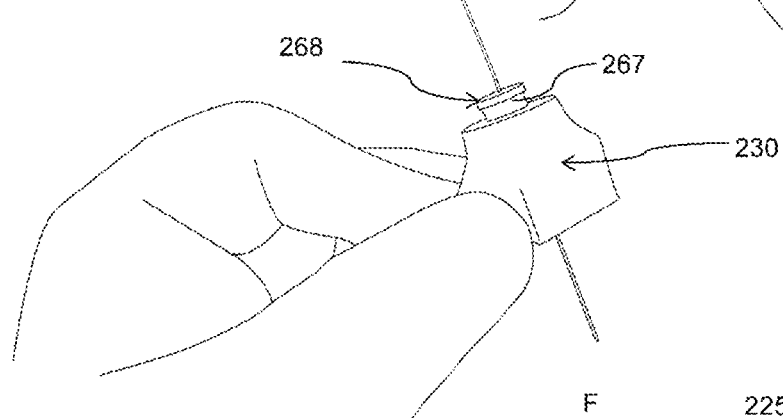
FIG. 72 shows the same off-set two finger pinching relationship with a FIG. 11 collar but with the through hole in the collar supporting a double-ended transfer needle with the user's pinching fingers well away from the needle.

FIG. 72 shows the same off-set two finger pinching relationship with a FIG. 11 collar 230 but with the two stage through hole in the collar supporting hub 267 of the double-ended transfer needle assembly 268, with the user's pinching fingers well away from the needle. Further, with collar 230 in position, the combination may be rested on a surface in the middle collar 230, which will distance the two sided needle from being contaminated due to surface touching.

Figure 73:
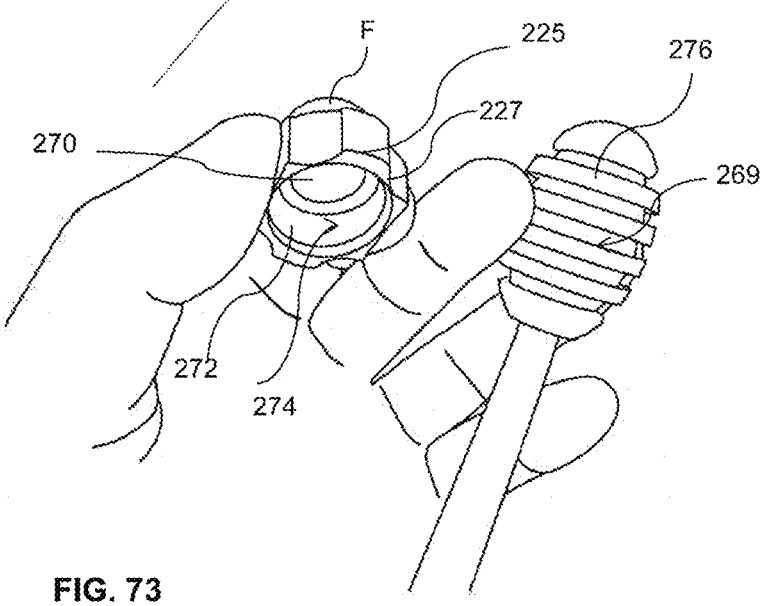
FIG. 73 shows a single hand grasping of a FIG. 11 collar (open top version, with larger base aperture opening out at the bottom of the collar) and a grooved bulb head utensil.

FIG. 73 shows a single hand grasping of a FIG. 11 type collar (open top version, with larger base aperture opening out than the upper open top aperture such as collar 225 of FIG. 59) and a grooved bulb head utensil 269. FIG. 73 also shows the interior of collar 225 as having an upper diameter opening 270 for receipt (and relative flexible support and sealing) of, for example, a syringe assembly. The lower opening 272 in collar 225 is defined by the enlarged (smooth in this embodiment) diameter wall surface 274 designed to engage a bottle top as in FIG. 61, as well as different configured shaped utensils such as the bulbous head 276 of utensil 269, made possible by the flexibility and thinner relative nature of wall 227 defining wall surface 274. FIG. 73 also shows the freedom to hold collar 225 with two fingers, one on the periphery, and the other finger (F) extending to (e.g., into) the top opening of collar 225 (or in some embodiments the top is closed off with a depressed recession).

FIG. 74 shows the components of FIG. 73 in an engaged state and with the same offset, two finger grasping described above. Also, FIG. 74 illustrates that collar of FIG. 11 configuration also preferably, like the FIG. 10a general peripheral configuration, has opposing long ridge sides PRL (one shown) and opposing short ridge sides PRS (one shown) separated by concavities CV as to provide for enhanced grasping as by two finger pinching.

FIG. 75 shows the combined components of FIG. 74 and the ability for a pinch support to hold the combination in a suspended state with one hand.

FIG. 76 shows modified tray embodiment 276 which is shown in cut-away but the remaining portion is in one embodiment represented by tray 140 in FIG. 46. In this embodiment, however, tray 276 has an end aperture 278 that has a configuration not designed specifically for a base mount such as shown in FIG. 30A, but has a generally quadrilateral outer periphery with inwardly extending convex walls, That is, as shown in FIG. 76, reception aperture 278 has a pair of opposing long sides 280A, 280B, a pair of opposing shorter sides 282A and 282B, and four corner projections 277 with curved exposed surfaces. Aperture 278 is designed to snugly receive a collar such as shown in FIG. 11, wherein there are long and short ridge sides opposing each other and recesses at the corners between the formed projections along the sides. Thus, tray 276 has aperture 278 that is well suited for support of components of the invention such as grasping body 168 formed integrally with plunger 170 of the illustrated syringe 172 in FIG. 48.

FIG. 77 shows the snug interrelationship or integrated collar and plunger support relationship shown in FIG. 48. As seen in FIG. 77 the collar 168 end of plunger 170 is inserted into the conforming aperture 278c in a snug reception state relative to supporting/transfer tray 167.

Figure 77A:
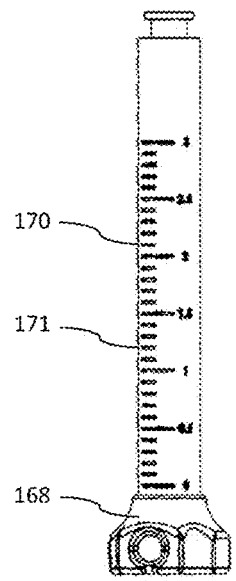
FIG. 77A shows a full view of the combination of a syringe plunger having a FIG. 11 collar at its base.
Figure 77B:
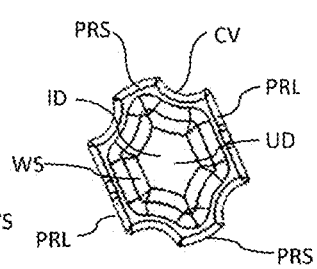
FIG. 77B shows a view of the collar of FIG. 77A in bottom perspective.
Figure 77C:
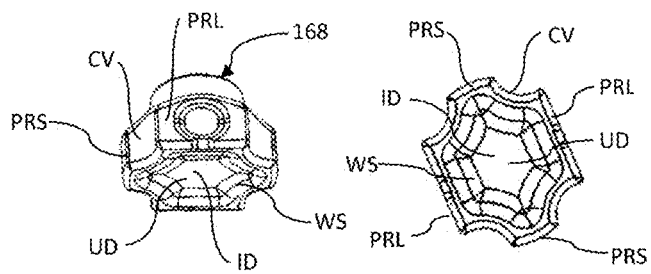
FIG. 77C shows a view of the collar of FIG. 77A in a bottom plan view.

FIG. 77A shows plunger 170 (with rubber seal piston for mounting on the top plunger end not shown), having a main body 171 (with graduations for liquid content) and the attached collar 168 of FIG. 11 general configuration (e.g., a flex attachment, overmolding or bonded relationship for securement). Also, as shown in FIGS. 77B and 77C, collar 168 has opposing ridges with long (circumferential) sides PRL, opposing ridges with shorter (circumferential) sides PRS, and concavities CV separating the adjacent short and long ridges (PRL-PRS). FIGS. 77B and 77C also illustrate the underlying depression UD formed at the base undersurface of collar 168 which features upwardly and inwardly extending wall sections WS that form the boundary for the interior depression area ID, which is centralized on the undersurface. In this way, the rim edging defined by wall surfaces WS and the outer periphery of the collar provide for a degree of flexure along the collar edging. Also, the interior depression depth is preferably less than the depth of the concavities CV on the periphery of the collar.

Figure 77D:
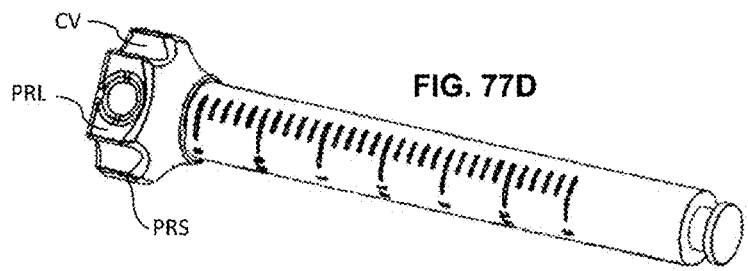
FIG. 77D shows the combination of FIG. 77A from a different orientation.
Figure 77E:
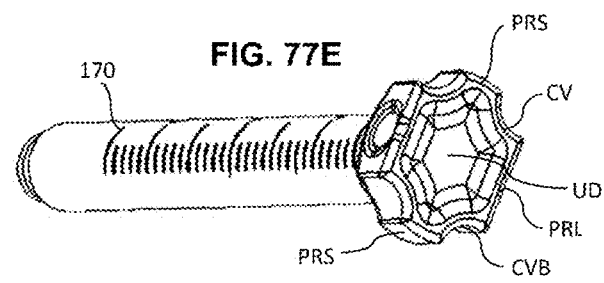
FIG. 77E also shows the combination of FIG. 77A from a different orientation

FIGS. 77D and 77E illustrate plunger 170 in a lying down state (rather than an upward or vertical support state shown in FIG. 77A). As seen, the interior edging of the adjacent projections PRS and PRL can contact with the support surface, and since they are separated by bottom positioned concavity CVB, collar 168 acts to preclude rotation of plunger 170 once set on its side, which is helpful in a working environment where undesirable utensil roll offs can occur.

Figure 78:
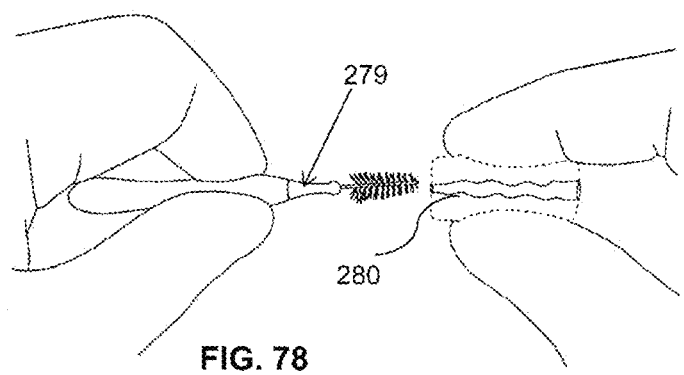
FIG. 78 shows an alternate embodiment of the present invention with a haptic promoting cavity provided in a grasping device that is suited for an instrument support and transfer, which in this case is a bristle cleaning instrument, with the haptic feel including the sensitivity of being able to feel when each bristle ring set moves forward or back once asserted.

FIG. 78 shows an alternate embodiment of the present invention with a haptic promoting cavity provided in a grasping collar device 280 that is suited for instrument support and transfer, which in this case is a bristle cleaning instrument 279. As shown in FIG. 78, grasping collar 280 has a solid main body of elastomeric material (preferably relatively soft as in 20 to 50 shore, more preferably 20 to 40 shore) with a central through-hole that is a wavering cavity with varying diameter dimensions along the length. The nature of grasping collar 280 is such that there is retained a "feel" component of the inserted instrument through the elastomeric sleeve thickness. For example, a user can feel the stepped progress of the bristles within the non-smooth cavity and also still be able to evaluate the relative level of compression on the received instrument.

Figure 79:
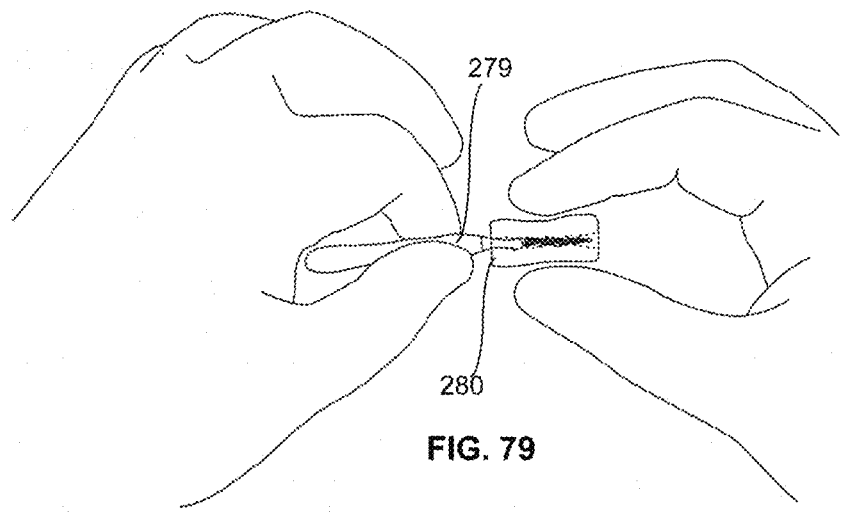
FIG. 79 shows the cleaning instrument with bristle brush having been inserted into the sterile cavity of the grasping device which provides, for example, transfer from a one person to another without finger contamination and also without inadvertent bristle crushing due to over pinching of bristles directly.

FIG. 79 shows the cleaning instrument with bristle brush 279 having been inserted into the sterile cavity of the grasping collar 280, which provides, for example, transfer from one person to another without finger contamination, and also without inadvertent bristle crushing due to over pinching of bristles directly (based on the retained "feel" provided by the cavity and collar haptic combination).

With reference to FIGS. 80 to 84, there is described a treatment procedure using grasping collar 282 of the FIG.

Figure 80:
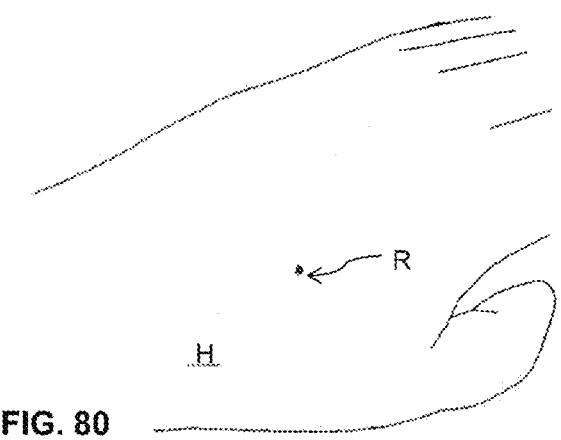
FIG. 80 shows a hand with a region intended for treatment.
Figure 81:
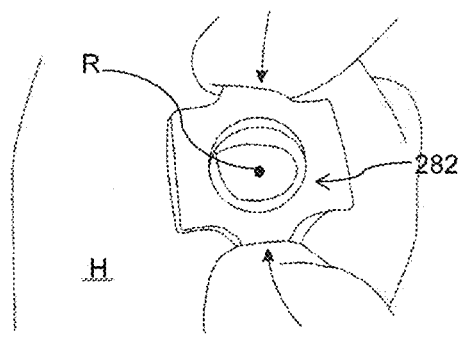
FIG. 81 shows the versatility of the collar, which is shown as a base mount in FIG. 67, but as a skin collector and positioner of the region intended for treatment in the present Figure, with this Figure showing initial placement of the collar around the region intended for treatment.

10a configuration, and of a thinner mode (e.g., 1.5 mm to 6 mm, and more preferably 2 mm to 4 mm). FIG. 80 shows hand H with region R intended for treatment, while FIG. 81 shows the versatility of collar 282, which is shown as a base mount in FIG. 67, but as a skin collector and positioner of the region intended for treatment in the present FIG. 81, with FIG. 81 showing initial placement of the collar around the region R intended for treatment. Also, FIG. 81 shows the beneficial short ridge to short ridge compression orientation.

Figure 82:
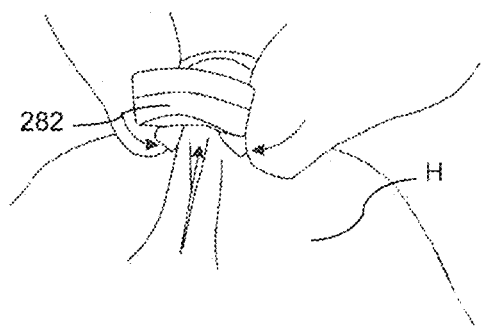
FIG. 82 shows the collar of FIG. 81 in a compression state (pressing together of two opposing shorter ridge side surfaces) that causes a simultaneous capture and lifting of skin such the region intended for treatment is presented within an intermediate, upper region, (or above) the aperture of the collar with the skin assuming a mushroom configuration due to the lower edging of the collars recess bending upward.

FIG. 82 shows collar 282 in the peripheral compression state that causes a simultaneous capture and lifting of skin such the region R intended for treatment is presented within an intermediate, upper region, or above the aperture of the collar 282 and the underlying skin is compressed by the collar there below. Further, as seen from FIG. 82 the lift up is achieved by having the collar flex in a bowed up state that results in the lower interior cavity edging achieving an automatic skin pile lift up while compression is ongoing which helps isolate the region R without pain in the patient, and with the lower edging of the collars cavity being closest together to form a mushroom configuration in the skin pile.

Figure 83:
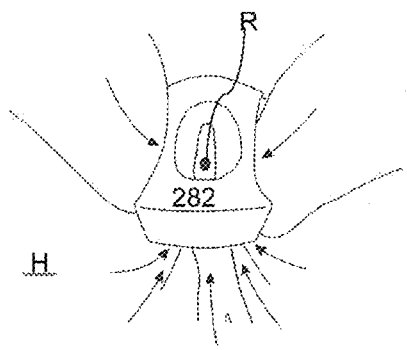
FIG. 83 shows another view of the relationship shown in FIG. 82.

FIG. 83 shows a more top oriented view of the pinched pile of skin.

Figure 84:
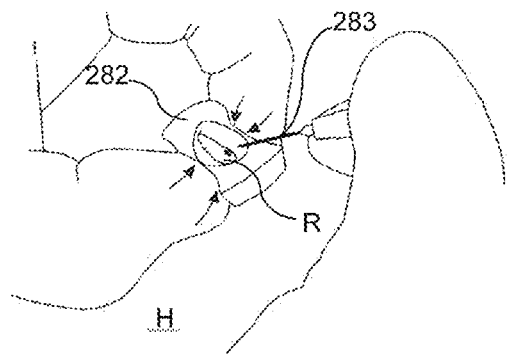
FIG. 84 shows the insertion of a needle in the exposed, desired area in the region intended for treatment.

FIG. 84 shows the insertion of a needle 283 in the exposed, desired area in the region R intended for treatment.

Figure 85:
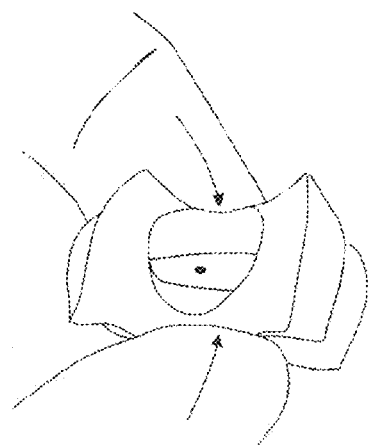
FIG. 85 shows the collar of FIG. 81 in a similar compression, lift state relative to a different object, and how the lower edging of the collar moves inward and upward simultaneously.

FIG. 85 shows collar 282 of FIG. 81 in a similar compression, lift state, but relative to an object O other than skin.

Figure 86:
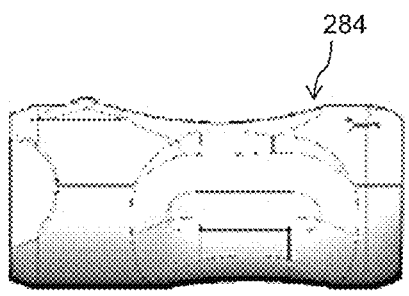
FIG. 86 shows a collar or sleeve similar to that attached to the needle hub of the syringe in FIG. 61, but with a modified haptic promotion cavity which is well suited for catheter equipment manipulation.

FIG. 86 shows an alternate embodiment collar 284 similar to that of FIG. 68 but with a modified haptic promotion cavity which is well suited for catheter equipment CE manipulation. FIGS. 87 and 88 show cross-sectional views of collar 284 as well as the central cavity 286. Central cavity 286 includes concavities and convex depressions that form a meandering pattern, with FIG. 90 showing some illustrative (non-limiting) values for the concavities and convex valleys that are off-set in longitudinal length. This meandering cavity with different projection and cavity regions along the length of the cavity facilitate the feel of an inserted instruments movement (e.g., stepped advancement in collar), while also providing for the option of different compression level locations in the collar. In this embodiment, the central cavity 286 includes an enlarged end 286E having a horn shape shown with an increasing diameter to the opening (right side in FIG. 90). The enlarged end facilitation initial insertion of a catheter sleeve or other thin instrument.

FIG. 88 shows a perspective view of the collar shown in FIG. 87. Collar 284 functions to avoid having a surgeon grasp a thin catheter line for an extended period of time which can lead to hand, muscle lock up, while it, due to its haptic nature, also avoids unintended crushing of an outer catheter sleeve which can be <3 mm (as in 2.5 mm) in diameter for some catheters and thus can be fragile in nature.

FIG. 89 shows the grasping collar 284 in three different positions (time sequenced as only one collar featured in the embodiment) on catheter line 288 of catheter equipment CE and with the middle (time position relative to either a catheter sleeve feed relative to a stationary collar, a clamped movement of both, or a collar movement relative to a fixed in position catheter sleeve). FIG. 89 shows collar 284 in cut away in similar fashion as in FIG. 90 to illustrate the haptic generally sinusoidal wave pattern of the through-hole cavity 286 featured for the sleeve which has different clearance widths along the length as well as different outlet opening diameters in this embodiment. In this way, the user can feel the relationship between the catheter object and collar 284 for proper manipulation, with a higher compression squeeze providing for a more secure locking of collar 284 and received catheter line 288 (or some other object that is threadable through cavity 286). A lower compression state provides for a haptic feel that provides for a gradual slide relationship that is more resistant than a non-compression slight resistance between the central cavity meandering walls and catheter line object 288. A slight resistance without compression relationship is also useful for better control over a feed adjustment FIG. 90 shows the intermediate positioned grasping collar presented in FIG. 89 in an expanded view such that the haptic promoting cavity configuration can be better seen together with some illustrative cavity thickness values of the length of the collar for the catheter equipment embodiment featured. FIG. 90 illustrates a relatively larger grasping collar having a longitudinal length of 27 mm, a first end opening 286D of 2.5 mm, and an outer opening at end 286E of 3.5 mm, thus making it well suited for precision procedures involving catheter embodiments as in catheter 289 shown (e.g., a colonoscopy catheter). The haptic central cavity design makes the collar well suited for finger controlled (external; pressing of sleeve 286) fine adjustments in the catheter CE relative to the collar 284 or vice versa, while the exterior contouring on collar 284 further enhances the control and ease of finger manipulation. In some embodiments, the collar 284 can be provided with a simple circular cylinder exterior configuration with reliance on the haptic central cavity for improved catheter manipulation. However, having both the exterior surface and interior cavity 286 designed with surface contouring provides a synergistic combination of haptic and controlled manipulation with low strain on the fingers. This feel also helps avoid over compression which can lead to undesirable sleeve crimping.

FIGS. 91 to 94 show a similar haptic collar arrangement for a catheter such as that for Fig. set 86 to 90, but with collar 290 being, at one end 286X, a finer grade grasping collar well suited for a finer grade catheter 292. The larger end provides for easy catheter insertion (e.g., 2 to 2.5 mm catheter sleeve) while the smaller diameter section providing friction resistance (while still allowing free sliding) to improve the relative feeding of the catheter sleeve. As seen in FIGS. 91 to 94, collar 290 has a non-meandering through-hole or central cavity 294; featuring, along its 22 m longitudinal length, a small diameter first end 284X (e.g., 1 mm is shown as an example) with a slight gradient of diameter expansion such that the intermediate area 284Y of cavity 294 has, for example, a 1.5 mm diameter that more quickly expands to 2.0 mm in the intermediate area, which in turn is followed by an even greater and non-graduate expansion that opens out at the other end and in this embodiment has a 4.0 mm diameter. Thus, this sleeve has a first end that can retain a finer diameter catheter in sliding friction contact, but an intermediate area with a gradual need for compression to place the cavity surface in contact with the catheter and a still greater clearance end for facilitating initial threading.

FIGS. 95 to 100 show a similar haptic collar arrangement for a catheter as that for Fig. set 86 to 90, but with collar 296 being of a shorter length of 17 mm and having a venturi shaped central cavity 297 featuring a straight initial section 297X of 1.0 mm a narrower diameter venturi throat section 297Y in an intermediate section (shown with a 0.6 mm constriction diameter in FIG. 97), at the other end, a flaring out section 297Z that goes, in expansion sequence, from, 0.8 mm at the throat section interface, to 1.5 mm which leads to the conical outlet having a 2.5 mm (insertion) opening as shown.

Thus, it is the intermediate area or throat region of the central cavity in this embodiment that is in initial contact with the catheter sleeve and it's the outer ends that can be compressed to increase the degree of contact or released to provide for more ease in relative adjustments between the sleeve and received catheter as shown in FIGS. 98, 99 and 100. Again, having the illustrated outer contouring on the exterior surface of grasping collar 296 is preferable in combination with the central cavity haptic catheter contact capability, but the central cavity haptic catheter contact capability is beneficial in and of itself and thus can be advantageously used with non-contoured (collars with circular cylinder without diameter adjustment along its length) outer collar surface.

Figure 101A:
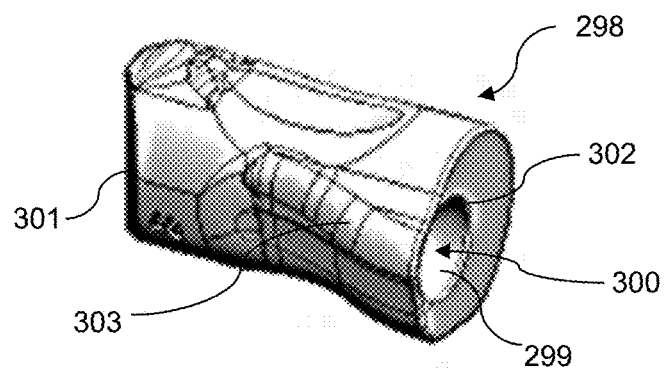
FIGS. 101a to 101d show a different grasping collar or sleeve embodiment featuring a through-hole well suited for needle assembly reception, with FIG. 101a showing a perspective view, FIG. 101b showing a central cut-away view.
Figure 101B:
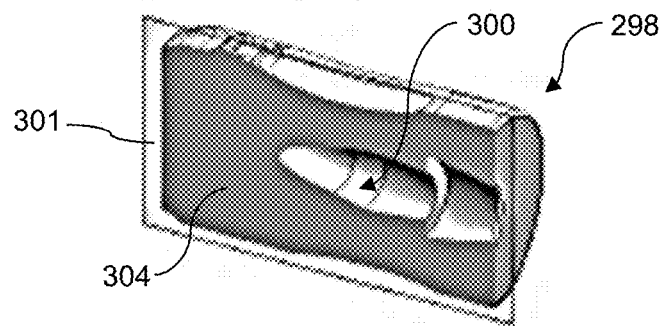
Figure 101C:
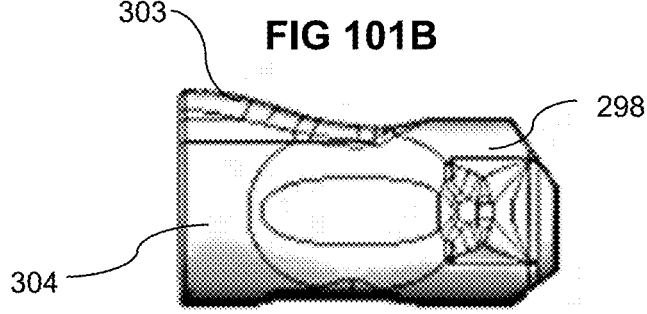

FIGS. 101*a* to 101*d* illustrates an alternate needle assembly collar 298 which, like the above described collar 40 (with through-hole 42), collar 298 is mountable on the hub of the needle assembly or some other instrument (preferably by way of an elastomeric compression fit) such that the desired amount of needle extends out away from a free end of the collar. Also, enlarged exterior segment 303 preferably is placed at the top when collar 298 is pressed against a skin surface (with a single finger for instance) such that the needle shaft extending out of end 301 will be at a desired (fixed and preset angle) despite different finger sizes. FIG. 101*c* thus shows an example of the orientation that collar 298 would have when placed in skin contact under one embodiment of use.

Collar 298 has an arrangement that is well suited as a needle assembly collar as it provides, among other features, an ergonomic, gripping sleeve device for needle placement, insertion and dispensing of liquid through the needle as by syringe operation. This collar represents an adaptation of the gripping sleeve device for precision instruments described in U.S. Pat. No. 8,745,825 issued on Jun. 10, 2014, and which patent is hereby incorporated by reference in its entirety for background purposes.

FIG. 101*a* shows a perspective top view of collar 298 (not a top orientation in use, but an orientation that shows the saddle recess, and there can be seen that the angled interior cavity 300 is non-centralized at the time it opens out at end 302 of collar 298 (the needle insertion end). The opening shown at end 302 of collar 298 represents the needle assembly initial insertion end, as the needle tip extends out from the opposite end 301 of collar 298. Thus, collar 298 comprises a solid main body 304 or elastomeric material that is open at opposite ends thereof and attachable as a sleeve close to a needle hub region of a syringe, said sleeve device being designed to facilitate the positioning of the user's hand grip, said sleeve device comprising a longitudinally extended solid body of elastomeric material with beneficial exterior contouring used in conjunction with the syringe internal cavity configuration.

FIG. 101*c* shows a top plan view of collar 298 with the needle assembly initial insertion opening 299 to the left and the needle extension end 301 of collar 298 to the right. FIG. 101*c* also shows a preferred in use orientation wherein 303 slopes down on the top exterior surface which is also the direction of needle assembly slope in the sleeve at least in one embodiment of use.

Figure 101D:
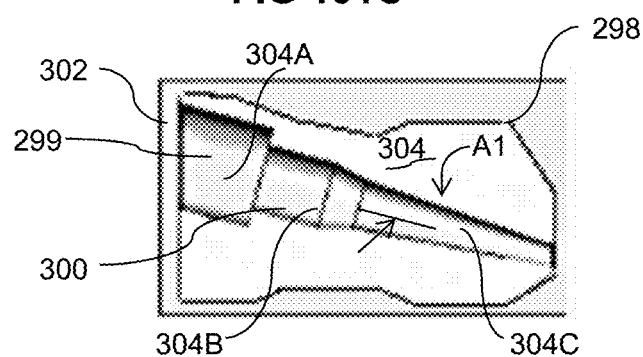
Figure 102A:
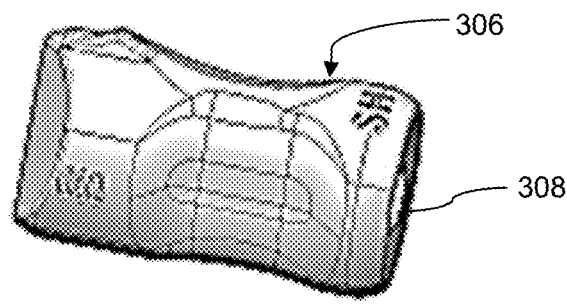
FIGS. 102a to 102d show yet a different grasping collar or sleeve embodiment featuring a through-hole well suited for needle assembly reception, with FIG. 102a showing a perspective view, FIG. 102b showing a central cut-away view.
Figure 102B:
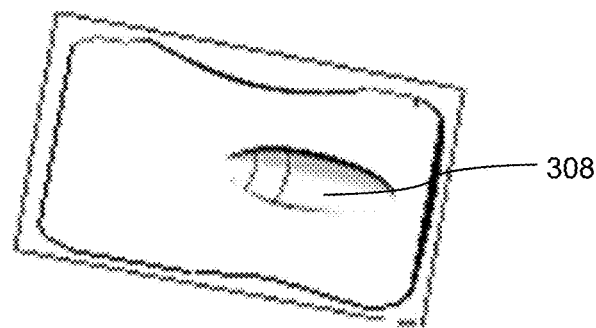
Figure 102C:
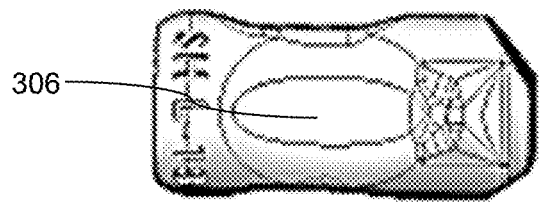
Figure 102D:
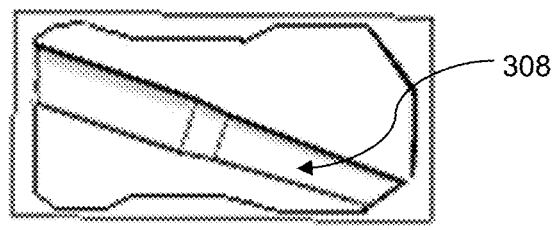
Figure 103A:
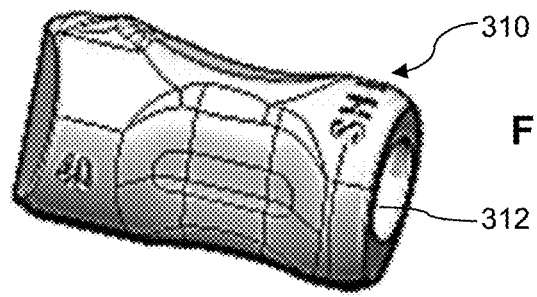
FIGS. 103a to 103d show another different grasping collar or sleeve embodiment featuring a through-hole well suited for needle assembly reception, with FIG. 103a showing a perspective view, FIG. 103b showing a view of the central cavity relative to the FIG. 103a orientation, FIG. 103c showing a top plan view of the collar, and FIG. 103d showing the cavity configuration extending through the collar relative to the orientation of FIG. 103c.
Figure 103B:
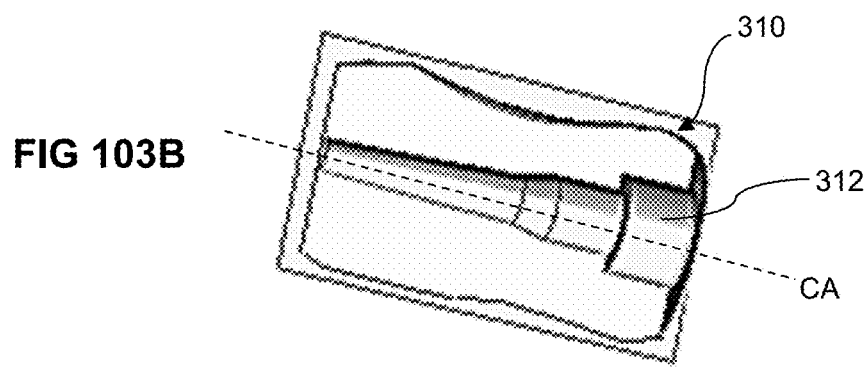
Figure 103C:
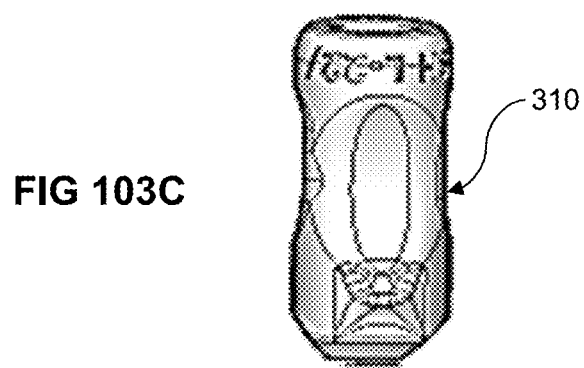
Figure 103D:
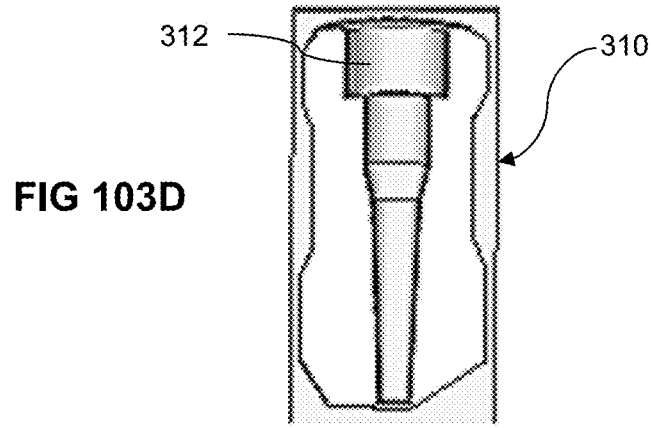

FIG. 101*d* shows the arrangement of the interior cavity 300 with its multi-diameter through-hole formed at an angle in the interior of the solid main body. Through-hole 300 comprises a first, largest diameter section 304A, a second, intermediate diameter section 304B, and a third, minimum diameter section 304C. The first through-hole section 304A opens out at proximal end 299 of the collar, whereas the third, minimum diameter section 304C opens out at distal end 301 of collar (e.g., the end of the collar closest to the needle tip when present). Also, section 304*c* is shown as comprising a short frusto-conical section followed by a longer frusto-conical needle covering section.

As particularly shown in FIGS. 101*a* to 101*d*, collar 298 is a monolithic solid body but for the through-hole 300 which extends at an incline relative to the central axis CA of extension of collar 298 shown in FIG. 101*d*. Illustrative embodiments of the invention feature inclines like that described above, inclusive of an inclination that places the needle axis at a 15° relationship with the skin surface in a planar state. Additional incline angles μl include a range of 15° to 60° and more preferably 40° to 60° inclusive of and each angle point in the noted range and sub-range and at the end points of each range.

With reference back to FIGS. 24*a*, 27*a* and 27*b* and current Figure set 101*a* to 101*d*, there can be seen that aperture 304A has a diameter that conforms to the other diameter portion of needle assembly 66 (FIG. 24*a*) such that, upon insertion, there is a stretch and retraction action on the surface of aperture 304*a* for a snug (compressed, friction contact) retention on the cylindrical base 67 of the needle assembly 66. Furthermore, the intermediate diameter region is designed to frictional/snugly retain the star pattern ridges extending up from the cylindrical base 67 (e.g., the circumferentially spaced ridges extending up from base 67 of needle assembly 66). Third section 78*c*, which is the minimum diameter section is preferably designed to closely conform to the hub of the needle and the needle shaft itself. In so doing, the conical hub is snugly received in the most internal portion of aperture 304*c*, while the needle shaft is also closely retained. Various other collar cavity designs are featured under the present invention with the goal to provide a good working fit with the needle assembly components as in the hub and needle shaft.

With the arrangement of FIGS. 101*a* to 101*d*, featuring collar 298 of an illustrative length of 22 mm (a more suited design for other than fine needles such as the smaller shaft "IV" needles), the user can readily arrange the needle shaft at a desired angle of entry as in a 40° to 60° angle. The user can be, for example, medical personnel or the recipient himself when self-inserting, with the collar 298 and its improved grasping function providing for those with poor finger compression capability or handling dexterity (e.g. arthritis in hands) being better able to manipulate the needle. A scaling up or down in sizes can be implemented if the needle assembly dictates.

FIGS. 102*a* to 102*d* illustrates an alternate needle assembly collar 306 which, like the above described collar 298 (with through-hole 42), collar 306 is mountable on the hub of a needle assembly. Collar 306 is particularly suited for use with finer needles such as IV needles and has a different configured cavity 308 that is narrower than the above described through-hole 300, as to better conform to the finer grade needle assembly being inserted therein (there is less distinct shoulder regions from one diameter to the next and more of a conical adjustment in collar 306 as compared to 298). The entry angle for through-hole 308 in collar 306 is, however, similar as that of collar 298 (an entry angle of 60° to 40°). The overall length of collar 306 (e.g., a length of 18 mm) is shorter than its collar 298 counterpart for this embodiment.

FIGS. 103*a* to 103*d* illustrates an alternate needle assembly collar 310 that features a non-offset or coincident central axis CA through-hole 312 extending through the main body of collar 310. As with the above described collar embodiments, the collar is formed of a soft to touch elastomeric material such as the aforementioned material such as silicone rubber, TPE, and TPR. FIGS. 104a to 104d illustrates an alternate needle assembly collar 314 that features a non-offset but altering in diameter central cavity 316. Central cavity 316 shares a common central axis of elongation with collar 314 with the central axis of through-hole 316 extending through the main body of collar 314. Collar 314 is, in this embodiment, a relatively short collar with an illustrative length of 17 mm. Also central cavity 316 has from left to right in FIG. 104b, initial circular cylinder cavity section 318 of the least diameter (suitable as a needle shaft receiving region and visibility covering section of the collar), a first diverging frusto-conical cavity portion 320, a first converging frusto-conical cavity portion 322 with common maximum radius at the interface with cavity portion 320, and a second diverging frusto-conical cavity portion 324 with common minimum radius interfacing with the minimum radius end of cavity portion 322. Second diverging frusto-conical cavity portion 324 also opens out as the end of collar 314 opposite the end from which cavity section 318. Thus, cavity portion 324 provides a sloped inlet for centering the needle hub upon initial insertion and the symmetric frusto-conical combination of cavity portions 320 and 322 provide a nesting region for the hub base of the needle. The central coincident axis of elongation provides for 90° insertions, although through grasping manipulation of the collar the other insertion angles can also be achieved.

FIGS. 105a to 105d illustrates a short (e.g., 11 mm) versatile grasping collar 328 that is suited for syringe cylinder attachment in that it has a smooth central bore dimensioned to slide over and frictionally retain a position on the syringe cylinder as to provide a means for syringe manipulation via the collar's retention on the syringe.

Figure 106A:
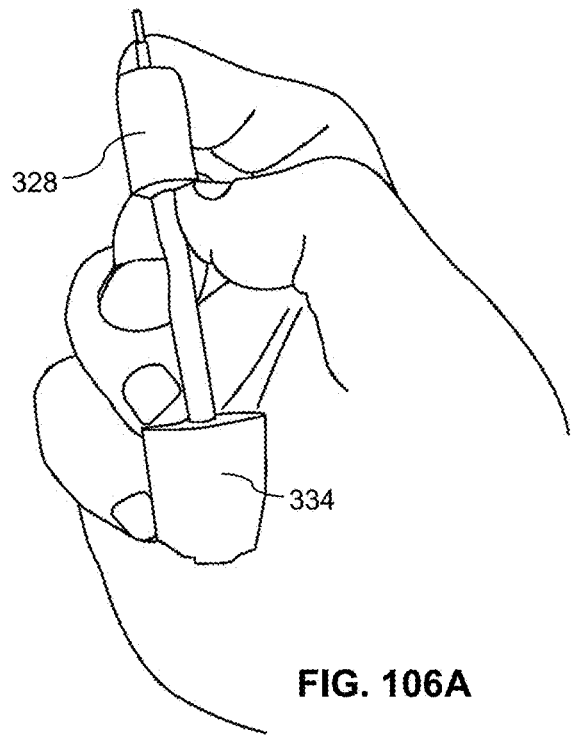
FIGS. 106a to 106b and FIGS. 107a to 107e show various view of a combination set of collars featuring a first collar for securement to a distal end of an object such as the illustrated push, pull and/or torque (e.g., dental) tool and a second collar of FIG. 10a configuration for attachment to the base of the tool, with FIG. 106a showing the combination being held with one hand contact on each of the collars and the tool.
Figure 106B:
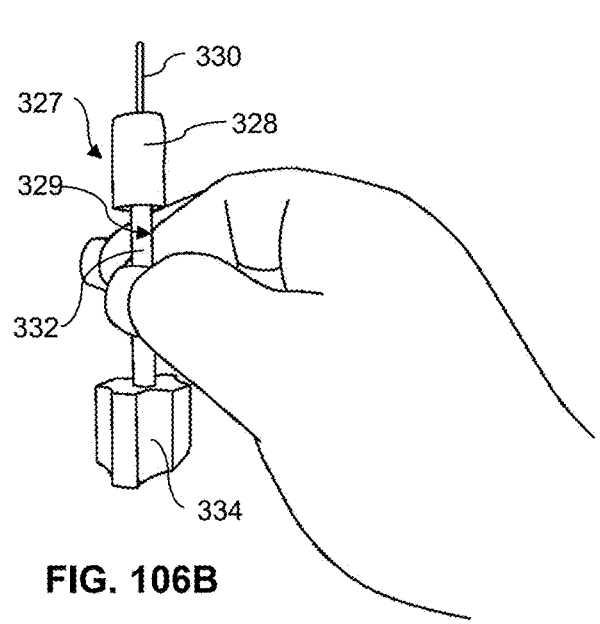
Figure 107B:
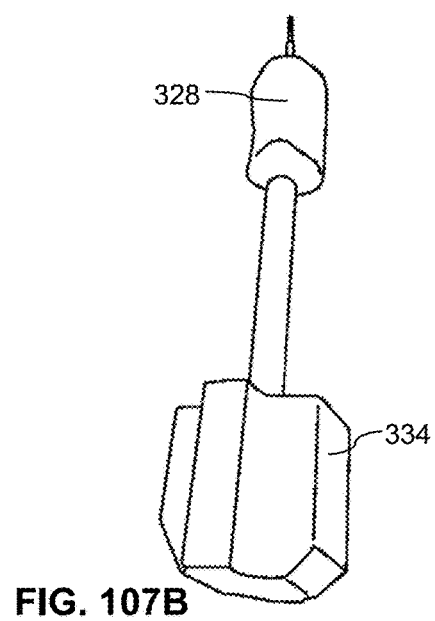
Figure 107C:
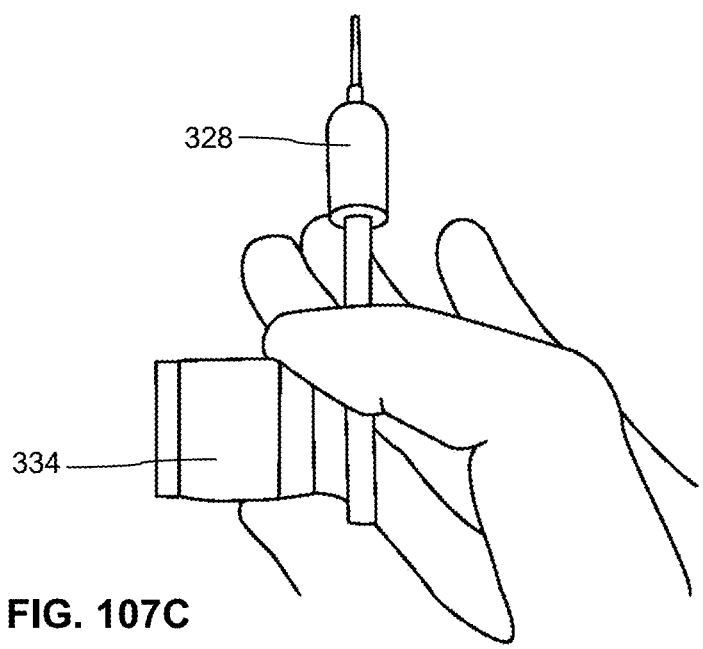
Figure 107D:
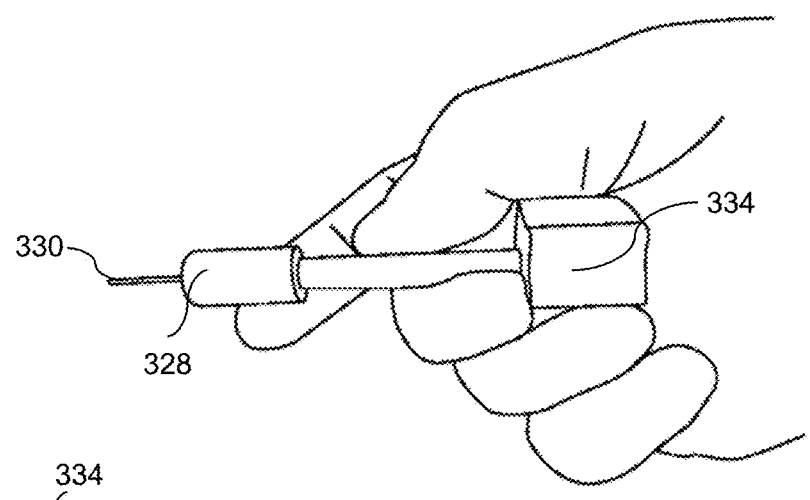

Collar 328 is also suited for other object grasping such as a "pushed puncture" tool (e.g., dental and other medical and non-medical uses) instrument, and as part of a kit associated with such tool or instrument manipulation. As seen in FIGS. 106a, 106b and 107a to 107e, collar 328 forms part of a two component kit suited for single hand securement of such an instrument 329 and desired no-rotation or rotation states, through single handed manipulation. Instrument 329 in this embodiment has a narrow shafted end 330 (two stage 330A, 330B) extending from a (e.g., knurled) handle 332. The second part of the kit is shown as base collar 334 of the FIG. 18 configuration that includes one or more slanted long sided projections as best shown in FIGS. 106b and 107b. The kit combination 327, comprised of base collar 334 and distal end collar 328, provides for a secure but readily adjustable grasping arrangement on the object (tool or instrument) shown. That is, the combination provides for smooth rotation of the instrument within the one common holding hand by twisting fingers pinching collar 328 while discontinuing compression at the palm and collar 334 interface. Also since the slanted projection of collar 334 sets against the thicker part of the palm (extending out and to the thumb of a hand) upon compression of the instrument thereagainst such that sleeve portion can be locked into place on the noted palm region with minimum effort, until a rotation of the instrument or forward projection is desired. Also, the FIG. 107d grasping configuration with the projections separated by elongated concavities enables the holder to push the fingers holding collar 328 forward (or retract the fingers back in the opposite direction), while base collar 334 is sufficiently released from compression and allowed to slide along the palm in controlled manner due to the "sliding runners" associated with the projection edges of the collar periphery (FIG. 18 configuration) resting in the palm of the hand. The central cavity of each of the collars can be a straight smooth circular cylindrical cavity that holds on to the body of the instrument (or any desired object for the present combination kit) with sufficient friction retention or can be a different diameter stepped portion matching 330A and 330B diameters in collar 328. The materials for this kit can be similar to those described above for other collars.

Figure 104A:
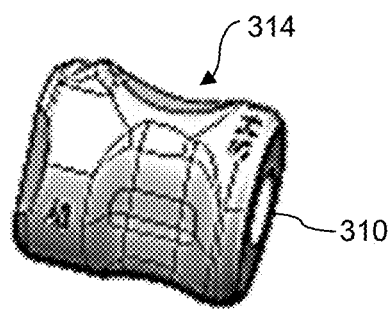
FIGS. 104a to 104d show another different grasping collar or sleeve embodiment featuring a through-hole well suited for needle assembly reception, with FIG. 104a showing a perspective view, FIG. 104b showing a view of the central cavity relative to the FIG. 104a orientation, FIG. 104c showing a top plan view of the collar, and FIG. 104d showing the cavity configuration extending through the collar relative to the orientation of FIG. 104c.
Figure 104B:
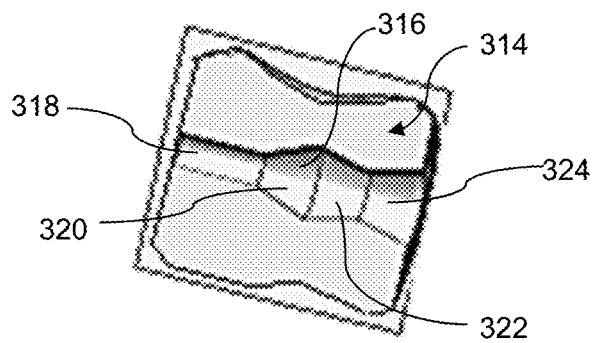
Figure 104C:
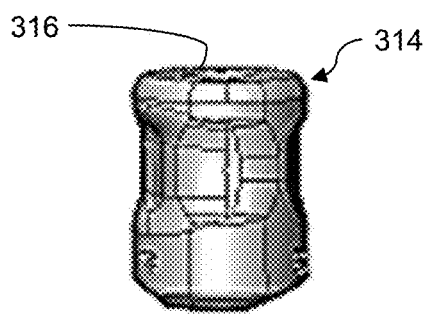
Figure 104D:
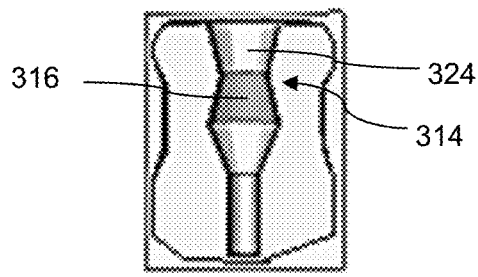
Figure 105A:
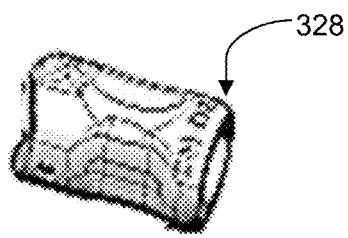
FIGS. 105a to 105d show another different grasping collar or sleeve embodiment featuring a through-hole well suited for syringe body attachment, with FIG. 105a showing a perspective view, FIG. 105b showing a view of the central cavity relative to the FIG. 105a orientation, FIG. 105c showing a top plan view of the collar, and FIG. 105d showing the cavity configuration extending through the collar relative to the orientation of FIG. 105c.
Figure 105B:
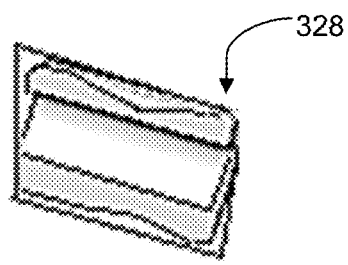
Figure 105C:
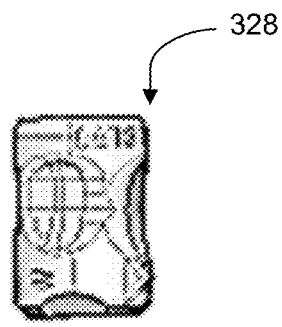
Figure 105D:
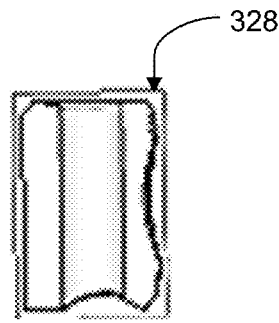
Figure 107A:
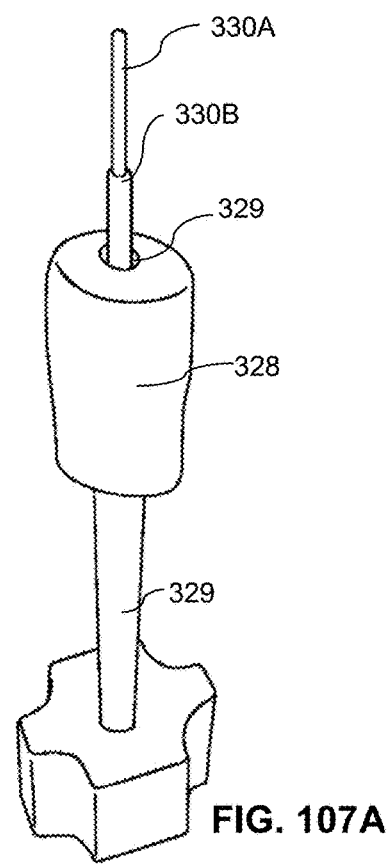
Figure 107E:
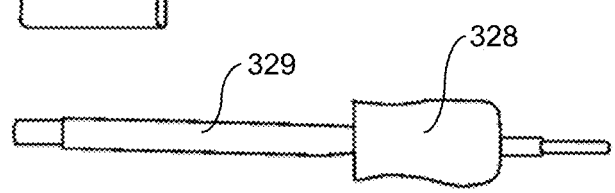

FIG. 107e shows a modified kit arrangement with added interface or adapter component 336 that facilitates the connection between the base end of instrument 329 and base collar 334. This adapter 336 can be relied upon to bridge the gap when the cavity of the collar 334 is too large for the instrument intended. Also, the central cavity of collar 328 is preferably designed to preclude passage of the base of the instrument out through the non-receiving end of collar 334. A central cavity such as that shown in FIG. 104d is an illustration of a suitable type cavity in this regard. As for finger holding collar 328, a sufficiently retaining smooth circular cylinder cavity can be utilized or a stepped arrangement that coordinates with a step down (330A and 330B) in the instrument's body as represented by the step down 336 shown in FIG. 107e. If the adapter 336 has a non-circular interior that matches that of the tool shaft's base there can be provided an arrangement designed not to have relative spinning between the tool base and adapter/collar combination. On the other hand the adapter 336 can provide a free spin hub, with the fingertip collar 328 providing spin control.

With reference to FIGS. 108a to 108d an illustration of the versatility and benefits of the kit combination 227 shown in FIG. 59 is provided. That is, the combination of base mount 221 and collar 225 provides for one handed removal as well as the ability for a person to take a variety of grasping approaches including approaches made available to a person with arthritis that would otherwise be unable to open the bottle.

Figure 108A:
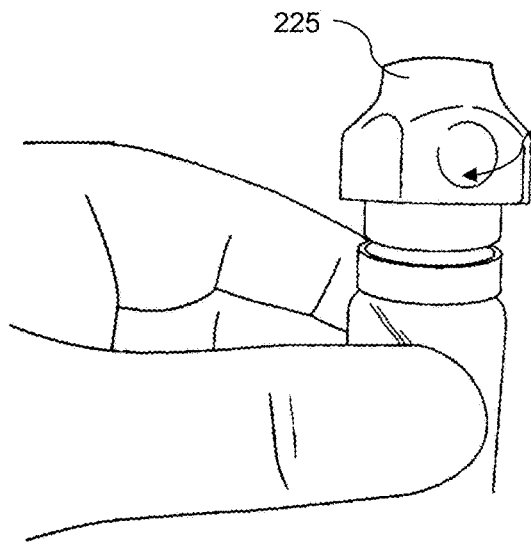
FIGS. 108a to 108e illustrate various views relative to a combination of a collar of FIG. 11 configuration in use with a bottle mount of FIG. 3a and some of the various hand positions and component positions utilized for bottle cap removal.

For example, FIG. 108a shows a grasp that a person with two free hands could take as with one hand holding the bottle and pushing down into the mount 221 (not shown in FIG. 108a), while the other hand (not shown) can readily grasp and compress collar 225 (e.g., fingers within the recesses to compress against the underlying threaded cap) and then rotate off. There is an enhanced torque capability here with two components spaced apart (collar and mount) and each able to provide friction resistance in appropriate direction.

Figure 108B:
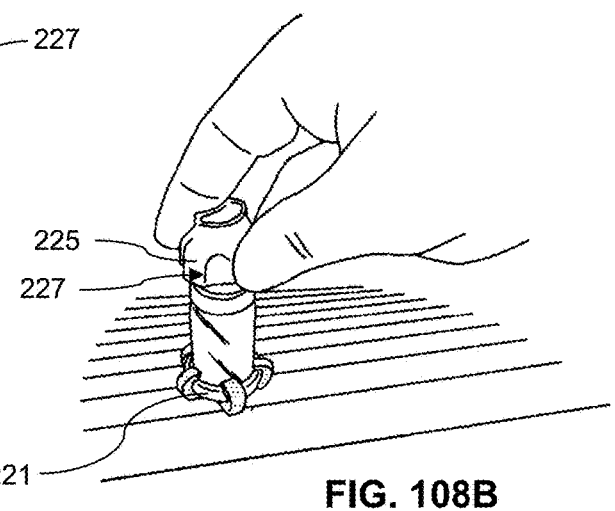
Figure 108C:
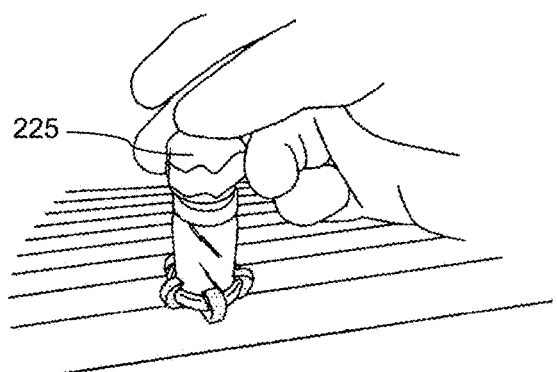
Figure 108D:
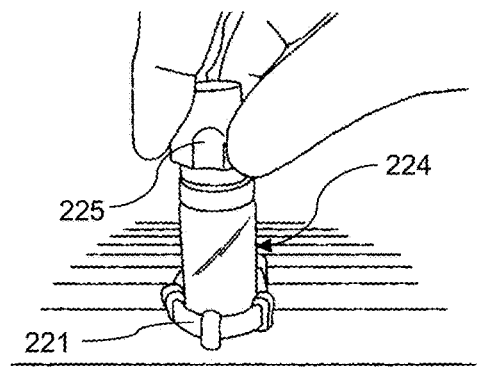
Figure 108E:
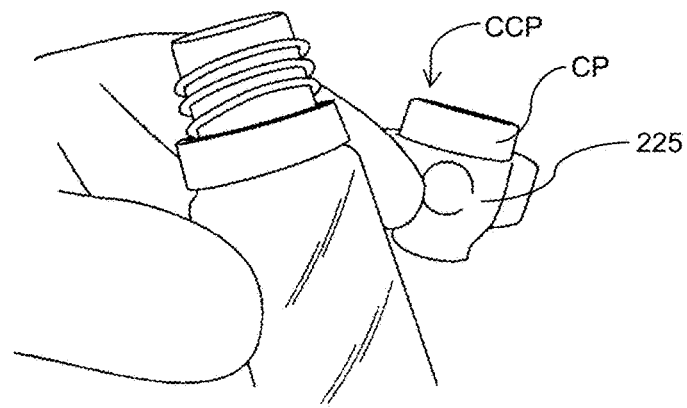

For situations or for personnel not having a second hand free, the present combination 227 allows for one hand cap removal. For example, each of FIGS. 108b, 108c and 108d illustrate single hand bottle removal capability (either relative to a pre-set up combination kit or one where a single hand free user carries out both collar and mount installation before cap removal). In the situation where the person does all stages in entirety, a suitable sized mount is set on a surface whereupon the bottle is slipped into the ribs 27 for friction retention. Once the bottle is mounted, the collar 225 can be readily flexed and inserted onto the bottle cover (in similar fashion to collar attachment to the bulbous head in FIG. 74). Following collar 225 attachment, the bottle cap can be readily removed due to the added grasping power provided by collar 225. That is, as shown in FIG. 108b the user can place one finger (e.g., the thumb) within one of the elongated grooves while a pair of fingers (e.g., the index finger and adjacent long finger) is placed upon the cone portion 190 with at least one finger compressing the free rim defining the open top or extending into the open top. In this way, there is sufficient friction retention as to initiate cap removal of the bottle while the bottle base is pressed down on mount 221 which frictionally precludes bottle rotation in favor of cap rotation.

FIG. 108*c* shows an alternate gripping approach that a person with arthritis might favor. As seen, the thumb is placed on the top opening with top rim contact and the two interior long fingers form a V-compression relationship on collar 225 with the combination being suitable for vertical press down and circumferential spin off without the need for thumb and adjacent most long finger pinching which can be difficult for some.

FIG. 108*d* shows yet another approach, where there is a three finger general vertical extension combination (thumb and adjacent most two long fingers) around collar 225, with each of the three fingers nested within a respective one of the concave recesses so that they are abutting a respective adjacent ridge. With the nestled fingers (and their abutment with a ridge that is ahead in the direction of spin off) coupled with an inward radial compression of the three fingers as well as a vertical mount compression force, the cap can be readily spun off.

Figure 109:
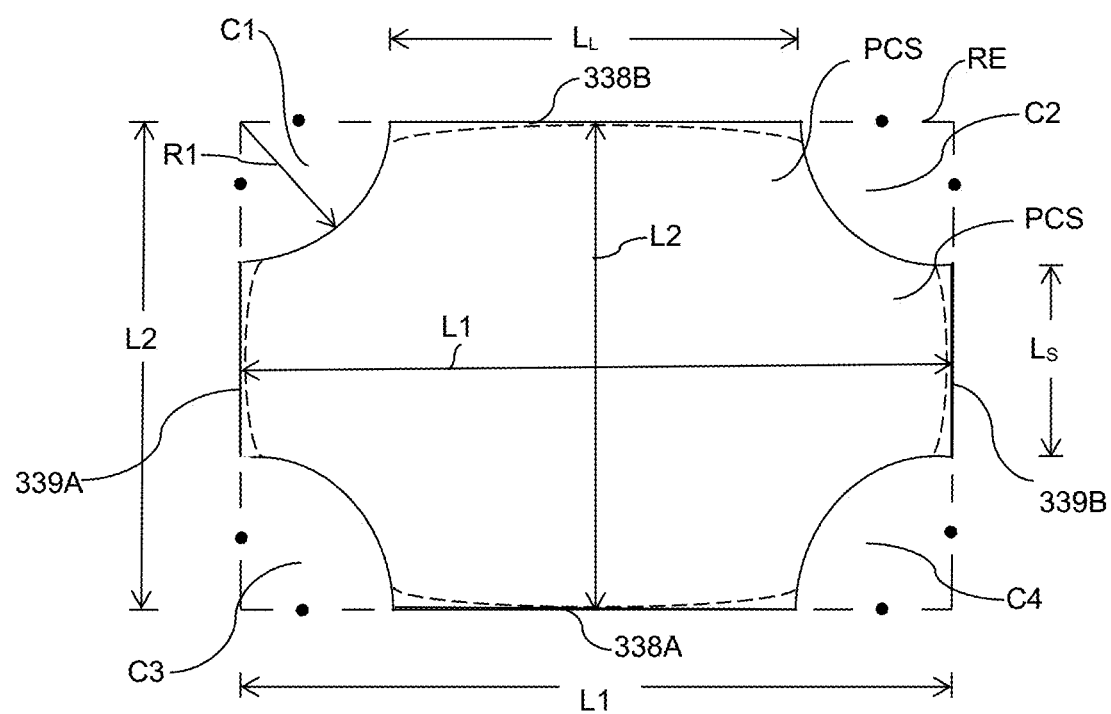
FIG. 109 shows a schematic depiction of a top plan view of a collar of FIG. 11 configuration with some of lengths and cavity depths demarcated.

FIG. 109 provides a schematic depiction of the collar configuration of FIG. 10*a* and shows a top plan view of a collar of FIG. 10*a* configuration with a long length L1 and a width length L2, together with corner "cut outs" (actually preferably molded in concavities) C1 to C4 each being concave with a general radius value R1. The corner concavity open areas C1 to C4 result in projection surfaces PCS on each of the long length projections (having surfaces 338A and 338B each of peripheral length $L_L$), as well as short length projections (having surfaces 339A and 339B each of peripheral length $L_S$). Also, a slight curvature can also be provided in each of the long and short sides as demarcated with dashed lines in FIG. 109 with the dot-dash lines reflecting the concavities where no material is present. For some of the intended uses of the present invention FIG. 10*a* configured collar, the length L1 ranges from, for example, 20 to 40 mm (e.g., 30 mm), the length L2 ranges from 10 mm to 30 mm (e.g., 18 mm), resulting in $L_L$ ranges from 8 mm to 18 mm (e.g., 13 mm), $L_S$ ranges from 4 mm to 10 mm (e.g. 6.5 mm) and radius R1 sufficient to enable finger reception with sufficient ridge interior wall friction contact, with suitable concave edge-to-edge distancing of 5 to 15 mm as in 8 mm (sufficient for enough insertion in most finger sizes), coupled with a radius of 8 mm to 12 mm as in 10.5 mm.

Figure 109A:
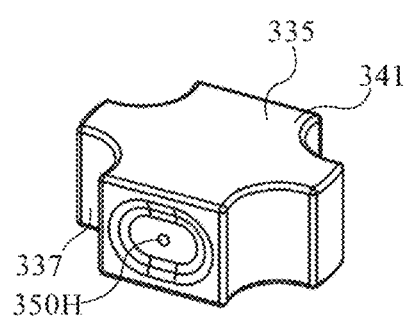
FIGS. 109a to 109n show a variety of different embodiments of thinner version collars of the FIG. 10a configuration.
Figure 109B:
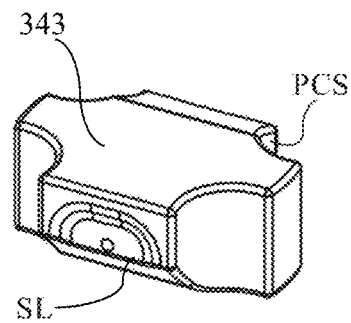

Figure set 109*a* to 109*n* illustrates a variety of examples of the collar configuration of FIG. 10*a*, with some of the features of this set being generally thin "height" lengths from forward to rearward planar ends 335, 337 (in which planes the central cavity intersects). For example, the "thinner" versions of the FIG. 10*a* collar feature lengths of, for example 2 to 13 mm, and more preferably about 6 mm to about 13 mm (the invention includes each value within this range and the end points; with the figure set of 109*a* to 109*n* including examples of thickness values of 6, 9 and 11 mm). Also, examples of different apertures are shown in the figure set of 109*a* to 109*n* with some of the apertures being through-holes and others being partial thickness apertures (extending for greater than a majority of the thickness). The apertures AP, at the boundary region with the above and/or below surfaces of the sleeves, preferably have downwardly sloping reception rims 339 to facilitate attachment to an object when so utilized. For example, FIGS. 109*a* and 109*b*, include capped tops 341 (FIG. 109*a*) and 343 (FIG. 109*b*) with the apertures extending therebelow to the lower end. FIGS. 109*a* and 109*b* illustrate side to side cavities as in a horizontal aperture (350 opening with similar on other side), with the cavity having, for example, the above described needle reception cavity with larger inlet opening (not shown). A tapered orientation in the central cavity is also featured. FIG. 109*b* also shows a sloped surface SL for fixed needle insertion incline purposes (e.g. 20°, 40°, 60° angle insertion).

The remainder of collars shown includes ones with smaller diameter apertures AP (e.g., 3.8 mm), medium diameter apertures AP (e.g., 6.2 mm to 10 mm) and larger relative diameter apertures AP (>10 to 13 mm) relative to the peripheral overall sizes featured in FIGS. 109*c* to 109*n*.

Figure 109C:
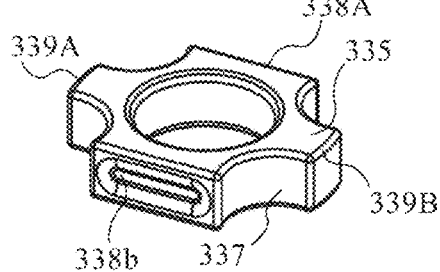
Figure 109D:
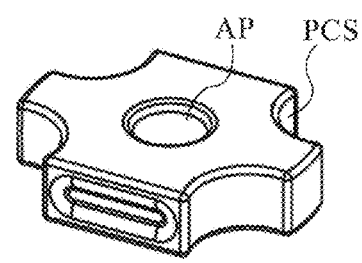
Figure 109E:
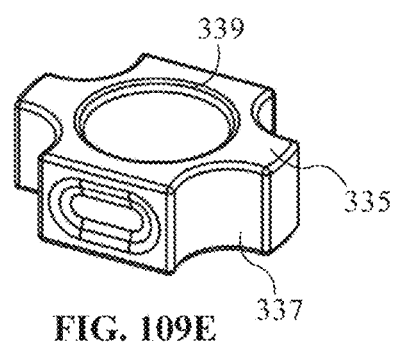
Figure 109F:
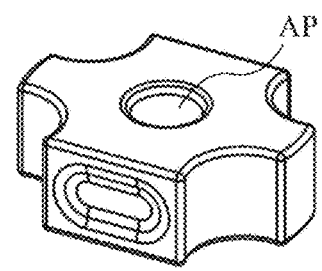
Figure 109G:
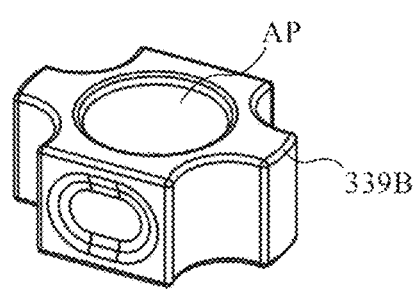
Figure 109H:
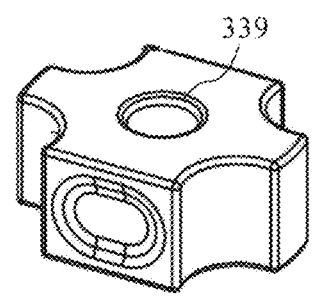
Figure 109I:
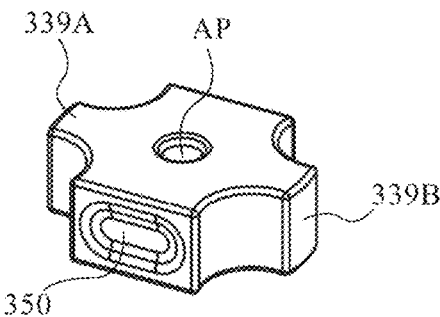
Figure 109J:
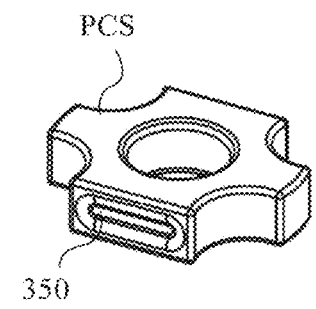
Figure 109K:
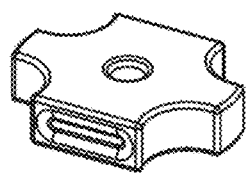
Figure 109L:
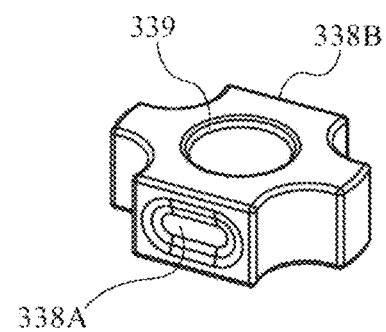
Figure 109M:
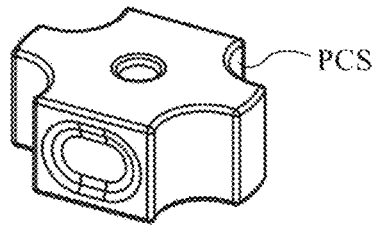
Figure 109N:
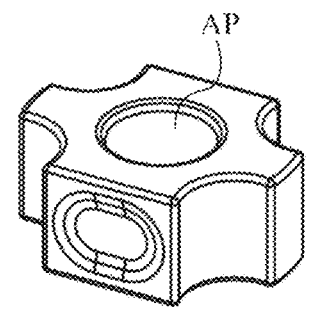

As shown in FIG. 109*c* the radius R1 of each concavity, which is generally in the form of a semi-circle, is set at, for example, 8 mm to 15 mm for the collars shown in FIGS. 109*a* to 109*n*. In alternate embodiments different radius concavities can be featured, with an object being to provide suitable grasping surfaces PCS wherein fingers can be inserted in the concavities and compression forces applied to the ridges having PCS surfaces to each side. Further, the collar embodiments shown in FIGS. 109*a* to 109*n* of the thinner height type, feature apertures of one diameter through the thickness, although alternate embodiments feature varying diameter values along the length of an aperture AP, such as the different stepped and sloped configurations described below for the FIG. 10*a* type collars of the longer height mode.

Fig. sets 110*a* and 110*b*; 111*a* and 111*b*; 112*a* and 112*b*; 113*a* and 113*b*; 114*a* and 114*b*; 115*a* and 115*b*; 116*a* and 116*b*; 117*a* and 117*b*; 118*a* and 118*b*; 119*a* and 119*b*; and 120*a* and 120*b* show examples of the FIG. 10*a* collar configuration with thicker or long heights as well as a variety of aperture AP variations. The plan view for collars of FIG. 10*a* type configuration and associated lengths and widths provided in FIG. 109 are applicable for the above thicker embodiments referenced in this paragraph. The "thicker" embodiments of the present invention are generally greater than 13 mm as in 14 mm to 50 mm in thickness, with examples presented in the figure set of this paragraph including values of 14 mm, 14.5 mm, 17 mm, 22 mm, 27 mm, 31 mm, 40 mm and 48 mm.

Figure 110A:
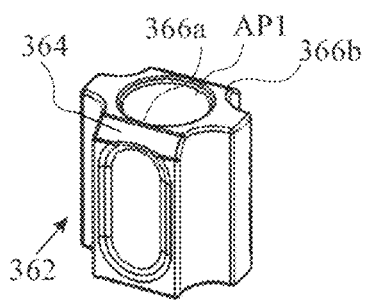
FIGS. 110a and 110b illustrate a longer or thicker version of the collar configuration of FIG. 10a with the former showing a perspective view and the latter showing a central vertical cross-section and the aperture configuration.
Figure 111A:
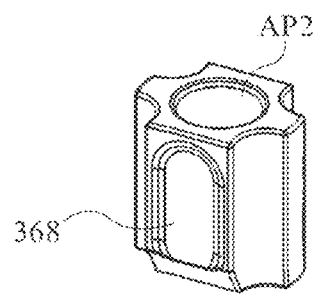
FIGS. 111a and 111b illustrate a longer or thicker version of the collar configuration of FIG. 10a with the former showing a perspective view and the latter showing a central vertical cross-section and the aperture configuration.
Figure 110B:
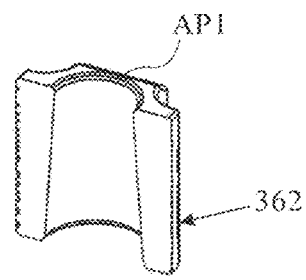

In Fig. set 110*a* and 110*b* collar 362 represents a collar well suited as a connecting collar between a vial and a syringe, with a collar thickness or height of 27 mm. As shown in the cross-section view of FIG. 110*b*, aperture AP1 has a frusto-conical shape that features a diverging top to bottom shape having an uppermost diameter of 13 mm and a lowermost diameter of 16.5 mm, which makes the top well suited for syringe insertion, and the bottom well suited for vial attachment. FIG. 110*a* also shows sloping shelf 364 at the top end of each of the long length ridges 366A and 366B.

Figure 111B:
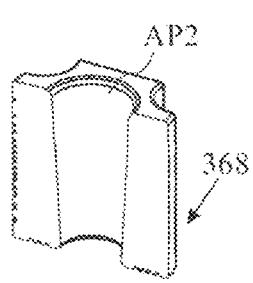

In Fig. set 111*a* and 111*b* collar 368 represents a collar well suited as a connecting collar between a vial and a syringe, with a collar thickness or height of 27 mm. As shown in the cross-section view of FIG. 111*b*, aperture AP2 has a frusto-conical shape that features a converging top to bottom shape having an uppermost diameter of 13 mm and a lowermost diameter of 10 mm, which makes the top well suited for syringe insertion, and the bottom well suited for a smaller sized vial attachment.

Figure 112A:
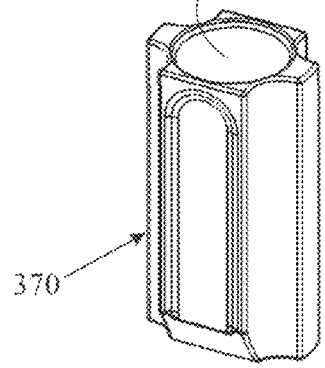
Figure 112B:
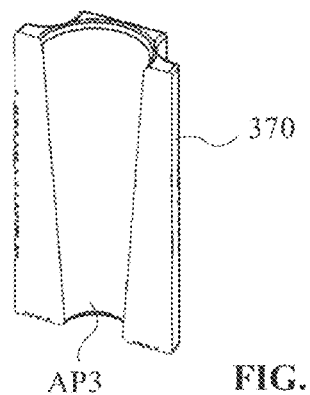

In Fig. set 112*a* and 112*b* collar presents two cross sectional views of collar 370. Collar 370 represents a collar well suited as a connecting collar between a vial and a syringe, with a collar thickness or height of 48 mm. As shown in the cross-section views of FIGS. 112*a* and 112*b*, aperture AP3 has a frusto-conical shape that features a converging top to bottom shape having an uppermost diameter of 17 mm and a lowermost diameter of 9.5 mm which makes the top well suited for syringe insertion, and the bottom well suited for smaller vial attachment.

In Fig. set 113a and 113b collar 372 represents a collar well suited as a connecting collar between a vial and a smaller diameter syringe, with a collar thickness or height of 17 mm. As shown in the cross-section view of FIG. 113b, aperture AP4 has a frusto-conical shape that features a diverging top to bottom shape having an uppermost diameter of 6 mm and a lowermost diameter of 14.5 mm which makes the top well suited for small diameter syringe insertion, and the bottom well suited for vial attachment.

In Fig. set 114a and 114b collar 374 represents a collar well suited as a connecting collar between a vial and a smaller diameter syringe, with a collar thickness or height of 17 mm. As shown in the cross-section view of FIG. 114b, aperture AP5 has a frusto-conical shape that features a diverging top to bottom shape having an uppermost diameter of 6 mm and a lowermost diameter of 9 mm, which makes the top well suited for small diameter syringe insertion, and the bottom well suited for smaller vial attachment.

In Fig. set 115a and 115b collar 376 represents a collar well suited as a connecting collar between a vial and a smaller diameter syringe, with a collar thickness or height of 48 mm. As shown in the cross-section view of FIG. 115b, aperture AP6 has a frusto-conical shape bore that features a diverging top to bottom shape having an uppermost diameter of 9.5 mm and a lowermost diameter of 15.5 mm which makes the top well suited for an intermediate diameter syringe insertion, and the bottom well suited for vial attachment.

In Fig. set 116a and 116b collar 378 represents a collar well suited as a connecting collar between a vial and a syringe, with a collar thickness or height of 40 mm. As shown in the cross-section view of FIG. 114b, aperture AP7 is made up of a smaller diameter circular cylindrical bore AP7A that opens out into a larger diameter circular cylindrical bore AP7B. Upper bore AP7A has a 10 mm diameter in the illustrated embodiment, and lower bore AP7B has an 18 mm diameter in this embodiment, which makes the top well suited for small diameter syringe insertion, and the bottom well suited for larger vial attachment. Also the axial length of the top bore is preferably longer than the axial length of the lower bore as in 80% length in the top bore and 20% length in the lower bore or 75% length in the top bore and 25% length in the lower bore and points therebetween these two ranges.

Figure 116A:
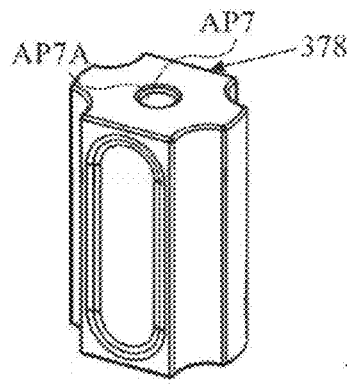
Figure 116B:
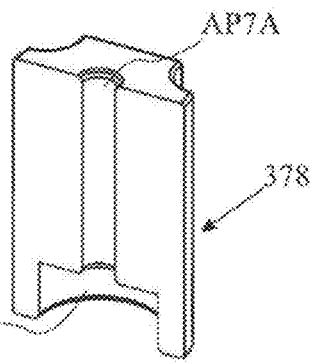
Figure 117A:
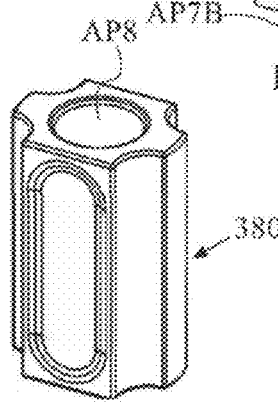
Figure 117B:
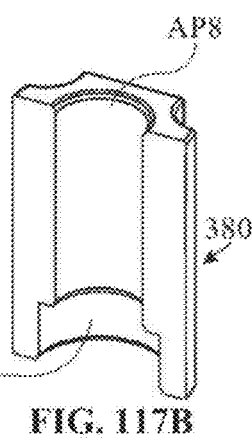

In Fig. set 117a and 117b collar 380 represents a collar well suited as a connecting collar between a vial and a syringe, with a collar thickness or height of 40 mm. As shown in the cross-section view of FIG. 117b, aperture AP8 is made up of a smaller diameter circular cylindrical bore AP8A that opens out into a larger diameter circular cylindrical bore AP8B. Upper bore AP8A has a 13 mm diameter in the illustrated embodiment, and lower bore AP8B has an 18 mm diameter in this embodiment, which makes the top well suited for intermediate diameter syringe insertion, and the bottom well suited for larger vial attachment. The same bore length ratio ranges as discussed above for FIG. 116b is applicable here.

Figure 118A:
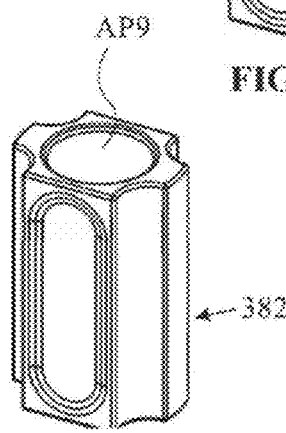
Figure 118B:
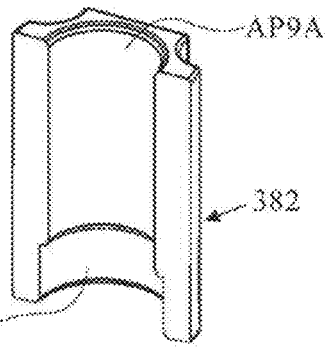

In Fig. set 118a and 118b collar 382 represents a collar well suited as a connecting collar between a vial and a syringe, with a collar thickness or height of 40 mm. As shown in the cross-section view of FIG. 118b, aperture AP9 is made up of a smaller diameter circular cylindrical bore AP9A that opens out into a larger diameter circular cylindrical bore AP9B. Upper bore AP9A has a 15.5 mm diameter in the illustrated embodiment, and lower bore AP9B has an 18 mm diameter in this embodiment, which makes the top well suited for intermediate to larger sized diameter syringe insertion, and the bottom well suited for larger vial attachment. The same bore length ratio ranges as discussed above for FIG. 116b is applicable here.

Figure 119A:
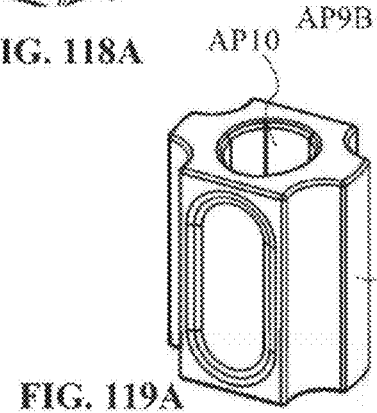
Figure 119B:
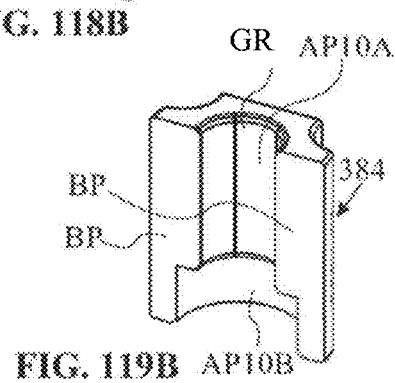

In Fig. set 119a and 119b collar 384 represents a collar well suited as a connecting collar between a vial and a syringe, with a collar thickness or height of 31 mm. As shown in the cross-section view of FIG. 119b, aperture AP10 is made up of a smaller diameter circular cylindrical bore AP10A that opens out into a larger diameter circular cylindrical bore AP10B. Upper bore AP10A has a 13 mm diameter in the illustrated embodiment, and lower bore AP10B has an 18 mm diameter in this embodiment, which makes the top well suited for intermediate to larger sized diameter syringe insertion, and the bottom well suited for larger vial attachment. An additional feature of upper bore AP10A is that it has equally circumferentially spaced grooves GR providing a plurality of individual bore pads BP extending radially inward and which provided an added degree of flexing and accommodation for an object insertion as in the referenced syringe. In the embodiment described here and above featuring a syringe/vial combination, the collars are also adaptable to connecting different lower and upper components rather than the exemplified syringe and collar combination for connection. Also, the same bore length ratio ranges as discussed above for FIG. 116b is applicable here.

In Fig. set 120a and 120b collar 386 represents a collar well suited as a connecting collar for a syringe's needle assembly, with a collar thickness or height of 22 mm. As shown in the cross-section view of FIG. 120b, aperture A11 is made up of a series of different diameter regions including a smaller diameter circular cylindrical bore AP11A that opens out into a larger diameter circular stacked frusto-conical bore arrangement AP11B (similar to that described above for collar 314), followed by an intermediate diameter bore AP11C which in turn opens out into a larger diameter needle reception/insertion bore AP11D.

Fig. set 121a and 121b shows collar 388 as being similar to that described above for Fig. set 120a and 120b, but having a smaller diameter upper bore as for a finer diameter needle shaft. The aperture sections AP12A, AP12B, and AP 12D share a common shape with that of FIG. 120b, but are designed for smaller needle assembly reception. Also, sloped wall SL provides for a controlled needle insertion angle as in 40° to 60° needle insertion.

Figure 120A:
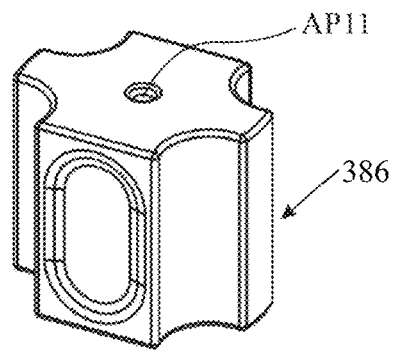
Figure 121A:
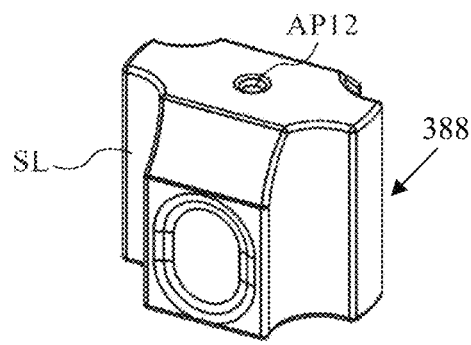
Figure 120B:
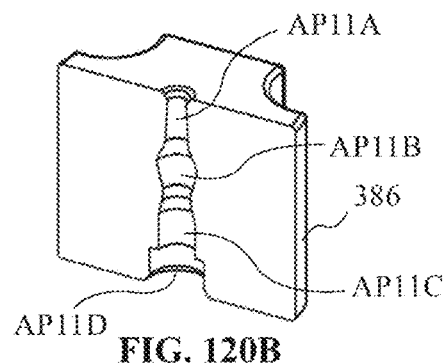
Figure 121B:
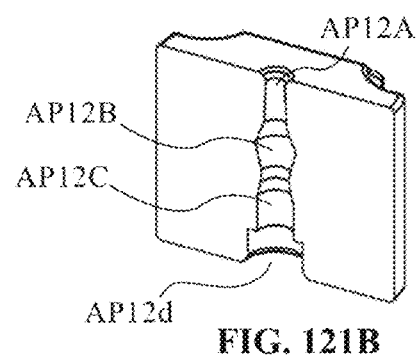
Figure 122A:
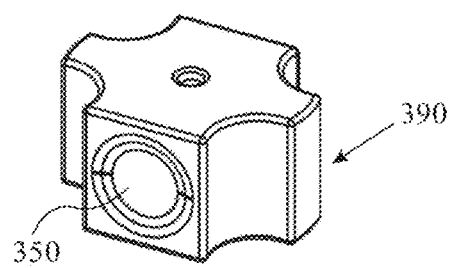
Figure 123A:
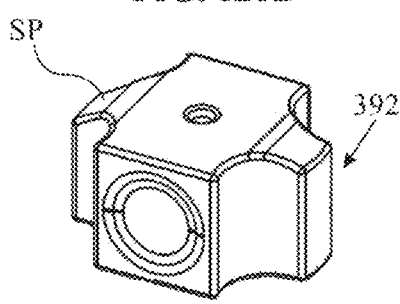
Figure 122B:
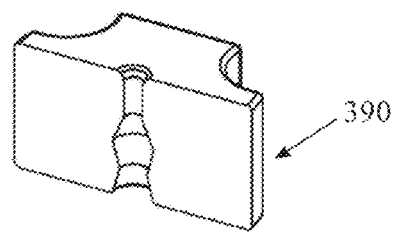
Figure 123B:
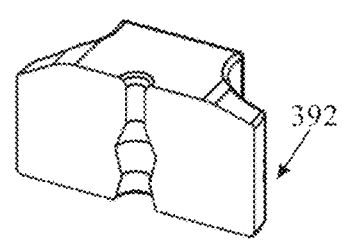

Fig. sets 122a and 122b as well as 123a and 123b (featuring collars 390 and 392), closely conform, respectively, to the above described collars in FIGS. 120a and 121a, but have a thinner body (14 mm rather than 22 mm). Also, sloped surface SP provides for a controlled needle insertion angle as in 15°-30°.

In Fig. set 124a and 124b collar 394 represents a collar of the FIG. 11 configuration (and thus has the attributes described above for collars of the FIG. 11 configuration) and represents a collar well suited as a connecting collar between a vial and a syringe, with a vertical collar thickness or height of, for example, 10 to 30 mm (e.g., 20 mm). As shown in the cross-section view of FIG. 124b, aperture AP13 is made up of a smaller diameter circular cylindrical bore AP13A (e.g., 3 to 6 mm) that opens out into a larger diameter circular cylindrical bore AP13B (e.g., 8 to 20 mm). In this embodiment, upper bore AP13A has a 6 mm diameter, and lower bore AP13B has an 18.5 mm diameter, which makes the top well suited for syringe insertion, and the bottom well suited for vial (canister or bottle type) attachment. The bore length for each of the upper and lower bore sections is about equal as in 50/50 or (60/40 to 40/60 as representative relative bore length ratios for bores AP13A and AP13B).

Also, FIGS. 125a to 130b can have an external periphery similar to that described above for the FIG. 10 at type collar set.

In Fig. set 125a and 125b collar 396 represents a collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 125b, aperture AP14 is made up of a smaller diameter circular cylindrical bore AP14A that opens out into a larger diameter circular cylindrical bore AP14B. Upper bore AP14A has, for example, a 6 mm diameter in the illustrated embodiment, and lower bore AP14B has an 10 mm diameter (smaller vial than FIG. 124a) in this embodiment, which makes the top well suited for syringe insertion, and the bottom well suited for vial (canister or bottle type) attachment. The bore length ratios here conform with that described in FIG. 124a).

In Fig. set 126a and 126b collar 398 represents a collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 126b, aperture AP15 is made up of a smaller diameter circular cylindrical bore AP15A that opens out into a larger diameter circular cylindrical bore AP15B. Upper bore AP15A has a "large mouth" 13 mm diameter well suited for syringe with grasping collar as described, for example, in the disclosure for FIGS. 59, 61 and 62 illustrated embodiment, and lower bore AP15B has an 18.7 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length rations for bores AP15A and AP15B).

In Fig. set 127a and 127b collar 400 represents a closed top collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 127b, aperture AP16 is in the bottom half only while the upper half is solid with the elastomeric material forming the collar of FIG. 11 configuration. This closed top is of a thickness that is suitable for needle puncture when access to the vial is desired. The vial is connected to collar 400 by way of aperture AP16 which in this embodiment has an 8 mm diameter. The FIG. 127a embodiment is well suited for smaller vial containers and thus has an upper solid puncture area of 8 mm and a larger exterior as in 11.8 mm, with 8.5 mm vial capture recess diameter and a height of 7.5 mm.

In Fig. set 128a and 128b collar 402 represents an open top/closed bottom collar of the FIG. 11 configuration (and thus has the attributes described above for collars of the FIG. 11 configuration) and represents a collar well suited as an insertion location for the base of an object as in the plunger flange of a syringe, such as shown in FIG. 40. As shown in the cross-section view of FIG. 128b, aperture AP17 is in the upper half only while the lower half is solid (e.g., 2 mm thickness for a 7.5 mm height collar) with the elastomeric material forming the collar of FIG. 11 configuration. The open top has a diameter of, for example, 6 mm.

In Fig. set 129a and 129b have collar 404 that represents a collar of the FIG. 11 configuration (and thus has the attributes described above for collars of the FIG. 11 configuration) and represents a collar well suited as a connecting collar between a vial and a syringe, with a collar thickness or height of about 18 mm. As shown in the cross-section view of FIG. 129d, aperture AP18 is made up of a smaller diameter circular cylindrical bore AP18A that opens out into a larger diameter circular cylindrical bore AP18B. Upper bore AP18A has a relatively small 2 mm diameter in the illustrated embodiment, and lower bore AP18B has an 18.5 mm diameter in this embodiment, which makes the top well suited for needle insertion, and the bottom well suited for vial (canister or bottle type) attachment. The bore length for each of the upper and lower bore sections is about equal as in 50/50 or (60/40 to 40/60 as representative relative bore length rations for bores AP18A and AP18B).

In Fig. set 129c and 129d collar 406 represents a collar of the FIG. 11 configuration (and thus has the attributes described above for collars of the FIG. 11 configuration) and represents a collar well suited as a connecting collar between a vial and a syringe, with a collar thickness or overall height of 18 mm. As shown in the cross-section view of FIG. 130b, aperture AP19 is made up of a relatively smaller diameter circular cylindrical bore AP19A that opens out into a larger diameter circular cylindrical bore AP19B. Upper bore AP19A has a 10 mm syringe reception diameter in the illustrated embodiment, and lower bore AP19B has an 18.5 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length rations for bores AP19A and AP19B).

FIGS. 130a to 130c, provide an example of a combination 200 comprised of collar 202 (of FIG. 11 configuration) and mount 204 (of FIG. 3a configuration) being used to hold a needle cover 206 (following its insertion into the enlarged open end of collar 202 until becoming trapped in the smaller diameter portion of the collar cavity such as the cavity arrangement shown in FIG. 129b). With the needle cover 206 in position as shown in FIG. 130a and the collar frictionally retained on the support surface in a tilted up direction, the user can insert with one hand H the needle assembly 208, as shown in FIG. 130b, such that the needle shaft enters into the enlarged open end of collar 202. Once sufficiently inserted the user, with the same single hand, can then grasp the top end of collar 202, with needle casing extending there-away, and pull it toward the base mount 204 (or simultaneous toward each other or hold the collar and move the mount forward) to achieve a snapped engagement of the needle in the needle cover (as depicted in FIG. 130c).

The FIG. 130b embodiment also illustrates how, with the same single finger downward compression used to enter the needle, there can be achieved separation. That is, with collar 202 pinned to the surface with a single finger, the user can retract the vial with other fingers of that same hand to achieve separation of the needle assembly and collar 207.

FIGS. 131a to 131c show tray 210 with a set of different size mounts (212A and 212B) each of the FIG. 3a configuration. The different size mounts 212A and 212B are nested in a generally common plane arrangement with mount 212A circumferentially exterior, but engaging with the inward mount 212B. Mount 212A has its ridges received in the accommodating recesses 213 formed in aperture 216 of tray 210 (in similar fashion to the arrangement described above for the tray in FIG. 30), while mount 212B has its ribs contacting the annular core of mount 212A and with the ribs being retained between two adjacent ribs of mount 212A so as to be frictionally fixed in position. Thus, by this nesting arrangement, a utensil 218 (a specimen vial), that is too narrow for a good holding fit in collar 212A, but can be securely received in the appropriate sized (good friction retention of the vial without tilt) mount 212B. In this way, the tray has greater functionality and is able to handle a wider variety of sized utensils so as to make it more universal in use.

Also, FIG. 131a reveals a triple nested arrangement of mounts with mounts 214X (largest), 214Y (intermediate diameter), 214Z (smallest) arranged like the nested common plane arrangement shown for mounts 212A and 212B. As seen the diameter of collar 214X is larger than that of 212A making it suited for receipt in a larger aperture provided in tray 210 (see FIG. 39 as an example of different sized tray apertures). Thus, the set of mounts involving mount 214X can be retained in a larger aperture in the tray and still hold a smaller diameter vial as in vial in that are used to adjust the size of a tray aperture (e.g., see FIG. 39 example tray) such that a smaller utensil can fit in a larger aperture.

FIG. 131b shows vial 218 having been inserted into the appropriate sized mount 214Z such that it is frictionally retained in straight up-right position when properly inserted. FIG. 131b also shows that this stable positioning is present while the nested set involving mount 214Z is merely resting on a support surface and not yet inserted into the confining aperture provided by tray 210 (the aperture not shown in the cut-away tray but see again FIG. 39).

FIG. 131c shows the vial 218 in a one hand H transportation position while retained in the nested set involving mount 214Z, and with the user able to pick-up and move the vial without detachment of any of the three mounts in the nested set involving mount 214Z. Also, with the increased diameter base support there is provided a more stable platform with the X-Y-Z rested mounts, such that the vial can be placed on a vibrating surface (mix retention or anti-coagulation vibration means) without fear of knock over and without the need for a special vial holder for designated use with the vibration means.

FIGS. 132a to 132c show a double set kit of mounts 220A and 220B (each of the FIG. 3a configuration and, in this embodiment, of a common size). Mounts 220A and 220B are shown holding together an assemblage of different utensils (inclusive of utensil having additional components of the described embodiments). As seen, mounts 220A and 220B securely hold together a plurality of different sized and shaped components. In the example shown in FIG. 132a, there is held in place two bottles B1 and B2 and two syringes S1 and S2, each extending vertically within the interior of the respective annular collars featured in mounts 220A and 220B and each held in a radial compression state by the annular collars and ribs of the respective collars. Also, mounts 220A and 220B are arranged in a vertical stack (with separation between the annular rings and ribs in this embodiment). Further, the mounts 220A and 220B have their ribs oriented such that the underling rib surface (see 228 in FIG. 133b below) designed to support the underside of a bottle of mount 220B, represents a downward compression surface in top mount 220A such that the downward force of the ribs in mount 220A work together with the upward force of the ribs in mount 220B. The combination of mounts 220A and 220B provides for ease in transport with one hand H of a user, either by holding one of the more upper regions of the trapped components (132a), holding one or more of the mounts (FIG. 132b); or holding the bottom region of the trapped components in the cup shaped exposed palm (FIG. 132c). Also, the ribs contact different items in the assembly as to help avoid both vertical shifting and rotation shifting within the rings 220A and 220B.

FIGS. 133a to 133d further show the versatility of the mount of FIG. 3a configuration, with FIG. 133a showing mount 222 mounted securely on cap C of bottle B3 (such as a soda bottle). FIG. 133b show various cross-sectional views of mount 222. As seen and in similar fashion as to FIG. 3a, mount 222 comprises annular core 224 and a plurality of spaced ribs 226 shown equally spaced about the core. As further seen in FIGS. 133b to 133d, ribs 226 extend (preferably molded together as one unit with the annular core). FIG. 133b illustrates mount 222 in the top in the up position, while FIG. 133d shows the top of mount 222 in the down position. Thus, there is more efficiently seen the utensil bottom contact surface 228 in FIG. 133b which provides a planar surface (in combination with the other mutually common height positioned contact surfaces 228) for contact with the bottom of the utensil such as a flat bottomed utensil although the preferably pliable nature of the ribs provides for accommodation of other non-planar bottomed utensils. Ribs 226 are also shown as having an edge 226E made possible by the downward extending, exterior curved slope 230 of ribs 225 and the upward and radially outward extending slope leading 232 away from the edge. As noted above, this point edge contact helps stably position in an upright manner utensils while accepting misalignment until radial compression amongst the various ribs settles.

FIG. 134 shows a view of a pliable mount of FIG. 3a configuration which also shows how the accommodating ribs 226 in combination with the twisting, pliable nature of core 224 are able to accommodate a large tilt due to missed insertion of a medicine dropper bottle, or an actual intended oblique bottle orientation.

FIGS. 135a to 135d illustrate various views of turret collar combination 234 comprised of turret collar 236 and an underlying platform 238 (preferably a spin and lock platform to provide a turret rotation function support to collar 234). That is. FIG. 135a shows turret collar combination 234 comprised of a modified collar 236 (generally of the FIG. 10a configuration) that is combined/retained (frictional reception contact holding relationship with rotation possible until a desired lock position is reached) by underlying platform 238. As seen, platform 238 has a saucer like configuration with a disc main body 240 having a circular periphery with smooth, upper contoured outer edging 242. Main body 240 further includes a planar upper surface 244 having at its center a raised mound that is generally semi-spherical turret mound 246. As seen in FIG. 135b, turret mound 246 is designed for extension into a conforming recess 250 conveniently provided as part of a through-hole aperture APT that extends through the thickness of the collar. Platform 238 further includes a preferably channeled (preferably a plurality of concentric channels formed in the undersurface of platform 238 as represented by channels 252 shown in cross-section). Also, platform 238 is preferably a soft, pliable material such as silicone rubber as to provide for frictional position retainment as to provide a stable turret support and also for accommodating variations in body surface when used as a medical instrument. Mounting of the platform can also be made even more position secure via use of temporary adhesive as used in EKG pads such as those with removable non-adhesive cover sheeting). Suitable dimensions for platforms 238 includes a diameter of 15 to 30 mm as in 20 mm, a thickness plate of 1 mm to 4 mm as in 1.7 mm, a bulb 246 height of 3 to 7 mm (as in 4 mm) and a bulb diameter of 4 to 8 mm as in 6.3 mm.

Collar 236 is preferably provided with a sloped (long collar ridge side to opposing long collar ride side) through-hole 254 that is conical in shape and shown as slanting downward from its larger insertion end 254A to its narrower exit end 254B lying at the lower extremity of finger depression recess 256. Also, through-hole 254 also is bisected by aperture AP such that it opens at two interior points into aperture APT. In this way porting is provided vertically in aperture APT and also through the long length of collar 236 with aperture APT in communication with the through-hole. Some non-limiting illustrative dimensions for components of collar 236 include a thickness height of 10 to 15 mm as in 11 mm, an aperture 258 oval of 2 mm height, 5 mm length, and a maximum length (short ridge to short ridge) of about 20 to 30 mm (e.g., 26.2 mm).

Collar 236 is provided with additional porting via an oblong (e.g., oval) passageway 258 with open end 258A shown in FIG. 135a (and a full cross-sectional view provided in FIG. 136c which is described below). Passageway 258 extends the full length from short-ridge side to short-ridge side of the main body of collar 236 (see PR as short ridge example in FIG. 135d) and also bisects with the aperture APT such that each extension opens into the central aperture APT as also depicted in FIG. 136a. Passageway 258 is preferably arranged to pass in the lower portion of the main body of collar 236 (the lower quarter relative to the height of the collar), but is preferably not blocked off by the bulbous turret mound 246. In this way the smooth contour of the top of mound 246 can help in the feeding of elongated instruments through the desired porting including passageway 258 which opens into aperture APT in that region.

FIGS. 135e and 135f illustrate a modified turret collar 260 having similar features as described above for turret collar 236, but rather than a conical through-hole that is tilted, there is provided through-hole 262 that has a common diameter along its entire length (each extension thereof extending to opposite sides of aperture APT which is in communication with through hole 262) and is arranged in horizontal fashion. That is, opening 262A is at the same height level as opening 262B, with the latter opening out at the center of finger depression recess 256 rather than at its lower edge in the earlier embodiment. FIG. 135f also illustrates the turret recess 250 lying just below and in communication with passageway 258.

FIGS. 135g and 135h show a modified embodiment of the turret collar described above. In this embodiment turret collar 264 includes generally the same collar configuration but features the lower passageway 258' as passing not between the opposing short length ridges PR but between the opposing long side ridges LR. Thus, the oblong opening of passageway 258 opens out at the lower region of finger depression recess 256. Also, through-hole 254' is similar to through-hole 254 described above (sloped and conical), but instead extends through the collar body and aperture APT from short side ridge PR to its opposing ridge (PR). As seen from FIG. 135h, the slope results in opening 354B' being in the lower quarter of collar body height and the enlarged opening 254' in the upper quarter of height of collar 264.

FIGS. 135i and 135j show turret collar 266 which has the same configuration as that of turret collar 264 but for rather than a tilting through-hole such as through-hole 254' in FIG. 135h it has a horizontal through-hole 268 (while also retaining the conical configuration featured in through-hole 254', however).

FIGS. 136a to 136c illustrate collar 236 of FIG. 135a removed from its mount, with FIG. 136a showing a perspective view of the collar with an angled thin tool (e.g., a flexible or non-flexible tool as in one <3 mm in diameter and preferably less than 1 mm) inserted into through-hole 254, as in through opening 254A and down through to the opposite opening 254B whereupon the tool extends to both sides of collar 235 (e.g., a tool as in a needle, a sheath (e.g., a catheter sheath), a wire, a fluid tube, etc.). While turret collar 236 is mentioned for receipt of insert tooling or utensils, depending on the circumstances, any of the other above described turret collars can be utilized for insertion(s) of such tools or utensils.

FIG. 136b shows a front elevational view of that which is shown in FIGS. 136a, and 136c shows a cross-sectional view along cross-section A-A in FIG. 136b (which represents a horizontal bisect of passageway 258). As further seen from FIG. 136b inserted tool IT can extend above and below the respective top plane and bottom planes TP and BP of collar 236 (with the lower one potentially illustrating a below skin entry point).

FIG. 137 shows another embodiment of a turret collar 270 which is similar to collar 236 but for a different through-hole 272 that replaces through-hole 254 in collar 236. That is, through-hole 272 has an oval or oblong shape like passageway 258, but has its major diameter extending vertically rather than horizontally like for passageway 258 (e.g., 1 mm minor diameter and 3 mm major diameter). There is still retained a downward slope as seen by the IT ends being at different height in FIG. 136. As shown in the enlarged detail in FIG. 137A, through-hole opening 272A has a smooth lead in edge 274 which defines the IT insertion hole 276. The minor axis diameter for this insertion hole can be sized as to provide some frictional resistance from upward or downward adjustment in the IT relative to the maximum diameter direction for the oval shaped opening. In FIGS. 137 and 137A there is shown the tool IT in a shallow angle orientation wherein the IT tool contacts the bottom of the insertion opening 272 border.

FIGS. 138 and 138A depict the same turret collar 270 as in FIG. 137, but has the IT tool adjusted up to a maximum angle such that tool IT abuts the upper extremity of the border defining through-hole opening 272A.

FIG. 139 shows the same view as FIG. 136a, but show the utensil as being a combination utensil ITC, having IT as described above as a hollow sheath initially inserted through the collar plus a feed though instrument ITI. Such an arrangement can represent a useful relationship in a variety of fields both medical and non-medical, but is particularly useful in the medical field as once the turret collar is mounted on its platform after the platform is placed in position (or a simultaneous mounting) and the ITC placed, it can be held in place or rotated to a different desired orientation in turret fashion. Additionally, sheath IT will retain its position while the interior instrument ITI can be threaded in one direction or the other. Examples including sheathed wiring assemblies, catheter sheath and insert combinations, fiber optics and line-up sheathing, etc.

FIG. 140 shows the arrangement of FIG. 139 rotated so that the inlet side of opening 272A is more visible rather than the outlet side 272B of FIG. 139.

FIG. 141 shows a similar view as that of FIG. 140 but with a position retainer insert 278 added. In this way there is added assurance of the desired upward positioned tool IT is retained relative to collar 272. FIGS. 141a to 141c show different variants of the position retainer insert 278 designed to hold the tool at a desired orientation within the receiving oblong or oval shaped opening provided in the collar for tool positioning flexibility. Also, the base of insert 278 is provided with a hole for insertion of a tool facilitating removal.

FIGS. 142a and 142b show different views of the combination 234 comprising a turret collar and swivel mount as shown in FIG. 136a, but with a modified turret collar (236') featuring a pair of clamp down wings 280A and 280B with wing platforms extending out of short side ridges PR at their base and supporting clamps 282A and 282B within reception grooves/ridging 281A and 281B. Clamp down wings provide a useful location for securement of the turret collar in place once the rotation position of the turret collar relative to the base represented by spin platform 238 is chosen. For example, clamp down wings can be, for example, stapled in position to the recipient support surface such as a patient. Also, clamp down wings can be threaded into an existing aperture such as 258.

FIG. 143 shows a swivel mounted collar 270 similar to FIG. 137 with an illustration of the numerous porting provided by passageways 258 and through-hole 272 and aperture APT communicating with all porting. Hence, a plurality of different utensils or one utensil having a plurality of different offshoots (e.g., instrument wiring or tubing) can be received therein and directed in a desired direction and slope (up or down) or horizontally. In FIG. 142 a series of wires are showing with five different exit points illustrated.

FIGS. 144 and 114a illustrate collar 270 of FIG. 137 further comprising plug device 284 just prior to insertion, with the plug device comprised of a base body 286 with a central aperture, a pin top 288 that is retained secured to base body 286 via tether 290. As shown, insertion of pin portion 287 of pin top 288 places its cap 289 in a closed state relative to the central aperture in the base body 286. As further shown in FIG. 144, pin top 288 has a central aperture CA, which can provide an insertion opening for a smaller instrument (a though-hole through the entire plug, for example) or a threading guide for an item retained in collar 270. The plug 284 also can close off and pin, if desired, instruments or tooling placed in aperture APT or though the various portings described above. FIG. 144a shows the collar and plug arrangement shown in FIG. 144 but from a side view. FIG. 144a also shows porting IP in the base body of the plug that can be used for threading of a thin instrument such as a flexible sheath, whereupon plug downward movement and/or rotation results in a crimping or braking function and/or a fluid blockage mode if fluid is passing through instrument IT.

FIGS. 144b to 144d show different length plug devices 284 (284' and 284") each with integrated pin caps that can be inserted to seal off the plug itself received by the collar. As shown, the base body can be adjusted in height so as to extend into aperture APT to a greater or lesser extent.

FIGS. 145 and 145A show the same collar 270 and plug device 284 featured in FIG. 144, but with the plug device 184 inserted into the aperture APT of collar 270 in sealing fashion. FIG. 145 also shows optional segregated porting XX that can be added if additional instruments are to be supported (e.g., those extending in generally common direction at least initially).

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

What is claimed is:

1. A grasping facilitator, comprising:
a pliable collar having a main body with a plurality of ridges separated by concave recesses and a central aperture, wherein the exterior periphery of the main body is defined by the plurality of ridges separated by concave recesses, and wherein each of the ridges has an outer surface defining an exterior side wall of the collar, and there is a first, opposing set of said side walls and a second, opposing set of said side walls, with the first set of said side walls being longer in length than the second set, and the concave recesses being positioned at locations between respective longer and shorter walls of said first and second sets, and wherein the first set of sidewalls and the second set of sidewalls are pliable such that, upon compression or tension of the pliable collar, the configuration of the central aperture is modified, and wherein the central aperture is a varying diameter aperture that includes a stepped region between opposite, exposed ends of the main body.

2. The grasping facilitator of claim 1 wherein the central aperture is a varying diameter aperture configured for needle assembly reception.

3. The grasping facilitator of claim 1 wherein the stepped region of the central aperture, defining the varying diameter aperture, is configured for bottle top connecting.

4. The grasping facilitator of claim 1 wherein the aperture extends through the main body as to open out at opposite ends of said main body.

5. The grasping facilitator of claim 4 wherein the central aperture is a varying diameter aperture that includes a first area aperture region at one of the opposite ends and a second area aperture region at the other opposite end, wherein the second area aperture region is larger than the first area aperture region.

6. The grasping facilitator of claim 5 wherein one of the aperture regions is configured to receive, in friction retention, a container, and the other one of the aperture regions is configured to receive, in friction retention, a syringe body component or a needle hub.

7. The grasping facilitator of claim 5 wherein the pliable collar is configured for stretched, friction retention of the container top at one of the opposite ends and a syringe at the other of the opposite ends.

8. The grasping facilitator of claim 1 wherein the varying diameter aperture further includes a tapering wall region.

9. The grasping facilitator of claim 8 wherein the varying diameter aperture with tapered wall region and stepped region is configured to frictionally retain a needle hub assembly.

10. The grasping facilitator of claim 1, wherein the aperture opens out at both of the first and second end walls and includes a first diameter region and a second, different diameter region along an axial length of the aperture as to define the stepped region, and wherein the first and second diameter regions are configured for friction, stretch retention of a syringe component and a top region of a container as to provide for syringe needle extension into the container.

11. The grasping facilitator of claim 1, wherein the main body has opposing upper and lower end walls, and the aperture defines an opening region in at least one of the opposing end walls, which opening region is configured for flexed, friction retention of a threaded bottle cap.

12. The grasping facilitator of claim 11, wherein the central aperture has a first diameter region and a second diameter region of a different size than the first diameter region, and the first diameter region is configured for the friction retention of the threaded bottle cap.

13. The grasping facilitator of claim 1, wherein the pliable collar is formed of a monolithic block of elastomeric plastic having a shore value range falling within that of medical grade silicone.

14. A grasping facilitator, comprising:
a pliable collar having a main body with a plurality of ridges separated by concave recesses and a central aperture, wherein the exterior periphery of the main body is defined by the plurality of ridges separated by concave recesses, and wherein each of the ridges has an outer surface defining an exterior side wall of the collar, and there is a first, opposing set of said side walls and a second, opposing set of said side walls, with the first set of said side walls being longer in length than the second set, and the concave recesses being positioned at locations between respective longer and shorter walls of said first and second sets, and wherein the first set of sidewalls and the second set of sidewalls are pliable such that, upon compression or tension of the pliable collar, the configuration of the central aperture is modified, and wherein a base region of the main body includes the plurality of ridges separated by concave recesses, and the main body further includes an upwardly converging extension rising above an upper edge of the ridges.

15. A grasping facilitator, comprising:
a pliable collar having a main body with first and second, opposing ends walls, an interior aperture, and an exterior periphery extending between the end walls, with the exterior periphery comprised of a plurality of ridges separated by recesses, wherein each of the ridges has an outer surface defining an exterior side wall of the collar, and there is a first, opposing set of said side walls and a second, opposing set of said side walls, with the first set of said side walls being longer in length than the second set, and the recesses being positioned at locations between respective longer and shorter walls of said first and second sets, and wherein the aperture defines an opening region in at least one of the opposing end walls, which opening region is configured for flexed, friction retention of a threaded bottle cap, with the plurality of ridges separated by recesses in the main body being positioned as to be on a common level with a portion of the aperture designed for friction retention of the bottle cap.

16. The grasping facilitator of claim 15 wherein the aperture extends internally within the main body as to open out at only the first of the opposing end walls.

17. The grasping facilitator of claim 15 wherein the aperture opens out at both of the first and second end walls and includes a first diameter region and a second, different diameter region along an axial length of the aperture.

18. A grasping facilitator, comprising:
a pliable collar having a main body with a plurality of ridges separated by concave recesses and a central aperture, wherein the exterior periphery of the main body is defined by the plurality of ridges separated by concave recesses, and wherein each of the ridges has an outer surface defining an exterior side wall of the collar, and there is a first, opposing set of said side walls and a second, opposing set of said side walls, with the first set of said side walls being longer in length than the second set, and the concave recesses being positioned at locations between respective longer and shorter walls of said first and second sets, and wherein the first set of sidewalls and the second set of sidewalls are pliable such that, upon compression or tension of the pliable collar, the configuration of the central aperture is modified, and wherein the main body has a needle puncture material covering extending over one end of the aperture within the main body.

19. A grasping facilitator, comprising:
a pliable collar having a main body with first and second, opposing ends walls, an interior aperture, and an exterior periphery extending between the end walls, with the exterior periphery comprised of a plurality of ridges separated by recesses, wherein each of the ridges has an outer surface defining an exterior side wall of the collar, and there is a first, opposing set of said side walls and a second, opposing set of said side walls, with the first set of said side walls being longer in length than the second set, and the recesses being positioned at locations between respective longer and shorter walls of said first and second sets, wherein the aperture extends internally within the main body as to open out at only the first of the opposing end walls, and wherein the aperture has a closed end over which extends the second of the opposing ends walls, and the closed end of the aperture is formed of a material of suitable strength to provide for needle bending upon needle insertion into the aperture.

20. A kit comprising:
a pliable collar having a main body with a plurality of ridges separated by concave recesses and a central aperture, wherein the exterior periphery of the main body is defined by the plurality of ridges separated by concave recesses, and wherein each of the ridges has an outer surface defining an exterior side wall of the collar, and there is a first, opposing set of said side walls and a second, opposing set of said side walls, with the first set of said side walls being longer in length than the second set, and the concave recesses being positioned at locations between respective longer and shorter walls of said first and second sets, and wherein the first set of sidewalls and the second set of sidewalls are pliable such that, upon compression or tension of the pliable collar, the configuration of the central aperture is modified; and
at least one member selected from the group consisting of a syringe, needle hub, and a capped container.

21. The kit according to claim 20 where the at least one member is the capped container.

22. A grasping facilitator, comprising:
a pliable collar having a main body with a plurality of ridges separated by concave recesses and a central aperture, wherein the exterior periphery of the main body is defined by the plurality of ridges separated by concave recesses, and wherein each of the ridges has an outer surface defining an exterior side wall of the collar, and there is a first, opposing set of said side walls and a second, opposing set of said side walls, with the first set of said side walls being longer in length than the second set, and the concave recesses being positioned at locations between respective longer and shorter walls of said first and second sets, and wherein the first set of sidewalls and the second set of sidewalls are pliable such that, upon compression or tension of the pliable collar, the configuration of the central aperture is modified, and wherein each of said ridges has a planar upper surface falling along a first common surface plane, and each of said ridges has a planar lower surface falling along a second common surface plane, and the first and second common surface planes are parallel.

* * * * *